United States Patent
Gonzalez et al.

(10) Patent No.: US 9,072,773 B2
(45) Date of Patent: Jul. 7, 2015

(54) COMPOSITIONS FOR LABELING NERVES AND METHODS OF USE

(75) Inventors: Jesus Gonzalez, Carlsbad, CA (US); Junjie Liu, San Diego, CA (US)

(73) Assignee: AVELAS BIOSCIENCES, INC., La Jolla, CA (US)

( * ) Notice: Subject to any disclaimer, the term of this patent is extended or adjusted under 35 U.S.C. 154(b) by 0 days.

(21) Appl. No.: 13/819,312

(22) PCT Filed: Sep. 2, 2011

(86) PCT No.: PCT/US2011/050411
§ 371 (c)(1), (2), (4) Date: Apr. 25, 2013

(87) PCT Pub. No.: WO2012/031250
PCT Pub. Date: Mar. 8, 2012

(65) Prior Publication Data
US 2013/0202537 A1    Aug. 8, 2013

Related U.S. Application Data

(60) Provisional application No. 61/379,673, filed on Sep. 2, 2010.

(51) Int. Cl.
*A61K 49/00* (2006.01)
*G09F 13/04* (2006.01)
*G09F 13/18* (2006.01)
*G09F 13/22* (2006.01)
*G09F 13/44* (2006.01)

(52) U.S. Cl.
CPC ............ *A61K 49/0056* (2013.01); *G09F 13/04* (2013.01); *G09F 13/18* (2013.01); *G09F 13/22* (2013.01); *G09F 13/44* (2013.01); *G09F 2013/1863* (2013.01)

(58) Field of Classification Search
CPC ............ G01N 33/5008; G01N 33/582; G01N 33/5058; G01N 2500/00; G01N 33/5044; G01N 2500/10; G01N 33/5005; G01N 33/6896; G01N 2800/28; G01N 33/533; A61K 38/00; A61K 49/0032; A61K 49/0043; A61K 49/0056; C12N 5/0619
See application file for complete search history.

(56) References Cited

U.S. PATENT DOCUMENTS 6,602,980 B1 * 8/2003 Eyre .............................. 530/326
8,685,372 B2    4/2014 Tsien et al.

2004/0253243 A1    12/2004 Epstein et al.
2006/0228420 A1    10/2006 Martin
2007/0243554 A1    10/2007 Jagota et al.
2012/0148499 A1     6/2012 Tsien et al.

FOREIGN PATENT DOCUMENTS

WO    WO2006/105392        10/2006
WO    WO 2010/121023 A2 *  10/2010 ............ A61K 38/10
WO    WO2012/031250         3/2012

OTHER PUBLICATIONS

Arcidiacono et al. Cy5 labeled antimicrobial peptides for enhanced detection of *Escherichia coli* O157:H7. Biosens Bioelectron. Jun. 15, 2008;23(11):1721-7.*
Mikawa et al. Novel peptide ligands for integrin alpha 4 beta 1 overexpressed in cancer cells. Mol Cancer Ther 2004;3(10):1329-1334.*
Schmerr et al. A diagnostic test for scrapie-infected sheep using a capillary electrophoresis immunoassay with fluorescent-labeled peptides. Electrophoresis 1998, 19, 409-414.*
Chemical Book, FMOC-LYS(5/6-FAM)-OH, Jan. 1, 2008, Retrieved from the Internet: URL:http://www.chemicalbook.com/ProductChemicalPropertiesCB5335804_EN.htm, retrieved on Feb. 20, 2014.
EP11822751.1 Search Report dated Mar. 19, 2014.
Kobbert et al. 2000. Current concepts in neuroanatomical tracing. Progress in Neurobiology. 62:327-351.
Marangos et al. In vivo visualization of the cochlear nerve and nuclei with fluorescent axonal tracers. Hearing Research. 2001. 162:48-52.
O'Malley et al. Fluorescent Retrograde Axonal Tracing of the Facial Nerve. The Laryngoscope. 2006. 116:1792-1797.
PCT/US2011/050411 International Preliminary Report on Patentability dated Mar. 5, 2013.
PCT/US2011/050411 International Search Report and Written Opinion dated Oct. 31, 2012.
PCT/US2010/031231 International Search Report dated Jan. 3, 2011.
PCT/US2010/031231 International Preliminary Report on Patentability dated Oct. 27, 2011.
Richmond et al. Efficacy of seven retrograde tracers, compared in multiple-labelling studies of feline motoneurones. Journal of Neuroscience Methods. 1994. 53:35-46.

* cited by examiner

*Primary Examiner* — Karlheinz R Skowronek
*Assistant Examiner* — Jia-Hai Lee
(74) *Attorney, Agent, or Firm* — Wilson Sonsini Goodrich & Rosati

(57) ABSTRACT

The present invention provides methods for guiding preservation of neurons or nerves during surgery by administering a fluorescently-labeled peptide that associates with (e.g., specifically binds to) the neurons or nerves. The invention further provides targeting molecules of fluorescently-labeled peptides or aptamers that associate with (e.g., specifically bind to) neurons or nerves and for compositions thereof.

17 Claims, 22 Drawing Sheets

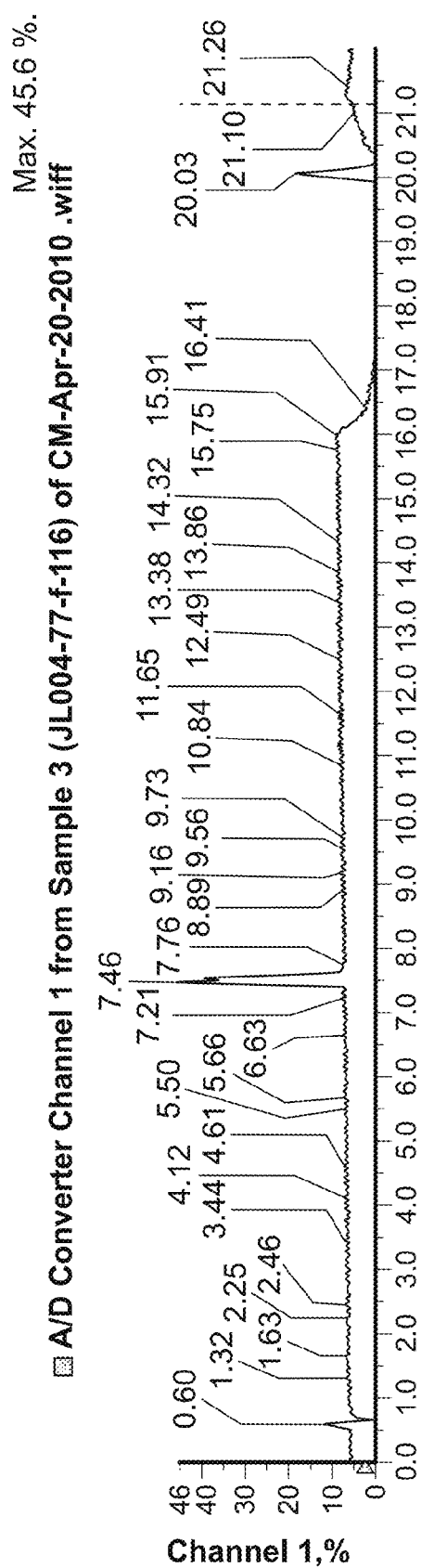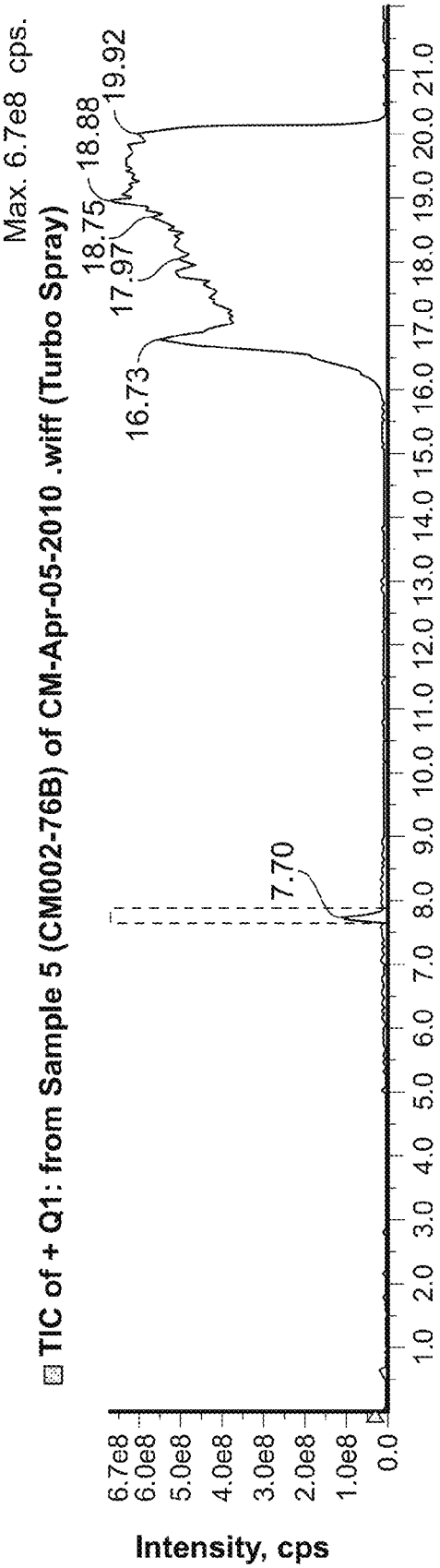
FIG. 10C
FIG. 10D

COMPOSITIONS FOR LABELING NERVES AND METHODS OF USE

CROSS-REFERENCE

This application is filed pursuant to 35 U.S.C. §371 as a United States National Phase Application of International Application No. PCT/US2011/050411 entitled "COMPOSITIONS FOR LABELING NERVES AND METHODS OF USE" filed Sep. 2, 2011, which claims the benefit under 35 U.S.C. §119(e) of U.S. Provisional Application 61/379,673, filed Sep. 2, 2010, both of which are incorporated herein by reference in their entirety.

The instant application contains a Sequence Listing which has been submitted in ASCII format via EFS-Web and is hereby incorporated by reference in its entirety. Said ASCII copy, created on Feb. 26, 2013, is named 39088707831.txt and is 3500 bytes in size.

BACKGROUND OF THE INVENTION

The central nervous system (CNS) consists of the brain and the spinal cord, as well as the retina.

The Peripheral Nervous System (PNS) extends outside the central nervous system (CNS). The peripheral nervous system is divided into the somatic nervous system and autonomic nervous system.

A neuron is an electrically excitable cell that processes and transmits information by electrical and chemical signaling. A typical neuron possesses a cell body (often called the soma), dendrites, and an axon.

A nerve is an enclosed, cable-like bundle of neural axons. Each nerve is a cordlike structure that contains many axons.

Each axon is surrounded by a layer of tissue called the endoneurium. The axons are bundled together into groups called fascicles, and each fascicle is wrapped in a layer of tissue called the perineurium. The neuron or nerve is wrapped in a layer of tissue called the epineurium.

SUMMARY OF THE INVENTION

Disclosed herein, in certain embodiments, are peptides that associate with (e.g., specifically bind to) a neuron, nerve, or tissue or structure associated therewith.

Disclosed herein, in certain embodiments, is a targeting molecule, comprising:
(a) a peptide sequence according to Formula (I):

Asn-X1-Gln-X2-Leu-X3-Lys-Ala-X4-Glu-His-Thr-Gly-Lys wherein X1 is selected from: Thr, Ser, Ala, or Glu;
wherein X2 is selected from: Thr, Ser, or Ala;
wherein X3 is selected from: Thr, Ser, Ala, His, or Phe; and
wherein X4 is selected from: Pro or Ala; and
(b) a cargo.

Disclosed herein, in certain embodiments, is a targeting molecule, comprising:
(a) a peptide sequence according to:

| | |
|---|---|
| X1-X2-X3-X4-X5-X6-X7-X8-X9-X10-X11-X12-Gly-X13 | (Formula (II)); |
| X2-X3-X4-X5-X6-X7-X8-X9-X10-X11-X12-Gly-X13 | (Formula (III)); |
| X3-X4-X5-X6-X7-X8-X9-X10-X11-X12-Gly-X13 | (Formula (IV)); |
| X4-X5-X6-X7-X8-X9-X10-X11-X12-Gly-X13 | (Formula (V)); |
| X5-X6-X7-X8-X9-X10-X11-X12-Gly-X13 | (Formula (VI)); |
| X6-X7-X8-X9-X10-X11-X12-Gly-X13 | (Formula (VII)); |
| X7-X8-X9-X10-X11-X12-Gly-X13 | (Formula (VIII)); |
| X8-X9-X10-X11-X12-Gly-X13 | (Formula (IX)); |
| X9-X10-X11-X12-Gly-X13 | (Formula (X)); |
| X10-X11-X12-Gly-X13 | (Formula (XI)); |
| X11-X12-Gly-X13 | (Formula (XII)); |
| X12-Gly-X13 | (Formula (XIII)); |
| Gly-X13 | (Formula (XIV)); |
| X13 | (Formula (XV)); |
| X10-X11-X12-Gly-X13-X14 | (Formula (XVI)); or |
| X10-X11-X12-Gly-X13-X14-X15 | (Formula (XVII)) | wherein X1 is selected from: Asn, Ala, or Pro;
wherein X2 is selected from: Thr, Ala, or Glu;
wherein X3 is selected from: Gln, Glu, Lys, or His;
wherein X4 is selected from: Thr or Ala;
wherein X5 is selected from: Leu or Lys;
wherein X6 is selected from: Ala, His, or Phe;
wherein X7 is selected from: Lys or Glu;
wherein X8 is selected from: Ala, Pro, D-Pro, or Phe;
wherein X9 is selected from: Pro or Ala;
wherein X10 is selected from: Glu, His, Ala, Thr, or Lys;
wherein X11 is selected from: His, Ala, Thr, Lys, or Glu;
wherein X12 is selected from: Ala or Thr;
wherein X13 is selected from: Lys, Cys, or Gly;
wherein X14 is selected from: Gly; and
wherein X15 is selected from: Cys; and
(b) a cargo.

Disclosed herein, in certain embodiments, is a targeting molecule, comprising:
(a) a peptide sequence according to:

| | |
|---|---|
| X7-X8-X9-X10-X11-X12-Gly-X13 | (Formula (VIII)); |
| X8-X9-X10-X11-X12-Gly-X13 | (Formula (IX)); |
| X9-X10-X11-X12-Gly-X13 | (Formula (X)); |
| X10-X11-X12-Gly-X13 | (Formula (XI)); |
| X11-X12-Gly-X13 | (Formula (XII)); |
| X12-Gly-X13 | (Formula (XIII)); |
| Gly-X13 | (Formula (XIV)); |
| X13 | (Formula (XV)); |
| X10-X11-X12-Gly-X13-X14 | (Formula (XVI)); or |
| X10-X11-X12-Gly-X13-X14-X15 | (Formula (XVII)) | wherein X7 is selected from: Lys or Glu;
wherein X8 is selected from: Ala, Pro, D-Pro, or Phe;
wherein X9 is selected from: Pro or Ala;
wherein X10 is selected from: Glu, His, Ala, Thr, or Lys;
wherein X11 is selected from: His, Ala, Thr, Lys, or Glu;
wherein X12 is selected from: Ala or Thr;
wherein X13 is selected from: Lys, Cys, or Gly;
wherein X14 is selected from: Gly; and
wherein X15 is selected from: Cys; and
(b) a cargo.

Disclosed herein, in certain embodiments, is a targeting molecule, comprising:
(a) a peptide sequence according to:

X8-X9-X10-X11-X12-Gly-X13  (Formula (IX));

X9-X10-X11-X12-Gly-X13  (Formula (X));

X10-X11-X12-Gly-X13  (Formula (XI));

X11-X12-Gly-X13  (Formula (XII));

X12-Gly-X13  (Formula (XIII));

X10-X11-X12-Gly-X13-X14  (Formula (XVI)); or

X10-X11-X12-Gly-X13-X14-X15  (Formula (XVII))

wherein X8 is selected from: Ala, Pro, D-Pro, or Phe;
wherein X9 is selected from: Pro or Ala;
wherein X10 is selected from: Glu, His, Ala, Thr, or Lys;
wherein X11 is selected from: His, Ala, Thr, Lys, or Glu;
wherein X12 is selected from: Ala or Thr;
wherein X13 is selected from: Lys, Cys, or Gly;
wherein X14 is selected from: Gly; and
wherein X15 is selected from: Cys; and
(b) a cargo.

Disclosed herein, in certain embodiments, is a targeting molecule, comprising:
(a) a peptide sequence according to Formula (IX):

X8-X9-X10-X11-X12-Gly-X13  (Formula (IX));

wherein X8 is selected from: Ala, Pro, D-Pro, or Phe;
wherein X9 is selected from: Pro or Ala;
wherein X10 is selected from: Glu, His, Ala, Thr, or Lys;
wherein X11 is selected from: His, Ala, Thr, Lys, or Glu;
wherein X12 is selected from: Ala or Thr; and
wherein X13 is selected from: Lys, Cys, or Gly; and
(b) a cargo.

Disclosed herein, in certain embodiments, is a targeting molecule, comprising:
(a) a peptide sequence according to Formula (X):

X9-X10-X11-X12-Gly-X13  (Formula (X));

wherein X9 is selected from: Pro or Ala;
wherein X10 is selected from: Glu, His, Ala, Thr, or Lys;
wherein X11 is selected from: His, Ala, Thr, Lys, or Glu;
wherein X12 is selected from: Ala or Thr; and
wherein X13 is selected from: Lys, Cys, or Gly; and
(b) a cargo.

Disclosed herein, in certain embodiments, is a targeting molecule, comprising:
(a) a peptide sequence according to Formula (XI):

X10-X11-X12-Gly-X13  (Formula (XI));

wherein X10 is selected from: Glu, His, Ala, Thr, or Lys;
wherein X11 is selected from: His, Ala, Thr, Lys, or Glu;
wherein X12 is selected from: Ala or Thr; and
wherein X13 is selected from: Lys, Cys, or Gly; and
(b) a cargo.

Disclosed herein, in certain embodiments, is a targeting molecule, comprising:
(a) a peptide sequence according to Formula (XII):

X11-X12-Gly-X13  (Formula (XII));

wherein X11 is selected from: His, Ala, Thr, Lys, or Glu;
wherein X12 is selected from: Ala or Thr; and
wherein X13 is selected from: Lys, Cys, or Gly; and
(b) a cargo.

Disclosed herein, in certain embodiments, is a targeting molecule, comprising:
(a) a peptide sequence according to Formula (XIII):

X12-Gly-X13  (Formula (XIII));

wherein X12 is selected from: Ala or Thr; and
wherein X13 is selected from: Lys, Cys, or Gly; and
(b) a cargo.

Disclosed herein, in certain embodiments, is a targeting molecule, comprising:
(a) a peptide sequence according to Formula (XVI):

X10-X11-X12-Gly-X13-X14  (Formula (XVI));

wherein X10 is selected from: Glu, His, Ala, Thr, or Lys;
wherein X11 is selected from: His, Ala, Thr, Lys, or Glu;
wherein X12 is selected from: Ala or Thr;
wherein X13 is selected from: Lys, Cys, or Gly; and
wherein X14 is selected from: Gly; and
(b) a cargo.

Disclosed herein, in certain embodiments, is a targeting molecule, comprising:
(a) a peptide sequence according to Formula (XVII):

X10-X11-X12-Gly-X13-X14-X15  (Formula (XVII));

wherein X10 is selected from: Glu, His, Ala, Thr, or Lys;
wherein X11 is selected from: His, Ala, Thr, Lys, or Glu;
wherein X12 is selected from: Ala or Thr;
wherein X13 is selected from: Lys, Cys, or Gly;
wherein X14 is selected from: Gly; and
wherein X15 is selected from: Cys; and
(b) a cargo.

Disclosed herein, in certain embodiments, is a targeting molecule, comprising:
(a) a peptide sequence selected from: Glu-His-Thr-Gly-Lys (SEQ ID NO. 1); Lys-Ala-Pro-Glu-His-Thr-Gly-Lys (SEQ ID NO. 2); Leu-Ala-Lys-Ala-Pro-Glu-His-Thr-Gly-Lys (SEQ ID NO. 3); Gln-Thr-Leu-Ala-Lys-Ala-Pro-Glu-His-Thr-Gly-Lys (SEQ ID NO. 4); Thr-Gln-Thr-Leu-Ala-Lys-Ala-Pro-Glu-His-Thr-Gly-Lys (SEQ ID NO. 5); Asn-Thr-Gln-Thr-Leu-Ala-Lys-Ala-Pro-Glu-His-Thr-Gly-Lys (SEQ ID NO. 6); Asn-Thr-Gln-Thr-Leu-Ala-Lys-Ala-Pro-Glu-His-Ala-Gly-Lys (SEQ ID NO. 7); Asn-Thr-Gln-Thr-Leu-Ala-Lys-Ala-Pro-Glu-Ala-Thr-Gly-Lys (SEQ ID NO. 8); Asn-Thr-Gln-Thr-Leu-Ala-Lys-Ala-Pro-His-Glu-Thr-Gly-Lys (SEQ ID NO. 9); Asn-Thr-Gln-Thr-Leu-Ala-Lys-Ala-Pro-Ala-His-Thr-Gly-Lys (SEQ ID NO. 10); Asn-Thr-Gln-Thr-Leu-Ala-Lys-Ala-Pro-Lys-His-Thr-Gly-Lys (SEQ ID NO. 11); Asn-Thr-Gln-Thr-Leu-Ala-Lys-Ala-Ala-Glu-His-Thr-Gly-Lys (SEQ ID NO. 12); Asn-Thr-Gln-Thr-Leu-Ala-Lys-Ala-D-pro-Glu-His-Thr-Gly-Lys (SEQ ID NO. 13); Asn-Thr-Gln-Thr-Leu-Ala-Lys-Pro-Pro-Glu-His-Thr-Gly-Lys (SEQ ID NO. 14); Asn-Thr-Gln-Thr-Leu-Ala-Lys-Phe-Pro-Glu-His-Thr-Gly-Lys (SEQ ID NO. 15); Asn-Thr-Gln-Thr-Leu-Ala-Glu-Ala-Pro-Glu-His-Thr-Gly-Lys (SEQ ID NO. 16); Asn-Thr-Gln-Thr-Leu-His-Glu-Ala-Pro-Glu-His-Thr-Gly-Lys (SEQ ID NO. 17); Asn-Thr-Gln-Thr-Leu-Phe-Lys-Ala-Pro-Glu-His-Thr-Gly-Lys (SEQ ID NO. 18); Asn-Thr-Gln-Thr-Lys-Ala-Lys-Ala-Pro-Glu-His-Thr-Gly-Lys (SEQ ID NO. 19); Asn-Thr-Gln-Ala-Leu-Ala-Lys-Ala-Pro-Glu-His-Thr-Gly-Lys (SEQ ID NO. 20); Asn-Thr-Glu-Thr-Leu-Ala-Lys-Ala-Pro-Glu-His-Thr-Gly-Lys (SEQ ID NO. 21); Asn-Thr-Lys-Thr-Leu-Ala-Lys-Ala-Pro-Glu-His-Thr-Gly-Lys (SEQ ID NO. 22); Asn-Ala-Gln-Thr-Leu-Ala-Lys-Ala-Pro-Glu-His-Thr-Gly-Lys (SEQ ID NO. 23); Ala-Thr-Gln-Thr-Leu-Ala-Lys- Ala-Pro-Glu-His-Thr-Gly-Lys (SEQ ID NO. 24); Pro-Glu-His-Thr-Leu-Ala-Lys-Ala-Pro-Glu-His-Thr-Gly-Lys (SEQ ID NO. 25); Glu-His-Thr-Gly-Cys (SEQ ID NO. 26); Glu-His-Thr-Gly-Gly-Gly-Cys (SEQ ID NO. 27); Lys (SEQ ID NO. 28); Gly-Lys (SEQ ID NO. 29); Thr-Thr-Thr-Gly-Gly-Gly-Cys (SEQ ID NO. 30); Glu-glu-Thr-Gly-Gly-Gly-Cys (SEQ ID NO. 31); Lys-His-Thr-Gly-Gly-Gly-Cys (SEQ ID NO. 32); Glu-Lys-Thr-Gly-Gly-Gly-Cys (SEQ ID NO. 33); and a cargo.

Disclosed herein, in certain embodiments, is a targeting molecule, comprising:
  (a) a peptide sequence selected from: Gly-Lys (SEQ ID NO. 29); Thr-Thr-Thr-Gly-Gly-Gly-Cys (SEQ ID NO. 30); Glu-glu-Thr-Gly-Gly-Gly-Cys (SEQ ID NO. 31); Lys-His-Thr-Gly-Gly-Gly-Cys (SEQ ID NO. 32); Glu-Lys-Thr-Gly-Gly-Gly-Cys (SEQ ID NO. 33); and
  (b) a cargo.

Disclosed herein, in certain embodiments, is a targeting molecule, comprising:
  (a) a peptide comprising the sequence: Gly-Lys (SEQ ID NO. 29); and
  (b) a cargo.

Disclosed herein, in certain embodiments, is a targeting molecule, comprising:
  (a) a peptide comprising the sequence: Thr-Thr-Thr-Gly-Gly-Gly-Cys (SEQ ID NO. 30); and
  (b) a cargo.

Disclosed herein, in certain embodiments, is a targeting molecule, comprising:
  (a) a peptide comprising the sequence: Glu-glu-Thr-Gly-Gly-Gly-Cys (SEQ ID NO. 31); and
  (b) a cargo.

Disclosed herein, in certain embodiments, is a targeting molecule, comprising:
  (a) a peptide comprising the sequence: Lys-His-Thr-Gly-Gly-Gly-Cys (SEQ ID NO. 32); and
  (b) a cargo.

Disclosed herein, in certain embodiments, is a targeting molecule, comprising:
  (a) a peptide comprising the sequence: Glu-Lys-Thr-Gly-Gly-Gly-Cys (SEQ ID NO. 33); and
  (a) a cargo.

In some embodiments of any targeting molecule disclosed herein, the cargo is an imaging agent. In some embodiments of any targeting molecule disclosed herein, the cargo is a dye, a fluorescent moiety, a positron-emitting isotope, a gamma-emitting isotope, or a paramagnetic molecule or nanoparticle. In some embodiments of any targeting molecule disclosed herein, the cargo is: a fluorescent protein, a fluorescent peptide, a fluorescent dye, a fluorescent material or a combination thereof. In some embodiments of any targeting molecule disclosed herein, the cargo is: a xanthene; a bimane; a coumarin; an aromatic amine; a benzofuran; a fluorescent cyanine; an indocarbocyanine; a carbazole; a dicyanomethylene pyrane; a polymethine; an oxabenzanthrane; a pyrylium; a carbostyl; a perylene; an acridone; a quinacridone; a rubrene; an anthracene; a coronene; a phenanthrecene; a pyrene; a butadiene; a stilbene; a porphyrin; a pthalocyanine; a lanthanide metal chelate complexe; a rare-earth metal chelate complexe; derivatives thereof; or a combination thereof. In some embodiments of any targeting molecule disclosed herein, the cargo is: 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrin, Venus, YPet, or a combination thereof. In some embodiments of any targeting molecule disclosed herein, the cargo is: a gadolinium chelate, an iron oxide particle, a super paramagnetic iron oxide particle, an ultra small paramagnetic particle, a manganese chelate, gallium containing agent, or a combination thereof. In some embodiments of any targeting molecule disclosed herein, the cargo is a radionucleotide chelate selected from: diethylene triamine pentaacetic acid (DTPA); 1,4,7,10-tetraazacyclododecane-1,4,7,10-tetraacetic acid (DOTA); 1,4,7-triazacyclononane-N,N',N'''-triacetic acid (NOTA); 6-Hydrazinopyridine-3-carboxylic acid (HYNIC); or a combination thereof. In some embodiments of any targeting molecule disclosed herein, the cargo is a radionucleotide selected from: $^{99m}$Tc, $^{64}$Cu, $^{18}$F, $^{124}$I, $^{111}$In, or a combination thereof. In some embodiments of any targeting molecule disclosed herein, the cargo is: $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, radioactive isotopes of Lu, or a combination thereof. In some embodiments of any targeting molecule disclosed herein, the cargo is an indocarbocyanine dye. In some embodiments of any targeting molecule disclosed herein, the cargo is: Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments of any targeting molecule disclosed herein, the cargo is: Cy5 indocarbocyanine dye. In some embodiments of any targeting molecule disclosed herein, the cargo is an active agent. In some embodiments of any targeting molecule disclosed herein, the cargo is: an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof. In some embodiments of any targeting molecule disclosed herein, the cargo is: benzocaine; carticaine; cinchocaine; cyclomethycaine; lidocaine; prilocalne; propxycaine; proparacaine; tetracaine; tocamide; and trimecaine; methotrexate; cyclophosphamide; thalidomide; paclitaxel; pemetrexed; pentostatin; pipobroman; pixantrone; plicamycin; procarbazine; raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; carbamazepine; oxcarbazepine; phenylein; valproic acid; sodium valproate; cinnarizine; flunarizine; nimodipine; brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); or a combination thereof.

Disclosed herein, in certain embodiments, is a method of imaging a target, comprising imaging a target contacted with a targeting molecule disclosed herein, wherein the cargo is an imaging agent. In some embodiments, the target is a neuron, nerve, or tissue or external structure associated therewith. In some embodiments, the target is a neuromuscular junction, the sinoartial node, the atriventricular node, or a combination thereof. In some embodiments, the imaging agent is a dye, a fluorescent moiety, a positron-emitting isotope, a gamma-ray isotope, or a paramagnetic molecule or nanoparticle. In some embodiments, the imaging agent is selected from: a fluorescent protein, a fluorescent peptide, a fluorescent dye, a fluorescent material or a combination thereof. In some embodiments, the imaging agent is: a xanthene; a bimane; a coumarin; an aromatic amine; a benzofuran; a fluorescent cyanine; an indocarbocyanine; a carbazole; a dicyanomethylene pyrane; a polymethine; an oxabenzanthrane; a pyrylium; a carbostyl; a perylene; an acridone; a quinacridone; a rubrene; an anthracene; a coronene; a phenanthrecene; a pyrene; a butadiene; a stilbene; a porphyrin; a pthalocyanine; a lanthanide metal chelate complex; a rare-earth metal chelate complexe; derivatives thereof; or a combination thereof. In some embodiments, the imaging agent is: 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrin, Venus, YPet, or a combination thereof. In some embodiments, the imaging agent is: a gadolinium chelate, an iron oxide particle, a super paramagnetic iron oxide particle, an ultra small paramagnetic particle, a manganese chelate, gallium containing agent, or a combination thereof. In some embodiments, the imaging agent is a radionucleotide chelate selected from: diethylene triamine pentaacetic acid (DTPA); 1,4,7,10-tetraazacyclododecane-1,4,7,10-tetraacetic acid (DOTA); 1,4,7-triazacyclononane-N,N',N"-triacetic acid (NOTA); 6-Hydrazinopyridine-3-carboxylic acid (HYNIC); or a combination thereof. In some embodiments, the imaging agent is a radionucleotide selected from: $^{99m}$Tc, $^{64}$Cu, $^{18}$F, $^{124}$I, $^{111}$In, or a combination thereof. In some embodiments, the imaging agent is: $^{211}$At, $^{131}$I, $^{125}$I, $^{90}$Y, $^{186}$Re, $^{188}$Re, $^{153}$Sm, $^{212}$Bi, $^{32}$P $^{11}$C, $^{201}$Tl, $^{57}$Ga, radioactive isotopes of Lu, or a combination thereof.

Disclosed herein, in certain embodiments, is a method of a guiding surgical procedure on an individual in need thereof, comprising administering to the individual a targeting molecule disclosed herein, wherein the cargo is an imaging agent. In some embodiments, the imaging agent is a dye, a fluorescent moiety, a positron-emitting isotope, a gamma-ray isotope, or a paramagnetic molecule or nanoparticle. In some embodiments, the imaging agent is selected from: a fluorescent protein, a fluorescent peptide, a fluorescent dye, a fluorescent material or a combination thereof. In some embodiments, the imaging agent is: a xanthene; a bimane; a coumarin; an aromatic amine; a benzofuran; a fluorescent cyanine; an indocarbocyanine; a carbazole; a dicyanomethylene pyrane; a polymethine; an oxabenzanthrane; a pyrylium; a carbostyl; a perylene; an acridone; a quinacridone; a rubrene; an anthracene; a coronene; a phenanthrecene; a pyrene; a butadiene; a stilbene; a porphyrin; a pthalocyanine; a lanthanide metal chelate complex; a rare-earth metal chelate complexe; derivatives thereof; or a combination thereof. In some embodiments, the imaging agent is: 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrin, Venus, YPet, or a combination thereof. In some embodiments, the imaging agent is: a gadolinium chelate, an iron oxide particle, a super paramagnetic iron oxide particle, an ultra small paramagnetic particle, a manganese chelate, gallium containing agent, or a combination thereof. In some embodiments, the imaging agent is a radionucleotide chelate selected from: diethylene triamine pentaacetic acid (DTPA); 1,4,7,10-tetraazacyclododecane-1,4,7,10-tetraacetic acid (DOTA); 1,4,7-triazacyclononane-N,N',N"-triacetic acid (NOTA); 6-Hydrazinopyridine-3-carboxylic acid (HYNIC); or a combination thereof. In some embodiments, the imaging agent is a radionucleotide selected from: $^{99m}$Tc, $^{64}$Cu, $^{18}$F, $^{124}$I, $^{111}$In, or a combination thereof. In some embodiments, the imaging agent is: $^{211}$At, $^{131}$I, $^{125}$I, $^{90}$Y, $^{186}$Re, $^{188}$Re, $^{153}$Sm, $^{212}$Bi, $^{32}$P $^{11}$C, $^{201}$Tl, $^{57}$Ga, radioactive isotopes of Lu, or a combination thereof.

Disclosed herein, in certain embodiments, is a method of delivering a drug to a target, comprising contacting the target with a targeting molecule according to any of claims 1-18, wherein the cargo is an active agent. In some embodiments, the target is a neuron, nerve, or tissue or external structure associated therewith. In some embodiments, the target is a neuromuscular junction, the sinoartial node, the atriventricular node, or a combination thereof. In some embodiments, the active agent is selected from: an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof. In some embodiments, the active agent is selected from: benzocaine; carticaine; cinchocaine; cyclomethycaine; lidocaine; prilocalne; propxycaine; proparacaine; tetracaine; tocamide; and trimecaine; methotrexate; cyclophosphamide; thalidomide; paclitaxel; pemetrexed; pentostatin; pipobroman; pixantrone; plicamycin; procarbazine; raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; carbamazepine; oxcarbazepine; phenylein; valproic acid; sodium valproate; cinnarizine; flunarizine; nimodipine; brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); or a combination thereof.

Disclosed herein, in certain embodiments, is a pharmaceutical composition comprising: (a) a targeting molecule disclosed herein; and (b) a pharmaceutically acceptable excipient.

DETAILED DESCRIPTION OF THE INVENTION

Introduction

Figure 1:
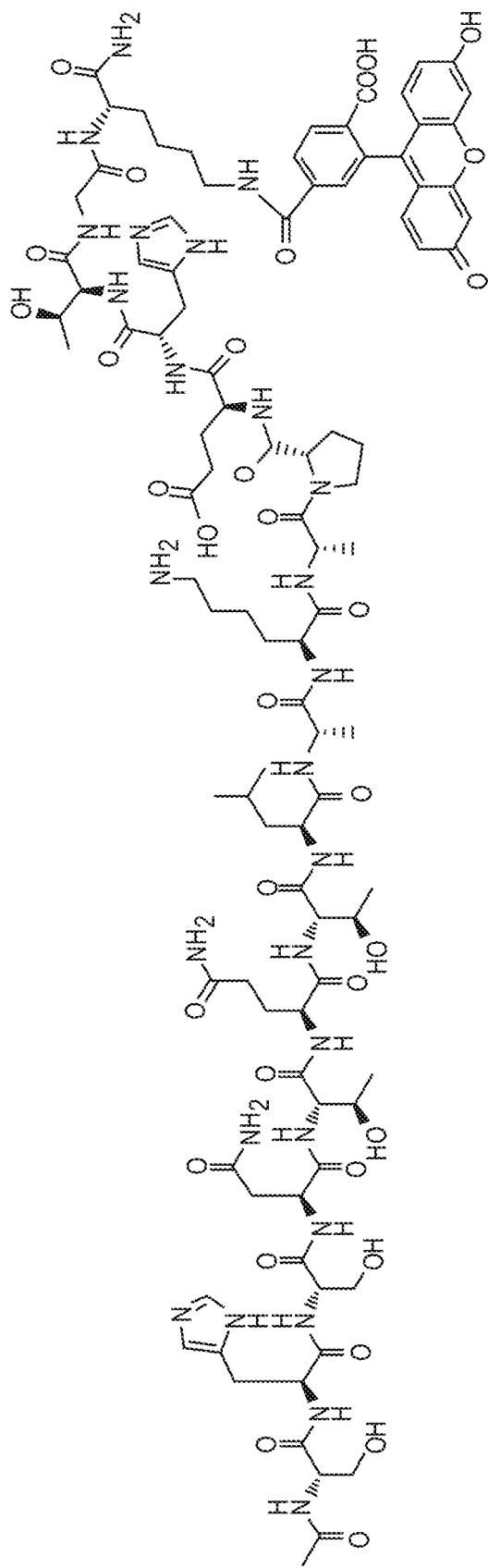
FIG. 1 illustrates the chemical structure of Peptide A.
Figure 2:
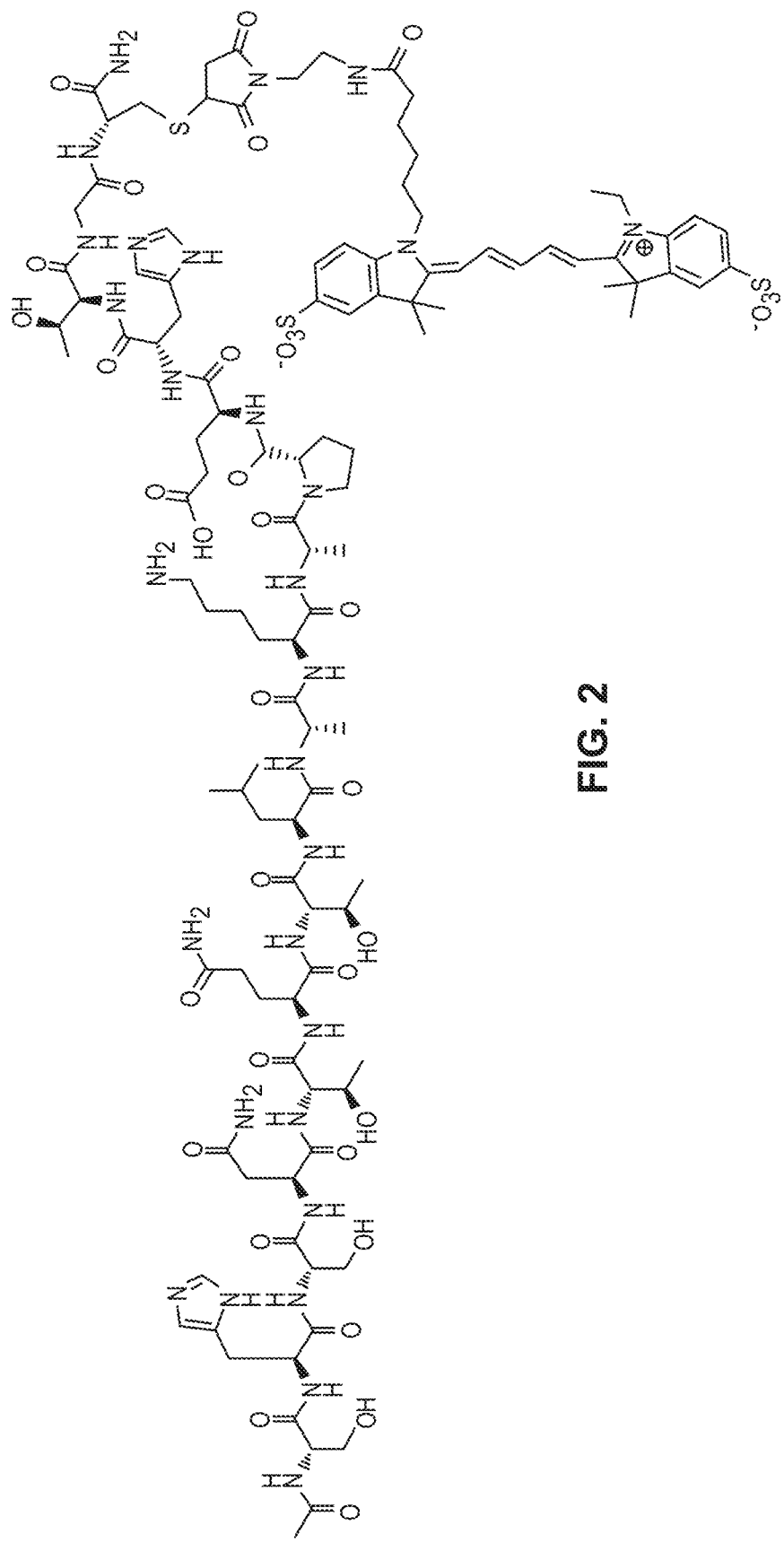
FIG. 2 illustrates the chemical structure of Peptide B.
Figure 3:
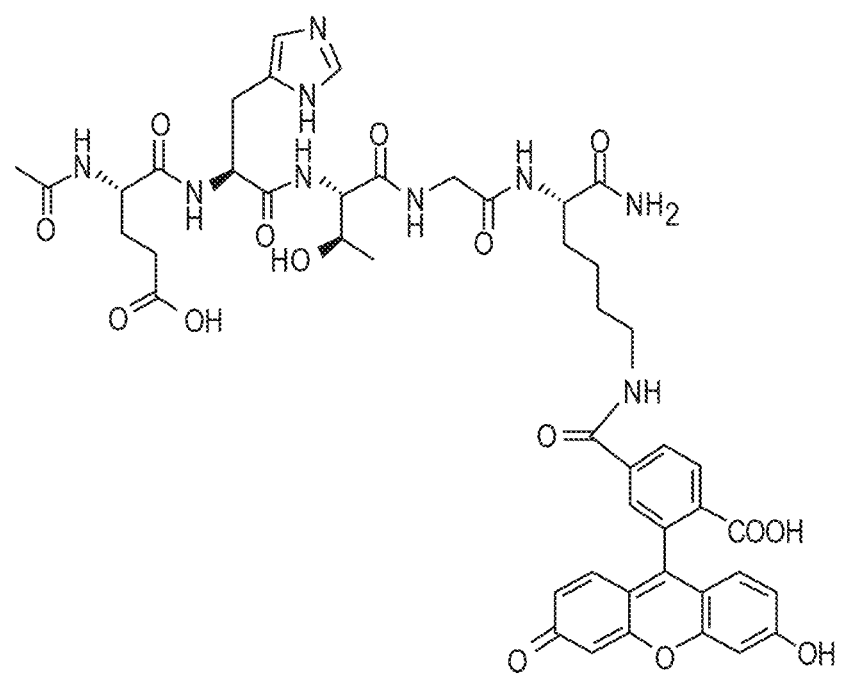
FIG. 3 illustrates the chemical structure of Peptide 3.

Identification of neurons, nerves, and tissues (e.g., the sinoatrial node and the atrioventricular node) and structures associated therewith (e.g., neuromuscular junctions) is one of the most important goals of any surgical procedure as unintended damage (e.g., accidental transaction) to a neurons, nerves, and tissues (e.g., the sinoatrial node and the atrioventricular node) and structures associated therewith (e.g., neuromuscular junctions) may result in significant morbidity. Nerves are typically identified by their elongated whitish appearance and relationship to nearby structures or by electrophysiological studies. However, in instances such as trauma, tumor involvement, inflammation, congenital disease or infection, identification using these criteria can be difficult. There is a need for methods of reliably and conclusively identifying neurons, nerves, and tissues (e.g., the sinoatrial node and the atrioventricular node) and structures associated therewith (e.g., neuromuscular junctions) which overcome the deficiencies in the art.

Identification of neurons, nerves, and tissues (e.g., the sinoatrial node and the atrioventricular node) and structures associated therewith (e.g., neuromuscular junctions) is currently accomplished by electromyographic (EMG) monitoring. This technique, however, has the disadvantage of not providing visual feedback to the operating surgeon during the surgery. There is no visual guidance to the operating surgeon as to how far away from the stimulation site the neuron or nerve lies or the direction of travel the neuron or nerve takes from the stimulation site. Furthermore, EMG only traces motor pathways, not sensory fibers. EMG fails if neuron or nerve conduction or neuromuscular transmission is temporarily blocked anywhere distal to the recording site. Such blockade easily occurs due to neuron or nerve compression, trauma, local anesthetics, or neuromuscular blockers.

Neuron or nerve labeling primarily depends on retrograde or anterograde tracing of individually identified axonal tracts via the use of fluorescent dyes. However, methods of labeling neuron or nerves by locally applied fluorescent tracers have several disadvantages. First, this technique can label only one neuron or nerve fiber tract at a time, depending on where the dye has been injected. Second, this technique results in only limited labeling of fluorescent dyes along the axonal tracts, because retrograde axonal tracers typically accumulate in the neural cell body. Third, retrograde transport is relatively slow (on the order of millimeters per day) and therefore takes a long time to label human neuron or nerves, which are often longer than a meter, such as in the case of the sciatic neuron or nerve and its arborizations. Fourth, the application of fluorescent dyes to innervation targets such as direct intramuscular injections to label motor neuron or nerves is typically messy with a variable amount of the tracer dye remaining at the injection site. As dissection of neuron or nerves depends on accurate visualization of adjacent structures prior to encountering them, a surgical site that is contaminated with fluorescent dyes would not be desirable. Finally, the direct injection of the fluorescent dye itself may be damaging to the target organs or neuron or nerve of interest, either by mechanical damage or by the very high local concentration of dye and vehicle at the injection site.

Certain Definitions

As used herein, the following terms have the meanings ascribed to them unless specified otherwise.

As used herein, the term "neuron" means an electrically excitable cell that processes and transmits information by electrical and chemical signaling. Neurons possess a cell body (i.e., the soma), dendrites, and an axon. Neurons are electrically excitable, maintaining voltage gradients across their membranes by ion pumps, which combine with ion channels embedded in the membrane to generate intracellular-versus-extracellular concentration differences of ions (e.g., sodium, potassium, chloride, and calcium). A neuron may or may not include a myelin sheath. The term "neuron" is intended to include any tissues (e.g., the sinoatrial node or atrioventricular node) or structures associated therewith (e.g., neuromuscular junctions).

As used herein, the term "nerve" means a bundle of neural axons. Within a nerve, each axon is surrounded by a layer of connective tissue called the endoneurium. The axons are bundled together into groups called fascicles, and each fascicle is wrapped in a layer of connective tissue called the perineurium. The entire nerve is wrapped in a layer of connective tissue called the epineurium. The term "nerve" is intended to include any tissues (e.g., the sinoatrial node or the atriventricular node) or structures associated therewith (e.g., neuromuscular junctions).

As used herein, the term "targeting molecule" refers to any agent (e.g., peptide, protein, nucleic acid polymer, aptamer, or small molecule) that associates with (e.g., binds to) a target of interest. The target of interest may be a tissue, a cell, a cellular structure (e.g., an organelle), a protein, a peptide, a polysaccharide, or a nucleic acid polymer. In some embodiments, the targeting molecule is any agent that associates with (e.g., binds to) one or more neurons, nerves, or tissues or structures associated therewith.

The terms "polypeptide," "peptide" and "protein" are used interchangeably herein to refer to a polymer of amino acid residues. The terms apply to naturally occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds. As used herein, the terms "peptide" refers to a polymer of amino acid residues typically ranging in length from 2 to about 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an α-ester, a β-ester, a thioamide, phosphonamide, carbamate, hydroxylate, and the like (see, e.g., Spatola, (1983) Chem. Biochem. Amino Acids and Proteins 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids are either D amino acids or L amino acids.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

As used herein, the term "label" refers to a molecule that facilitates the visualization and/or detection of a targeting molecule disclosed herein. In some embodiments, the label is a fluorescent moiety.

The phrase "specifically binds" when referring to the interaction between a targeting molecule disclosed herein and a target (e.g., purified protein, neuron or nerve tissue, neuron or nerves, cranial neuron or nerves, central neuron or nerves, myelinated or unmyelinated neuron or nerves, connective tissue surrounding neuron or nerves, or external structures associated with neurons and nerves (e.g., neuromuscular junctions)), refers to the formation of a high affinity association between the targeting molecule and the target. Further, the term means that the targeting molecule has low affinity for non-targets.

"Selective binding," "selectivity," and the like refer the preference of agent to interact with one molecule as compared to another. Preferably, interactions between a targeting molecule disclosed herein and a target are both specific and selective. Note that in some embodiments an agent is designed to "specifically bind" and "selectively bind" two distinct, yet similar targets without binding to other undesirable targets.

The terms "individual," "patient," and "subject" are used interchangeably. As used herein, they mean any mammal (i.e. species of any orders, families, and genus within the taxonomic classification animalia: chordata: vertebrata: mammalia). In some embodiments, the mammal is a human. In some embodiments, the mammal is a non-human. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The terms "administer," "administering", "administration," and the like, as used herein, refer to methods used to enable delivery of agents or compositions disclosed herein to the desired site of biological action. These methods include, but are not limited to parenteral injection (e.g., intravenous, subcutaneous, intraperitoneal, intramuscular, intravascular, intrathecal, intravitreal, infusion, or local). Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "surgery" as used herein, refers to any method used to manipulate, change, or cause an effect by a physical intervention. These methods include, but are not limited to open surgery, endoscopic surgery, laparoscopic surgery, minimally invasive surgery, robotic surgery, any procedures that may affect any neuron or nerve, such as placement of retractors during spinal surgery, electrically conducting cardiac tissue or nerve ablation, epidural injection, intrathecal injections, neuron or nerve blocks, implantation of devices such as neuron or nerve stimulators and implantation of pumps.

Targets

Disclosed herein, in certain embodiments, are targeting molecules that associate with (e.g., specifically bind to) a target. In some embodiments, the target is neurons, nerves, or tissues (e.g., the sinoatrial node and the atrioventricular node) or structures associated therewith (e.g., neuromuscular junctions). The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, or lumbrosacral plexus). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination.

In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is an external structure associated with a nerve or neuron (e.g., a neuromuscular junction). In some embodiments, the target is a neuromuscular junction. In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors).

In some embodiments, the target is electrically excitable tissue including nerves and muscle. In some embodiments, the target is the conducting fibers of electrically excitable tissues. In some embodiments, the target is cardiac excitable tissue.

Determining whether a targeting molecule is capable of associating with (e.g., binding to) a neuron or nerve or component thereof is accomplished by any suitable method. In some embodiments, the method of determining whether a targeting molecule is capable of associating with (e.g., binding to) a neuron or nerve or component thereof involves contacting a targeting molecule (e.g., peptide) disclosed herein with a test agent for a period of time sufficient to allow the targeting molecule and test agent to form a binding complex. The binding complex is detected using any suitable method. Suitable binding assays can be performed in vitro or in vivo and include, but are not limited to, phage display, two-hybrid screens, co-precipitation, cross-linking, and expression cloning (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to the target of interest. The targeting molecule utilized in such assays can be naturally expressed, cloned or synthesized.

Targeting Molecules

In some embodiments, the targeting molecule comprises (a) a peptide sequence according to the Formula (I):

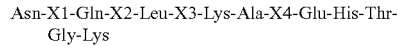
Asn-X1-Gln-X2-Leu-X3-Lys-Ala-X4-Glu-His-Thr-Gly-Lys wherein X1 is selected from: Thr, Ser, Ala, or Glu;
wherein X2 is selected from: Thr, Ser, or Ala;
wherein X3 is selected from: Thr, Ser, Ala, His, or Phe; and
wherein X4 is selected from: Pro or Ala; and
(b) a cargo.

In some embodiments, the targeting molecule comprises (a) a peptide sequence according to the following:

X1-X2-X3-X4-X5-X6-X7-X8-X9-X10-X11-X12-Gly-X13 (Formula (II));

X2-X3-X4-X5-X6-X7-X8-X9-X10-X11-X12-Gly-X13 (Formula (III));

X3-X4-X5-X6-X7-X8-X9-X10-X11-X12-Gly-X13 (Formula (IV));

X4-X5-X6-X7-X8-X9-X10-X11-X12-Gly-X13 (Formula (V));

X5-X6-X7-X8-X9-X10-X11-X12-Gly-X13 (Formula (VI));

X6-X7-X8-X9-X10-X11-X12-Gly-X13 (Formula (VII));

X7-X8-X9-X10-X11-X12-Gly-X13 (Formula (VIII));

X8-X9-X10-X11-X12-Gly-X13 (Formula (IX));

X9-X10-X11-X12-Gly-X13 (Formula (X));

X10-X11-X12-Gly-X13 (Formula (XI));

X11-X12-Gly-X13 (Formula (XII));

X12-Gly-X13 (Formula (XIII));

Gly-X13 (Formula (XIV));

X13 (Formula (XV));

X10-X11-X12-Gly-X13-X14 (Formula (XVI)); or

X10-X11-X12-Gly-X13-X14-X15 (Formula (XVII))

wherein X1 is selected from: Asn, Ala, or Pro;
wherein X2 is selected from: Thr, Ala, or Glu;
wherein X3 is selected from: Gln, Glu, Lys, or His;
wherein X4 is selected from: Thr or Ala;
wherein X5 is selected from: Leu or Lys;
wherein X6 is selected from: Ala, His, or Phe;
wherein X7 is selected from: Lys or Glu;
wherein X8 is selected from: Ala, Pro, D-Pro, or Phe;
wherein X9 is selected from: Pro or Ala;
wherein X10 is selected from: Glu, His, Ala, Thr, or Lys;
wherein X11 is selected from: His, Ala, Thr, Lys, or Glu;
wherein X12 is selected from: Ala or Thr;
wherein X13 is selected from: Lys, Cys, or Gly;
wherein X14 is selected from: Gly; and
wherein X15 is selected from: Cys; and
(b) a cargo.

In some embodiments, the targeting molecule comprises (a) a peptide sequence according to the following:

X7-X8-X9-X10-X11-X12-Gly-X13 (Formula (VIII));

X8-X9-X10-X11-X12-Gly-X13 (Formula (IX));

X9-X10-X11-X12-Gly-X13 (Formula (X));

X10-X11-X12-Gly-X13 (Formula (XI));

X11-X12-Gly-X13 (Formula (XII));

X12-Gly-X13 (Formula (XIII));

Gly-X13 (Formula (XIV));

X13 (Formula (XV));

X10-X11-X12-Gly-X13-X14 (Formula (XVI)); or

X10-X11-X12-Gly-X13-X14-X15 (Formula (XVII))

wherein X7 is selected from: Lys or Glu;
wherein X8 is selected from: Ala, Pro, D-Pro, or Phe;
wherein X9 is selected from: Pro or Ala;
wherein X10 is selected from: Glu, His, Ala, Thr, or Lys;
wherein X11 is selected from: His, Ala, Thr, Lys, or Glu;
wherein X12 is selected from: Ala or Thr;
wherein X13 is selected from: Lys, Cys, or Gly;
wherein X14 is selected from: Gly; and
wherein X15 is selected from: Cys; and
(b) a cargo.

In some embodiments, the targeting molecule comprises (a) a peptide sequence according to the following:

X8-X9-X10-X11-X12-Gly-X13 (Formula (IX));

X9-X10-X11-X12-Gly-X13 (Formula (X));

X10-X11-X12-Gly-X13 (Formula (XI));

X11-X12-Gly-X13 (Formula (XII));

X12-Gly-X13 (Formula (XIII));

X10-X11-X12-Gly-X13-X14 (Formula (XVI)); or

X10-X11-X12-Gly-X13-X14-X15 (Formula (XVII))

wherein X8 is selected from: Ala, Pro, D-Pro, or Phe;
wherein X9 is selected from: Pro or Ala;
wherein X10 is selected from: Glu, His, Ala, Thr, or Lys;
wherein X11 is selected from: His, Ala, Thr, Lys, or Glu;
wherein X12 is selected from: Ala or Thr;
wherein X13 is selected from: Lys, Cys, or Gly;
wherein X14 is selected from: Gly; and
wherein X15 is selected from: Cys; and
(b) a cargo.

In some embodiments, the targeting molecule comprises (a) a peptide sequence according to the following:

X8-X9-X10-X11-X12-Gly-X13 (Formula (IX));

wherein X8 is selected from: Ala, Pro, D-Pro, or Phe;
wherein X9 is selected from: Pro or Ala;
wherein X10 is selected from: Glu, His, Ala, Thr, or Lys;
wherein X11 is selected from: His, Ala, Thr, Lys, or Glu;
wherein X12 is selected from: Ala or Thr; and
wherein X13 is selected from: Lys, Cys, or Gly; and
(b) a cargo.

In some embodiments, the targeting molecule comprises (a) a peptide sequence according to the following:

X9-X10-X11-X12-Gly-X13 (Formula (X));

wherein X9 is selected from: Pro or Ala;
wherein X10 is selected from: Glu, His, Ala, Thr, or Lys;
wherein X11 is selected from: His, Ala, Thr, Lys, or Glu;
wherein X12 is selected from: Ala or Thr; and
wherein X13 is selected from: Lys, Cys, or Gly; and
(b) a cargo.

In some embodiments, the targeting molecule comprises (a) a peptide sequence according to the following:

X10-X11-X12-Gly-X13 (Formula (XI));

wherein X10 is selected from: Glu, His, Ala, Thr, or Lys;
wherein X11 is selected from: His, Ala, Thr, Lys, or Glu;
wherein X12 is selected from: Ala or Thr; and
wherein X13 is selected from: Lys, Cys, or Gly; and
(b) a cargo.

In some embodiments, the targeting molecule comprises (a) a peptide sequence according to the following:

X11-X12-Gly-X13 (Formula (XII));

wherein X11 is selected from: His, Ala, Thr, Lys, or Glu;
wherein X12 is selected from: Ala or Thr; and
wherein X13 is selected from: Lys, Cys, or Gly; and
(b) a cargo.

In some embodiments, the targeting molecule comprises (a) a peptide sequence according to the following:

X12-Gly-X13 (Formula (XIII));

wherein X12 is selected from: Ala or Thr; and
wherein X13 is selected from: Lys, Cys, or Gly; and
(b) a cargo.

In some embodiments, the targeting molecule comprises (a) a peptide sequence according to the following:

X10-X11-X12-Gly-X13-X14 (Formula (XVI));

wherein X10 is selected from: Glu, His, Ala, Thr, or Lys;
wherein X11 is selected from: His, Ala, Thr, Lys, or Glu;
wherein X12 is selected from: Ala or Thr;
wherein X13 is selected from: Lys, Cys, or Gly; and
wherein X14 is selected from: Gly; and
(b) a cargo.

In some embodiments, the targeting molecule comprises (a) a peptide sequence according to the following:

X10-X11-X12-Gly-X13-X14-X15 (Formula (XVII));

wherein X10 is selected from: Glu, His, Ala, Thr, or Lys;
wherein X11 is selected from: His, Ala, Thr, Lys, or Glu;
wherein X12 is selected from: Ala or Thr;
wherein X13 is selected from: Lys, Cys, or Gly;
wherein X14 is selected from: Gly; and
wherein X15 is selected from: Cys; and
(b) a cargo.

In some embodiments, the targeting molecule comprises (a) a peptide sequence selected from: GLU-HIS-THR-GLY-LYS (SEQ ID NO. 1); LYS-ALA-PRO-GLU-HIS-THR-GLY-LYS (SEQ ID NO. 2); LEU-ALA-LYS-ALA-PRO-GLU-HIS-THR-GLY-LYS (SEQ ID NO. 3); GLN-THR-LEU-ALA-LYS-ALA-PRO-GLU-HIS-THR-GLY-LYS (SEQ ID NO. 4); THR-GLN-THR-LEU-ALA-LYS-ALA-PRO-GLU-HIS-THR-GLY-LYS (SEQ ID NO. 5); ASN-THR-GLN-THR-LEU-ALA-LYS-ALA-PRO-GLU-HIS-THR-GLY-LYS (SEQ ID NO. 6); ASN-THR-GLN-THR-LEU-ALA-LYS-ALA-PRO-GLU-HIS-ALA-GLY-LYS (SEQ ID NO. 7); ASN-THR-GLN-THR-LEU-ALA-LYS-ALA-PRO-GLU-ALA-THR-GLY-LYS (SEQ ID NO. 8);

ASN-THR-GLN-THR-LEU-ALA-LYS-ALA-PRO-HIS-GLU-THR-GLY-LYS (SEQ ID NO. 9); ASN-THR-GLN-THR-LEU-ALA-LYS-ALA-PRO-ALA-HIS-THR-GLY-LYS (SEQ ID NO. 10); ASN-THR-GLN-THR-LEU-ALA-LYS-ALA-PRO-LYS-HIS-THR-GLY-LYS (SEQ ID NO. 11); ASN-THR-GLN-THR-LEU-ALA-LYS-ALA-ALA-GLU-HIS-THR-GLY-LYS (SEQ ID NO. 12); ASN-THR-GLN-THR-LEU-ALA-LYS-ALA-D-PRO-GLU-HIS-THR-GLY-LYS (SEQ ID NO. 13); ASN-THR-GLN-THR-LEU-ALA-LYS-PRO-PRO-GLU-HIS-THR-GLY-LYS (SEQ ID NO. 14); ASN-THR-GLN-THR-LEU-ALA-LYS-PHE-PRO-GLU-HIS-THR-GLY-LYS (SEQ ID NO. 15); ASN-THR-GLN-THR-LEU-ALA-GLU-ALA-PRO-GLU-HIS-THR-GLY-LYS (SEQ ID NO. 16); ASN-THR-GLN-THR-LEU-HIS-GLU-ALA-PRO-GLU-HIS-THR-GLY-LYS (SEQ ID NO. 17); ASN-THR-GLN-THR-LEU-PHE-LYS-ALA-PRO-GLU-HIS-THR-GLY-LYS (SEQ ID NO. 18); ASN-THR-GLN-THR-LYS-ALA-LYS-ALA-PRO-GLU-HIS-THR-GLY-LYS (SEQ ID NO. 19); ASN-THR-GLN-ALA-LEU-ALA-LYS-ALA-PRO-GLU-HIS-THR-GLY-LYS (SEQ ID NO. 20); ASN-THR-GLU-THR-LEU-ALA-LYS-ALA-PRO-GLU-HIS-THR-GLY-LYS (SEQ ID NO. 21); ASN-THR-LYS-THR-LEU-ALA-LYS-ALA-PRO-GLU-HIS-THR-GLY-LYS (SEQ ID NO. 22); ASN-ALA-GLN-THR-LEU-ALA-LYS-ALA-PRO-GLU-HIS-THR-GLY-LYS (SEQ ID NO. 23); ALA-THR-GLN-THR-LEU-ALA-LYS-ALA-PRO-GLU-HIS-THR-GLY-LYS (SEQ ID NO. 24); PRO-GLU-HIS-THR-LEU-ALA-LYS-ALA-PRO-GLU-HIS-THR-GLY-LYS (SEQ ID NO. 25); GLU-HIS-THR-GLY-CYS (SEQ ID NO. 26); GLU-HIS-THR-GLY-GLY-GLY-CYS (SEQ ID NO. 27); LYS (SEQ ID NO. 28); GLY-LYS (SEQ ID NO. 29); THR-THR-THR-GLY-GLY-GLY-CYS (SEQ ID NO. 30); GLU-GLU-THR-GLY-GLY-GLY-CYS (SEQ ID NO. 31); LYS-HIS-THR-GLY-GLY-GLY-CYS (SEQ ID NO. 32); GLU-LYS-THR-GLY-GLY-GLY-CYS (SEQ ID NO. 33; and (b) a cargo. In some embodiments, the targeting molecule comprises: (a) a peptide sequence selected from: Gly-Lys (SEQ ID NO. 29); Thr-Thr-Thr-Gly-Gly-Gly-Cys (SEQ ID NO. 30); Glu-glu-Thr-Gly-Gly-Gly-Cys (SEQ ID NO. 31); Lys-His-Thr-Gly-Gly-Gly-Cys (SEQ ID NO. 32); Glu-Lys-Thr-Gly-Gly-Gly-Cys (SEQ ID NO. 33); and (a) a cargo. In some embodiments, the targeting molecule comprises: (a) a peptide comprising the sequence: Gly-Lys (SEQ ID NO. 29); and (b) a cargo. In some embodiments, the targeting molecule comprises: (a) a peptide comprising the sequence: Thr-Thr-Thr-Gly-Gly-Gly-Cys (SEQ ID NO. 30); and (b) a cargo. In some embodiments, the targeting molecule comprises: (a) a peptide comprising the sequence: Glu-glu-Thr-Gly-Gly-Gly-Cys (SEQ ID NO. 31); and (b) a cargo. In some embodiments, the targeting molecule comprises: (a) a peptide comprising the sequence: Lys-His-Thr-Gly-Gly-Gly-Cys (SEQ ID NO. 32); and (b) a cargo. In some embodiments, the targeting molecule comprises: (a) a peptide comprising the sequence: Glu-Lys-Thr-Gly-Gly-Gly-Cys (SEQ ID NO. 33); and (b) a cargo. In some embodiments, the targeting molecule comprises a peptide sequence sharing 80% homology with a peptide sequence disclosed herein. In some embodiments, the targeting molecule comprises a peptide sequence sharing 85% homology with a peptide sequence disclosed herein. In some embodiments, the targeting molecule comprises a peptide sequence sharing 90% homology with a peptide sequence disclosed herein. In some embodiments, the targeting molecule comprises a peptide sequence sharing 95% homology with a peptide sequence disclosed herein. In some embodiments, the targeting molecule comprises a peptide sequence sharing 99% homology with a peptide sequence disclosed herein.

The peptides of the present invention are synthesized by any suitable method. For example, targeting peptides and aptamers of the present invention can be chemically synthesized by solid phase peptide synthesis. Techniques for solid phase synthesis are described, for example, by Barany and Merrifield (1963) *Solid-Phase Peptide Synthesis*; pp. 3-284 in *The Peptides: Analysis, Synthesis, Biology.* Vol. 2: *Special Methods in Peptide Synthesis, Part A*.; Merrifield et al. (1963) *J. Am. Chem. Soc.*, 85: 2149-2156, and Stewart et al. (1984) *Solid Phase Peptide Synthesis*, 2nd ed. Pierce Chem. Co., Rockford.

Cargo

In some embodiments, the targeting molecule further comprises a cargo. In some embodiments, the peptide or aptamer is directly bound to a cargo. In some embodiments, the peptide or aptamer is indirectly (e.g., via a linker) bound to a cargo. In some embodiments, two or more peptides or aptamers are directly or indirectly bound to a cargo. In some embodiments, the cargo is a drug. In some embodiments, the cargo is a fluorescent moiety.

Drugs

In some embodiments, the targeting molecule further comprises a drug. All drugs that act on a neuron or nerve (or a component thereof) are encompassed within the term "drug." Specific examples of drug given herein, are illustrative and are not meant to limit the drugs for use with the targeting molecules disclosed herein.

In some embodiments, the targeting molecule comprises a peptide sequence that is directly bound to a drug. In some embodiments, the targeting molecule comprises a peptide sequence that is indirectly (e.g., via a linker) bound to a drug. In some embodiments, the targeting molecule comprises two or more peptide sequences that are directly or indirectly bound to a drug.

In some embodiments, the drug is selected from a drug that: induces cell death (apoptotic or necrotic), inhibits cell death (apoptotic or necrotic), inhibits the transmission of a neuron or nerve signal (i.e., an electrochemical impulse), inhibits the release of a neurotransmitter, agonizes the activity of a GABA receptor, partially or fully inhibits the repolarization of a neuron, disrupts the conduction of an ion channel, or a combination thereof.

In some embodiments, the drug is an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the drug is meclizine, diphenhydramine, dimenhydrinate, loratadine, quetiapine, mepyramine, piperoxan, antazoline, carbinoxamine, doxylamine, clemastine, pheniramine, chlorphenamine, chlorpheniramine, dexchlorpheniramine, brompheniramine, triprolidine, cyclizine, chlorcyclizine, hydroxyzine, promethazine, alimemazine, trimeprazine, cyproheptadine, azatadine, ketotifen, oxatomide, meclizine hydrochloride, promethazine hydrochloride, cinnarizine, hydroxyzine pamoate, betahistine dihydrochloride, alprazolam, bromazepam, brotizolam, chlordiazepoxide, clonazepam, clorazepate, diazepam, estazolam, flunitrazepam, flurazepam, loprazolam, lorazepam, lormetazepam, idazolam, nimetazepam, nitrazepam, oxazepam, prazepam, temazepam, triazolam, clonazepam, diazepam, lorazepam, furosemide, bumetanide, ethacrynic acid, gabapentin, pregabalin, muscimol, baclofen, amitriptyline, nortriptyline, trimipramine, fluoxetine, paroxetine, sertraline, glycopyrrolate, homatropine, scopolamine, atropine, benzocaine, carticaine, cinchocaine, cyclomethycaine, lidocaine, prilocalne, propxycaine, proparacaine, tetracaine, tocamide, trimecaine, carbamazepine, oxcarbazepine, phenylein, valproic acid, sodium valproate, cinnarizine, flunarizine, nimodipine, thyrotropin-releasing hormone, amifostine (also known as WR-2721, or ETHYOL®); a carbamate compound (e.g., 2-phenyl-1,2-ethanediol monocarbomates and dicarbamates); LY450139 (hydroxylvaleryl monobenzocaprolactam); L685458 (1S-benzyl-4R[1-[1-S-carbamoyl-2-phenethylcarbamoyl)-1S-3-methylbutylcarbamoyl]-2R-hydroxy-5-phenylpentyl}carbamic acid tert-butyl ester); LY411575 ($N^2$-[(2S)-2-(3,5-difluorophenyl)-2-hydroxyethanoyl]-$N^1$-[(7S)-5-methyl-6-oxo-6,7-dihydro-5H-dibenzo[bid]azepin-7-yl]-L-alaninamide); MK-0752; tarenflurbil; BMS-299897 (2-[(1R)-1-[[(4-chlorophenyl)sulfony](2,5-difluorophenyl)amino]ethyl]-5-fluorobenzenepropanoic acid; CNQX (6-cyano-7-nitroquinoxaline-2,3-dione); NBQX (2,3-dihydroxy-6-nitro-7-sulfamoyl-benzo[f]quinoxaline-2,3-dione); DNQX (6,7-dinitroquinoxaline-2,3-dione); kynurenic acid; 2,3-dihydroxy-6-nitro-7-sulfamoylbenzo-[f]quinoxaline; 1-aminoadamantane; dextromethorphan; dextrorphan; ibogaine; ketamine; nitrous oxide; phencyclidine; riluzole; tiletamine; memantine; dizocilpine; aptiganel; remacimide; 7-chlorokynurenate; DCKA (5,7-dichlorokynurenic acid); kynurenic acid; 1-aminocyclopropanecarboxylic acid (ACPC); AP7 (2-amino-7-phosphonoheptanoic acid); APV (R-2-amino-5-phosphonopentanoate); CPPene (3-[(R)-2-carboxypiperazin-4-yl]-prop-2-enyl-1-phosphonic acid); (+)-(1S,2S)-1-(4-hydroxy-phenyl)-2-(4-hydroxy-4-phenylpiperidino)-1-pro-panol; (1S,2S)-1-(4-hydroxy-3-methoxyphenyl)-2-(4-hydroxy-4-phenylpiperi-dino)-1-propanol; (3R,4S)-3-(4-(4-fluorophenyl)-4-hydroxypiperidin-1-yl-)-chroman-4,7-diol; (1R*,2R*)-1-(4-hydroxy-3-methylphenyl)-2-(4-(4-fluoro-phenyl)-4-hydroxypiperidin-1-yl)-propan-1-ol-mesylate); LY389795 ((−)-2-thia-4-aminobicyclo-hexane-4,6-dicarboxylate); LY379268 ((−)-2-oxa-4-aminobicyclo-hexane-4,6-dicarboxylate); LY354740 ((+)-2-aminobicyclo-hexane-2,6dicarboxylate); DCG-IV ((2S,2'R,3'R)-2-(2',3'-dicarboxycyclopropyl)glycine); 2R,4R-APDC (2R,4R-4-aminopyrrolidine-2,4-dicarboxylate); (S)-3C4HPG ((S)-3-carboxy-4-hydroxyphenylglycine); (S)-4C3HPG ((S)-4-carboxy-3-hydroxyphenylglycine); L-CCG-I ((2S,1'S,2'S)-2-(carboxycyclopropyl)glycine); ACPT-I ((1S,3R,4S)-1-aminocyclopentane-1,3,4-tricarboxylic acid); L-AP4 (L-(+)-2-Amino-4-phosphonobutyric acid); (S)-3,4-DCPG ((S)-3,4-dicarboxyphenylglycine); (RS)-3,4-DCPG ((RS)-3,4-dicarboxyphenylglycine); (RS)-4-phosphonophenylglycine ((RS)PPG); AMN082 (,N'-bis (diphenylmethyl)-1,2-ethanediamine dihydrochloride); DCG-IV ((2S,2'R,3'R)-2-(2',3'-dicarboxycyclopropyl)glycine); AMN082; brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); an aminoglycoside antibiotic (e.g., gentamicin and amikacin); a macrolide antibiotic (e.g, erythromycin); a glycopeptide antibiotic (e.g. vancomycin); salicylic acid; nicotine; Eburnamenine-14-carboxylic acid ethyl ester; sipatrigine (2-(4-Methylpiperazin-1-yl)-5-(2,3,5-trichlorophenyl)-pyrimidin-4-amine); amiloride (3,5-diamino-N-(aminoiminomethyl)-6-chloropyrazinecarboxamide hydrochloride); carbamazepine (5H-dibenzo[b,f]azepine-5-carboxamide); TTX (octahydro-12-(hydroxymethyl)-2-imino-5,9:7,10a-dimethano-10aH-[1,3]dioxocino[6,5-d]pyrimidine-4,7,10,11,12-pentol); RS100642 (1-(2,6-dimethyl-phenoxy)-2-ethylaminopropane hydrochloride); mexiletine ((1-(2,6-dimethylphenoxy)-2-aminopropane hydrochloride)); QX-314 (N-(2,6-Dimethylphenylcarbamoylmethyl)triethylammonium bromide); phenyloin (5,5-diphenylimidazolidine-2,4-dione); lamotrigine (6-(2,3-dichlorophenyl)-1,2,4-triazine-3,5-diamine); 4030W92 (2,4-diamino-5-(2,3-dichlorophenyl)-6-fluoromethylpyrimidine); BW1003C87 (5-(2,3,5-trichlorophenyl)pyrimidine-2,4-1.1 ethanesulphonate); QX-222 (2-[(2,6-dimethylphenyl)amino]-N,N,N-trimethyl-2-oxoethaniminiumchloride); ambroxol (trans-4-[[(2-Amino-3,5-dibromophenyl)methyl]amino]cyclo hexanol hydrochloride); R56865 (N-[1-(4-(4-fluorophenoxy)butyl]-4-piperidinyl-N-methyl-2-benzo-thiazolamine); lubeluzole; ajmaline((17R,21alpha)-ajmalan-17,21-diol); procainamide (4-amno-N-(2-diethylaminoethyl)benzamide hydrochloride); flecamide; riluzoleor; triamicinolone actenoide; Dexamethasone; promethazine; prochlorperazine; trimethobenzamide; triethylperazine; dolasetron; granisetron; ondansetron; tropisetron; and palonosetron; droperidol; meclizine; perphenazine; thiethyl perazine; domperidone; properidol; haloperidol; chlorpromazine; promethazine; prochlorperazine; metoclopramide; dronabinol; nabilone; sativex; scopolamine; dexamethasone; trimethobenzamine; emetrol; propofol; muscimol; acridine carboxamide; actinomycin; 17-N-allylamino-17-demethoxygeldanamycin; amsacrine; aminopterin; anthracycline; antineoplastic; antineoplaston; 5-azacytidine; azathioprine; BL22; bendamustine; biricodar; bleomycin; bortezomib; bryostatin; busulfan; calyculin; camptothecin; capecitabine; carboplatin; chlorambucil; cisplatin; cladribine; clofarabine; cytarabine; dacarbazine; dasatinib; daunorubicin; decitabine; dichloroacetic acid; discodermolide; docetaxel; doxorubicin; epirubicin; epothilone; eribulin; estramustine; etoposide; exatecan; exisulind; ferruginol; floxuridine; fludarabine; fluorouracil; fosfestrol; fotemustine; gemcitabine; hydroxyurea; IT-101; idarubicin; ifosfamide; imiquimod; irinotecan; irofulven; ixabepilone; laniquidar; lapatinib; lenalidomide; lomustine; lurtotecan; mafosfamide; masoprocol; mechlorethamine; melphalan; mercaptopurine; mitomycin; mitotane; mitoxantrone; nelarabine; nilotinib; oblimersen; oxaliplatin; PAC-1; methotrexate (RHEUMATREX®, Amethopterin); cyclophosphamide (CYTOXAN®); thalidomide (THALIDOMID®); paclitaxel; pemetrexed; pentostatin; pipobroman; pixantrone; plicamycin; procarbazine; proteasome inhibitors (e.g.; bortezomib); raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; N-acetylcysteine; vitamin E; vitamin C; vitamin A; lutein; selenium glutathione; melatonin; a polyphenol; a carotenoid; coenzyme Q-10; Ebselen (2-phenyl-1,2-benzisoselenazol-3(2H)-one (also called PZ 51 or DR3305); L-methionine; azulenyl nitrones; L-(+)-Ergothioneine; CAPE (caffeic acid phenethyl ester); dimethylthiourea; dimethylsulfoxide; disufenton sodium; pentoxifylline; MCI-186; Ambroxol; U-83836E; MitoQ (mitoquinone mesylate); Idebenone (2-(10-hydroxydecyl)-5,6-dimethoxy-3-methyl-cyclohexa-2,5-diene-1,4-dione);

desferrioxamine; hydroxybenzyl ethylene diamine; fullerenol-1, pyrrolidine dithiocarbamate; acetylcarnitine; lipoic acid; a stilbene; a chalcone; a flavone; an isoflavone; a flavanones; an anthocyanidin; a catechin; isonicotinamide; dipyridamole; ZM 336372; camptothecin; coumestrol; nor-dihydroguaiaretic acid; esculetin; SRT-1720; SRT-1460; SRT-2183; aminoguanidine; 1-Amino-2-hydroxyguanidine p-toluensulfate; GED; bromocriptine mesylate; dexamethasone; SDMA; ADMA; L-NMMA; L-NMEA; D-MMA; L-NIL; L-NNA; L-NPA; L-NAME; L-VNIO; diphenyleneiodonium chloride; 2-ethyl-2-thiopseudourea; haloperidol; L-NIO; MEG; SMT; SMTC; 7-Ni; nNOS inhibitor; 1,3-PBITU; L-thiocitrulline; TRIM; MTR-105; BBS-1; BBS-2; ONO-1714; GW273629; GW 274150; PPA250; AR-R17477; AR-R18512; spiroquinazolone; 1400W; S-NC; NTG; SNP; thapsigargin; VEGF; bradykinin; ATP; sphingosine-1-phosphate; estrogen; angiopoietin; acetylcholine; SIN-1; GEA 3162; GEA; GEA 5024; GEA 5538; SNAP; molsidomine; CNO-4; CNO-5; DEA/NO; IPA/NO; SPER/NO; SULFI/NO; OXI/NO; DETA/NO; nicorandil; minoxidil, levcromakalim; lemakalim; cromakalim; L-735,334; retigabine; flupirtine; BMS-204352; DMP-543; linopirdine; XE991; 4-AP; 3,4-DAP; E-4031; DIDS; Way 123,398; CGS-12066A; dofetilide; sotalol; apamin; amiodarone; azimilide; bretylium; clofilium; tedisamil; ibutilide; sematilide; nifekalant; tamulustoxin; ATP; ADP; UTP; UDP; UDP-glucose; adenosine; 2-MeSATP; 2-MeSADP; αβmeATP; dATPαS; ATPγS; Bz-ATP; MRS2703; denufosol tetrasodium; MRS2365; MRS 2690; PSB 0474; A-317491; RO-3 (Roche); suramin; PPADS; PPNDS; DIDS; pyridoxal-5-phosphate; 5-(3-bromophenyl)-1,3-dihydro-2H-benzofuro-[3,2-e]-1,4-diazepin-2-one; cibacron blue; basilen blue; ivermectin; A-438079; A-740003; NF023; NF449; NF110; NF157; MRS 2179; NF279; MRS 2211; MRS 2279; MRS 2500 tetrasodium salt; TNP-ATP; tetramethylpyrazine; Ip$_5$I; βγ-carboxymethylene ATP; βγ-chlorophosphomethylene ATP; KN-62; spinorphin; minocycline; SB-203580 (4-(4-Fluorophenyl)-2-(4-methylsulfinyl phenyl)-5-(4-pyridyl) 1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (5-(2-Amino-4-pyrimidinyl)-4-(4-fluorophenyl)-1-(4-piperidinlyl)imidazole); D-JNKI-1 ((D)-hJIP$_{175-157}$-DPro-DPro-(D)-HIV-TAT$_{57-48}$); AM-111 (Auris); SP600125 (anthra[1,9-cd]pyrazol-6(2H)-one); JNK Inhibitor I ((L)-HIV-TAT$_{48-57}$-PP-JBD$_{20}$); JNK Inhibitor III ((L)-HIV-TAT$_{47-57}$-gaba-c-Junδ$_{33-57}$); AS601245 (1,3-benzothiazol-2-yl (2-[[2-(3-pyridinyl)ethyl]amino]-4 pyrimidinyl)acetonitrile); JNK Inhibitor VI (H$_2$N-RPKRPTTLNLF-NH$_2$); JNK Inhibitor VIII (N-(4-Amino-5-cyano-6-ethoxypyridin-2-yl)-2-(2,5-dimethoxyphenyl)acetamide); JNK Inhibitor IX (N-(3-Cyano-4,5,6,7-tetrahydro-1-benzothien-2-yl)-1-naphthamide); dicumarol (3,3'-Methylenebis(4-hydroxycoumarin)); SC-236 (4-[5-(4-chlorophenyl)-3-(trifluoromethyl)-1H-pyrazol-1-yl]benzenesulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel blocker ((±)-1-(3, 6-Dibromocarbazol-9-yl)-3-piperazin-1-yl-propan-2-ol); Bax inhibiting peptide P5 (also known as Bax inhibitor peptide P5); Kp7-6; FAIM(S) (Fas apoptosis inhibitory molecule-short); FAIM(L) (Fas apoptosis inhibitory molecule-long); Fas:Fc; FAP-1; NOK2; F2051; F1926; F2928; ZB4; Fas M3 mAb; EGF; 740 Y-P; SC 3036 (KKHTDDGYMPM-SPGVA); PI 3-kinase Activator (Santa Cruz Biotechnology, Inc.); Pam$_3$Cys ((S)-(2,3-bis(palmitoyloxy)-(2RS)-propyl)-N-palmitoyl-(R)-Cys-(S)-Ser(S)-Lys4-OH, trihydrochloride); Act1 (NF-kB activator 1); an anti-IkB antibody; Acetyl-11-keto-b-Boswellic Acid; Andrographolide; Caffeic Acid Phenethyl Ester (CAPE); Gliotoxin; Isohelenin; NEMO-Binding Domain Binding Peptide (DRQIKIWFQNRRMK-WKKTALDWSWLQTE); NF-kB Activation Inhibitor (6-Amino-4-(4-phenoxyphenylethylamino)quinazoline); NF-kB Activation Inhibitor II (4-Methyl-N1-(3-phenylpropyl)benzene-1,2-diamine); NF-kB Activation Inhibitor III (3-Chloro-4-nitro-N-(5-nitro-2-thiazolyl)-benzamide); NF-kB Activation Inhibitor IV ((E)-2-Fluoro-4'-methoxystilbene); NF-kB Activation Inhibitor V (5-Hydroxy-(2,6-diisopropylphenyl)-1H-isoindole-1,3-dione); NF-kB SN50 (AAVALLPAVLLALLAPVQRKRQKLMP); Oridonin; Parthenolide; PPM-18 (2-Benzoylamino-1,4-naphthoquinone); Ro106-9920; Sulfasalazine; TIRAP Inhibitor Peptide (RQIKIWFNRRMKWKKLQLRDAAPGGAIVS); Withaferin A; Wogonin; BAY 11-7082 ((E)$_3$-[(4-Methylphenyl)sulfonyl]-2-propenenitrile); BAY 11-7085 ((E)3-[(4-t-Butylphenyl)sulfonyl]-2-propenenitrile); (E)-Capsaicin; Aurothiomalate (ATM or AuTM); Evodiamine; Hypoestoxide; IKK Inhibitor III (BMS-345541); IKK Inhibitor VII; IKK Inhibitor X; IKK Inhibitor II; IKK-2 Inhibitor IV; IKK-2 Inhibitor V; IKK-2 Inhibitor VI; IKK-2 Inhibitor (SC-514); IkB Kinase Inhibitor Peptide; IKK-3 Inhibitor IX; ARRY-797 (Array BioPharma); SB-220025 (5-(2-Amino-4-pyrimidinyl)-4-(4-fluorophenyl)-1-(4-piperidinlyl)imidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl)1H-imidazole); JX-401 (−[2-Methoxy-4-(methylthio)benzoyl]-4-(phenylmethyl)piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo[2,1-b]thiazole dihydrochloride); SB-200646 (N-(1-Methyl-1H-indol-5-yl)-N'-3-pylidinylurea); CMPD-1 (2'-Fluoro-N-(4-hydroxyphenyl)-[1,1'-biphenyl]-4-butanamide); EO-1428 ((2-Methylphenyl)-[4-[(2-amino-4-bromophenyl)amino]-2-chlorophenyl]methanone); SB-253080 (4-[5-(4-Fluorophenyl)-2-[4-(methylsulfonyl)phenyl]-1H-imidazol-4-yl]pyridine); SD-169 (1H-Indole-5-carboxamide); SB-203580 (4-(4-Fluorophenyl)-2-(4-methylsulfinyl phenyl)-5-(4-pyridyl) 1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1,1'-biphenyl)-4-yl)methyl)-1H-1-benzazepin-3-yl)-, (R)-); EP1572 (Aib-DTrp-DgTrp-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; piperine; hemin; brazilin; z-VAD-FMK (Benzyloxycarbonyl-Val-Ala-Asp(OMe)-fluoromethylketone); z-LEHD-FMK (benzyloxycarbonyl-Leu-Glu(OMe)-His-Asp(OMe)-fluoromethylketone); B-D-FMK (boc-aspartyl(Ome)-fluoromethylketone); Ac-LEHD-CHO (N-acetyl-Leu-Glu-His-Asp-CHO); Ac-IETD-CHO(N-acetyl-Ile-Glu-Thr-Asp-CHO); z-IETD-FMK (benzyloxycarbonyl-Ile-Glu(OMe)-Thr-Asp(OMe)-fluoromethylketone); FAM-LEHD-FMK (benzyloxycarbonyl Leu-Glu-His-Asp-fluoromethyl ketone); FAM-LETD-FMK (benzyloxycarbonyl Leu-Glu- Thr-Asp-fluoromethyl ketone); Q-VD-OPH (Quinoline-Val-Asp-CH$_2$—O-Ph); XIAP; cIAP-1; cIAP-2; ML-IAP; ILP-2; NAIP; Survivin; Bruce; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-[(phenylmethoxy)carbonyl]-L-leucyl-N-[(1S)-1-formyl-3-methylbutyl]-L-leucinamide); MYODUR; BN 82270 (Ipsen); BN 2204 (Ipsen); AHLi-11 (Quark Pharmaceuticals), an mdm2 protein, pifithrin-α (1-(4-Methylphenyl)-2-(4,5,6,7-tetrahydro-2-imino-3(2H)-benzothiazolyl)ethanone); trans-stilbene; cis-stilbene; resveratrol; piceatannol; rhapontin; deoxyrhapontin; butein; chalcon; isoliquirtigen; butein; 4,2',4'-trihydroxychalcone; 3,4,2',4',6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.H2O); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol.2HCl); β-1'-5-methyl-nicotinamide-2'-deoxyribose; β-D-1'-5-methyl-nicotinamide-2'-deoxyribofuranoside; β-1'-4,5-dimethyl-nicotinamide-2'-deoxyribose; β-D-1'-4,5-dimethyl-nicotinamide-2'-deoxyribofuranoside; 1-Naphthyl PP1 (1-(1,1-Dimethylethyl)-3-(1-naphthalenyl)-1H-pyrazolo[3,4-d] pyrimidin-4-amine); Lavendustin A (5-[[(2,5-Dihydroxyphenyl)methyl][(2-hydroxyphenyl)methyl] amino]-2-hydroxybenzoic acid); MNS (3,4-Methylenedioxy-b-nitrostyrene); PP1 (1-(1,1-Dimethylethyl)-1-(4-methylphenyl)-1H-pyrazolo[3,4-d] pyrimidin-4-amine); PP2 (3-(4-chlorophenyl) 1-(1,1-dimethylethyl)-1H-pyrazolo[3,4-d]pyrimidin-4-amine); KX1-004 (Kinex); KX1-005 (Kinex); KX1-136 (Kinex); KX1-174 (Kinex); KX1-141 (Kinex); KX2-328 (Kinex); KX1-306 (Kinex); KX1-329 (Kinex); KX2-391 (Kinex); KX2-377 (Kinex); ZD4190 (Astra Zeneca; N-(4-bromo-2-fluorophenyl)-6-methoxy-7-(2-(1H-1,2,3-triazol-1-yl) ethoxy)quinazolin-4-amine); AP22408 (Ariad Pharmaceuticals); AP23236 (Ariad Pharmaceuticals); AP23451 (Ariad Pharmaceuticals); AP23464 (Ariad Pharmaceuticals); AZD0530 (Astra Zeneca); AZM475271 (M475271; Astra Zeneca); Dasatinib (N-(2-chloro-6-methylphenyl)-2-(6-(4-(2-hydroxyethyl)-piperazin-1-yl)-2-methylpyrimidin-4-ylamino) thiazole-5-carboxamide); GN963 (trans-4-(6,7-dimethoxyquinoxalin-2-ylamino)cyclohexanol sulfate); Bosutinib (4-((2,4-dichloro-5-methoxyphenyl)amino)-6-methoxy-7-(3-(4-methyl-1-piperazinyl)propoxy)-3-quinolinecarbonitrile); or combinations thereof.

Imaging Agents

In some embodiments, the targeting molecule further comprises an imaging agent. All imaging agents are encompassed within the term "imaging agent." Specific examples of imaging agents given herein, are illustrative and are not meant to limit the imaging agents for use with the targeting molecules disclosed herein.

In some embodiments, the targeting molecule comprises a peptide sequence that is directly bound to an imaging agent. In some embodiments, the targeting molecule comprises a peptide sequence that is indirectly (e.g., via a linker) bound to an imaging agent. In some embodiments, the targeting molecule comprises two or more peptide sequences that are directly or indirectly bound to an imaging agent.

In some embodiments, the imaging agent is a dye. In some embodiments, the imaging agent is a fluorescent moiety. In some embodiments, the fluorescent moiety is selected from: a fluorescent protein, a fluorescent peptide, a fluorescent dye, a fluorescent material or a combination thereof.

All fluorescent moieties are encompassed within the term "fluorescent moiety." Specific examples of fluorescent moieties given herein are illustrative and are not meant to limit the fluorescent moieties for use with the targeting molecules disclosed herein.

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes.

Examples of fluorescein dyes include, but are not limited to, 5-carboxyfluorescein, fluorescein-5-isothiocyanate, fluorescein-6-isothiocyanate and 6-carboxyfluorescein.

Examples of rhodamine dyes include, but are not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®).

In some embodiments, the imaging agent is a xanthenes dye.

In some embodiments, the imaging agent is an indocarbocyanin dye. Examples of indocarbocyanine dyes include, but are not limited to, Cy3, Cy3B, Cy3.5, Cy5, Cy5.5, Cy7, DyLight650, IRDYE680, DyLight750, Alexa Fluor 647, Alexa Fluor 750, IR800CW, ICG. In some embodiments, the imaging agent is Cy5.

Examples of fluorescent peptides include GFP (Green Fluorescent Protein) or derivatives of GFP (e.g., EBFP, EBFP2, Azurite, mKalama1, ECFP, Cerulean, CyPet, YFP, Citrine, Venus, YPet).

In some embodiments, the fluorescent moiety is a peptide. In some embodiments, the fluorescent moiety is Green Fluorescent Protein (GFP). In some embodiments, the fluorescent moiety is a derivative of GFP (e.g., EBFP, EBFP2, Azurite, mKalama1, ECFP, Cerulean, CyPet, YFP, Citrine, Venus, YPet).

Fluorescent labels are detected by any suitable method. For example, a fluorescent label may be detected by exciting the fluorochrome with the appropriate wavelength of light and detecting the resulting fluorescence, e.g., by microscopy, visual inspection, via photographic film, by the use of electronic detectors such as charge coupled devices (CCDs), photomultipliers, etc.

In some embodiments, the imaging agent is labeled with a positron-emitting isotope (e.g., $^{18}$F) for positron emission tomography (PET). In some embodiments, the imaging agent is labeled with a gamma-ray isotope (e.g., $^{99m}$Tc) for single photon emission computed tomography (SPECT). In some embodiments, the imaging agent is labeled with a paramagnetic molecule or nanoparticle (e.g., $Gd^{3+}$ chelate or coated magnetite nanoparticle) for magnetic resonance imaging (MRI).

In some embodiments, the imaging agent is labeled with: a radionuclide chelate, an iron oxide particle, a super paramagnetic iron oxide particle, an ultra small paramagnetic particle, a manganese chelate or gallium containing agent.

Examples of radionuclide chelates include, but are not limited to diethylene triamine pentaacetic acid (DTPA); 1,4,7,10-tetraazacyclododecane-1,4,7,10-tetraacetic acid (DOTA); 6-Hydrazinopyridine-3-carboxylic acid (HYNIC); and 1,4,7-triazacyclononane-N,N',N''-triacetic acid (NOTA).

In some embodiments, the imaging agent is a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound.

In some embodiments, the imaging agent is a nuclear probe. In some embodiments, the imaging agent is a SPECT or PET radionuclide probe. In some embodiments, the radionuclide probe is selected from: a technetium chelate, a copper chelate, a radioactive fluorine, a radioactive iodine, a indiuim chelate.

Examples of Tc chelates include, but are not limited to HYNIC, DTPA, and DOTA.

In some embodiments, the imaging agent is a radionuclide, for example $^{99m}$Tc, $^{64}$Cu, $^{18}$F, $^{124}$I, $^{111}$In, or a combination hereof.

In some embodiments, the imaging agent is $^{211}$At, $^{131}$I, $^{125}$I, $^{90}$Y, $^{186}$Re, $^{188}$Re, $^{153}$Sm, $^{212}$Bi, $^{32}$P, $^{64}$Cu radioactive isotopes of Lu, and others.

In some embodiments, the imaging agent is conjugated to high molecular weight molecule, such as water soluble polymers including, but not limited to, dextran, polyethylene glycol (PEG), serum albumin, or poly(amidoamine) dendrimer.

Linkers

In some embodiments, a cargo (e.g., a fluorescent moiety or drug) is directly attached to the targeting molecule, e.g. at the end of a peptide sequence. Alternatively, in some embodiments, a cargo (e.g., a fluorescent moiety or drug) is indirectly attached to a targeting molecule disclosed herein (e.g., via a linker).

As used herein, a "linker" is any molecule capable of binding (e.g., covalently) to a targeting molecule disclosed herein. Linkers include, but are not limited to, straight or branched-chain carbon linkers, heterocyclic carbon linkers, peptide linkers, and polyether linkers. For example, poly(ethylene glycol) linkers are available from Quanta Biodesign, Powell, Ohio. These linkers optionally have amide linkages, sulfhydryl linkages, or heterofunctional linkages.

In some embodiments, the linker binds to a targeting molecule disclosed herein by a covalent linkage. In some embodiments, the covalent linkage comprises an ether bond, thioether bond, amine bond, amide bond, oxime bond, hydrazone, carbon-carbon bond, carbon-nitrogen bond, carbon-oxygen bond, or carbon-sulfur bond.

In some embodiments, the linker is flexible. In some embodiments, the linker is rigid.

In some embodiments, the linker comprises a linear structure. In some embodiments, the linker comprises a non-linear structure. In some embodiments, the linker comprises a branched structure. In some embodiments, the linker comprises a cyclic structure.

In some embodiments, the linker is an alkyl. In some embodiments, the linker is heteroalkyl.

In some embodiments, the linker is an alkylene. In some embodiments, the linker is an alkenylene. In some embodiments, the linker is an alkynylene. In some embodiments, the linker is a heteroalkylene.

An "alkyl" group refers to an aliphatic hydrocarbon group. The alkyl moiety may be a saturated alkyl or an unsaturated alkyl. Depending on the structure, an alkyl group can be a monoradical or a diradical (i.e., an alkylene group).

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 6 carbon atoms. The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from: methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, and the like.

In some embodiments, the linker comprises a ring structure (e.g., an aryl). As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyl groups include groups having from 3 to 10 ring atoms. Cycloalkyls include, but are not limited to, cyclopropyl, cyclobutyl, cyclopentyl, cyclohexyl, cycloheptyl, and cyclooctyl.

In some embodiments, the ring is a cycloalkane. In some embodiments, the ring is a cycloalkene.

In some embodiments, the ring is an aromatic ring. The term "aromatic" refers to a planar ring having a delocalized π-electron system containing $4n+2\pi$ electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

In some embodiments, the ring is a heterocycle. The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

In some embodiments, the ring is fused. The term "fused" refers to structures in which two or more rings share one or more bonds. In some embodiments, the ring is a dimer. In some embodiments, the ring is a trimer. In some embodiments, the ring is a substituted.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e., a heteroatom). Heterocycle includes heteroaryl and heterocycloalkyl. Carbocycles and heterocycles can be optionally substituted.

In some embodiments, the linker is substituted. The term "optionally substituted" or "substituted" means that the referenced group may be substituted with one or more additional group(s) individually and independently selected from $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_8$acyloxy, nitro, $C_1$-$C_6$haloalkyl, $C_1$-$C_6$-fluoroalkyl, and amino, including $C_1$-$C_6$alkylamino, and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(=O)—, —C(=O)NH—, S(=O)$_2$NH—, —NHS(=O)$_2$—, —OC(=O)NH—, —NHC(=O)O—, —($C_1$-$C_6$alkyl)-, or —($C_2$-$C_6$alkenyl)-; and each $R^s$ is independently selected from H, ($C_1$-$C_4$alkyl), ($C_3$-$C_8$cycloalkyl), heteroaryl, aryl, and $C_1$-$C_6$heteroalkyl. Optionally substituted non-aromatic groups may be substituted with one or more oxo (=O). The protecting groups that may form the protective derivatives of the above substituents are known to those of skill in the art.

In some embodiments, a bifunctional linker having one functional group reactive with a group on one molecule (e.g., a targeting molecule), and another group reactive on the other molecule (e.g., a fluorescent moiety or a drug), is used to form the desired conjugate. Alternatively, in some embodiments, derivatization is performed to provide functional groups. Thus, for example, procedures for the generation of free sulfhydryl groups on peptides are also known (See U.S. Pat. No. 4,659,839). A linker may alternatively comprise a heterobifunctional crosslinker comprising two or more different reactive groups that form a heterocyclic ring that can interact with a targeting molecule. For example, a heterobifunctional crosslinker such as cysteine may comprise an amine reactive group and a thiol-reactive group can interact with an aldehyde on a derivatized targeting molecule. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups.

In some embodiments, a peptide linker consisting of one or more amino acids is used to join the targeting molecule and a fluorescent moiety or drug. Generally the peptide linker will have no specific biological activity other than to join the molecules or to preserve some minimum distance or other spatial relationship between them. However, the constituent amino acids of the linker may be selected to influence some property of the molecule such as the folding, net charge, or hydrophobicity. In some embodiments the peptide linker is relatively short, typically less than about 10 amino acids, preferably less than about 8 amino acids and more preferably less than 5 amino acids. Non-limiting illustrative examples include glycine and glycine-serine linkers which can be added to the C-terminus of a targeting peptide.

Further Modifications

In some embodiments, the targeting molecules of the present invention are optionally conjugated to high molecular weight molecules that increase the multivalency and avidity of labeling. In some embodiments, the high molecular weight molecules are water-soluble polymers. Examples of suitable water-soluble polymers include, but are not limited to, peptides, saccharides, poly(vinyls), poly(ethers), poly(amines), poly(carboxylic acids) and the like. In some embodiments, the water-soluble polymer is dextran, polyethylene glycol (PEG), polyoxyalkylene, polysialic acid, starch, or hydroxyethyl starch. Any suitable method is used to conjugate peptides to water-soluble polymers (see Hermanson G., *Bioconjugate Techniques* $2^{nd}$ Ed, Academic Press, Inc. 2008).

In some embodiments, the targeting molecules of the present invention are conjugated to factors having neurotrophic properties (e.g., neurotrophic proteins such as nerve growth factor (NGF), brain-derived neurotrophic factor (BDNF), neurotrophin-3 (NT-3), neurotrophin-4 (NT-4), glial cell line-derived neurotrophic factor (GDNF), ciliary neurotrophic factor (CNTF) as well as non-protein small molecules with neurotrophic properties).

Methods of Use

Labeling

Disclosed herein, in certain embodiments, are methods of labeling neurons, nerves, or tissues (e.g., the sinoatrial node and the atrioventricular node) or structures associated therewith (e.g., neuromuscular junctions) by contacting the neurons, nerves, or tissues (e.g., the sinoatrial node and the atrioventricular node) or structures associated therewith (e.g., neuromuscular junctions) with a targeting molecule described herein.

In some embodiments, the contacting occurs in vivo. In some embodiments, the contacting occurs in vitro.

In some embodiments, the neurons, nerves, or tissues (e.g., the sinoatrial node and the atrioventricular node) or structures associated therewith (e.g., neuromuscular junctions) are labeled for identification during surgery. In some embodiments, the method comprises administering a targeting molecule disclosed herein to a subject that will undergo surgery. In some embodiments, the method comprises administering a targeting molecule disclosed herein to a subject that is undergoing surgery. In some embodiments, a targeting molecule disclosed herein is administered to a patient systemically. In some embodiments, a targeting molecule disclosed herein is administered to a patient locally.

Drug Delivery

Disclosed herein, in certain embodiments, are methods of targeted drug delivery. In some embodiments, a targeting molecule disclosed herein delivers a drug to a specific target. In some embodiments, a targeting molecule disclosed herein delivers a drug to a neuron, nerve, or tissue (e.g., the sinoatrial or atrioventricular nodes) or structure (e.g., neuromuscular junction) associated therewith.

In some embodiments, the drug is an agent that reduces pain (either the perception of pain or activity of a painful stimulant). In some embodiments, the drug is an anesthetic. In some embodiments, the drug is benzocaine; carticaine; cinchocaine; cyclomethycaine; lidocaine; prilocalne; propxycaine; proparacaine; tetracaine; tocamide; and trimecaine; or a combination thereof.

In some embodiments, the drug is an agent that modulates death (e.g., via apoptosis or necrosis) of a neuron or nerve. In some embodiments, the drug is a cytotoxic agent. In some embodiments, the drug is methotrexate (RHEUMATREX®, Amethopterin); cyclophosphamide (CYTOXAN®); thalidomide (THALIDOMID®); paclitaxel; pemetrexed; pentostatin; pipobroman; pixantrone; plicamycin; procarbazine; proteasome inhibitors (e.g.; bortezomib); raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; or a combination thereof. In some embodiments, the drug is a pro-apoptotic agent. In some embodiments, the drug is an anti-apoptotic agent. In some embodiments, the drug is selected from: minocycline; SB-203580 (4-(4-Fluorophenyl)-2-(4-methylsulfinyl phenyl)-5-(4-pyridyl) 1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (5-(2-Amino-4-pyrimidinyl)-4-(4-fluorophenyl)-1-(4-piperidinlyl)imidazole); D-JNKI-1 ((D)-hJIP$_{175-157}$-DPro-DPro-(D)-HIV-TAT$_{57-48}$); AM-111 (Auris); SP600125 (anthra[1,9-cd]pyrazol-6(2H)-one); JNK Inhibitor I ((L)-HIV-TAT$_{48-57}$-PP-JBD$_{20}$); JNK Inhibitor III ((L)-HIV-TAT$_{47-57}$-gaba-c-Junδ$_{33-57}$); AS601245 (1,3-benzothiazol-2-yl (2-[[2-(3-pyridinyl)ethyl]amino]-4-pyrimidinyl)acetonitrile); JNK Inhibitor VI (H$_2$N-RPKRPTTLNLF-NH$_2$); JNK Inhibitor VIII (N-(4-Amino-5-cyano-6-ethoxypyridin-2-yl)-2-(2,5-dimethoxyphenyl)acetamide); JNK Inhibitor IX (N-(3-Cyano-4,5,6,7-tetrahydro-1-benzothien-2-yl)-1-naphthamide); dicumarol (3,3'-Methylenebis(4-hydroxycoumarin)); SC-236 (4-[5-(4-chlorophenyl)-3-(trifluoromethyl)-1H-pyrazol-1-yl]benzenesulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel blocker ((±)-1-(3, 6-Dibromocarbazol-9-yl)-3-piperazin-1-yl-propan-2-ol); Bax inhibiting peptide P5 (also known as Bax inhibitor peptide P5); Kp7-6; FAIM(S) (Fas apoptosis inhibitory molecule-short); FAIM(L) (Fas apoptosis inhibitory molecule-long); Fas:Fc; FAP-1; NOK2; F2051; F1926; F2928; ZB4; Fas M3 mAb; EGF; 740 Y-P; SC 3036 (KKHTDDGYMPM-SPGVA); PI 3-kinase Activator (Santa Cruz Biotechnology, Inc.); Pam$_3$Cys ((S)-(2,3-bis(palmitoyloxy)-(2RS)-propyl)-N-palmitoyl-(R)-Cys-(S)-Ser(S)-Lys4-OH, trihydrochloride); Act1 (NF-kB activator 1); an anti-IkB antibody; Acetyl-1'-keto-b-Boswellic Acid; Andrographolide; Caffeic Acid Phenethyl Ester (CAPE); Gliotoxin; Isohelenin; NEMO-Binding Domain Binding Peptide (DRQIKIWFQNRRMK-WKKTALDWSWLQTE); NF-kB Activation Inhibitor (6-Amino-4-(4-phenoxyphenylethylamino)quinazoline); NF-kB Activation Inhibitor II (4-Methyl-N1-(3-phenylpropyl)benzene-1,2-diamine); NF-kB Activation Inhibitor III (3-Chloro-4-nitro-N-(5-nitro-2-thiazolyl)-benzamide); NF-kB Activation Inhibitor IV ((E)-2-Fluoro-4'-methoxystilbene); NF-kB Activation Inhibitor V (5-Hydroxy-(2,6-diisopropylphenyl)-1H-isoindole-1,3-dione); NF-kB SN50 (AAVALLPAVLLALLAPVQRKRQKLMP); Oridonin; Parthenolide; PPM-18 (2-Benzoylamino-1,4-naphthoquinone); Ro106-9920; Sulfasalazine; TIRAP Inhibitor Peptide (RQIKIWFNRRMKWKKLQLRDAAPGGAIVS); Withaferin A; Wogonin; BAY 11-7082 ((E)3-[(4-Methylphenyl) sulfonyl]-2-propenenitrile); BAY 11-7085 ((E)3-[(4-t-Butylphenyl)sulfonyl]-2-propenenitrile); (E)-Capsaicin; Aurothiomalate (ATM or AuTM); Evodiamine; Hypoestoxide; IKK Inhibitor III (BMS-345541); IKK Inhibitor VII; IKK Inhibitor X; IKK Inhibitor II; IKK-2 Inhibitor IV; IKK-2 Inhibitor V; IKK-2 Inhibitor VI; IKK-2 Inhibitor (SC-514); IkB Kinase Inhibitor Peptide; IKK-3 Inhibitor IX; ARRY-797 (Array BioPharma); SB-220025 (5-(2-Amino-4-pyrimidinyl)-4-(4-fluorophenyl)-1-(4-piperidinlyl)imidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl)1H-imidazole); JX-401 (–[2-Methoxy-4-(methylthio)benzoyl]-4-(phenylmethyl)piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo[2,1-b]thiazole dihydrochloride); SB-200646 (N-(1-Methyl-1H-indol-5-yl)-N'-3-pyridinylurea); CMPD-1 (2'-Fluoro-N-(4-hydroxyphenyl)-[1,1'-biphenyl]-4-butanamide); EO-1428 ((2-Methylphenyl)-[4-[(2-amino-4-bromophenyl)amino]-2-chlorophenyl]methanone); SB-253080 (4-[5-(4-Fluorophenyl)-2-[4-(methylsulfonyl)phenyl]-1H-imidazol-4-yl]pyridine); SD-169 (1H-Indole-5-carboxamide); SB-203580 (4-(4-Fluorophenyl)-2-(4-methylsulfinyl phenyl)-5-(4-pyridyl) 1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1,1'-biphenyl)-4-yl)methyl)-1H-1-benzazepin-3-yl)-, (R)-); EP1572 (Aib-DTrp-DgTrp-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; piperine; hemin; brazilin; z-VAD-FMK (Benzyloxycarbonyl-Val-Ala-Asp(OMe)-fluoromethylketone); z-LEHD-FMK (benzyloxycarbonyl-Leu-Glu(OMe)-His-Asp(OMe)-fluoromethylketone); B-D-FMK (boc-aspartyl(OMe)-fluoromethylketone); Ac-LEHD-CHO (N-acetyl-Leu-Glu-His-Asp-CHO); Ac-IETD-CHO(N-acetyl-Ile-Glu-Thr-Asp-CHO); z-IETD-FMK (benzyloxycarbonyl-Ile-Glu(OMe)-Thr-Asp(OMe)-fluoromethylketone); FAM-LEHD-FMK (benzyloxycarbonyl Leu-Glu-His-Asp-fluoromethyl ketone); FAM-LETD-FMK (benzyloxycarbonyl Leu-Glu-Thr-Asp-fluoromethyl ketone); Q-VD-OPH (Quinoline-Val-Asp-CH$_2$—O-Ph); XIAP; cIAP-1; cIAP-2; ML-IAP; ILP-2; NAIP; Survivin; Bruce; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-[(phenylmethoxy)carbonyl]-L-leucyl-N-[(1S)-1-formyl-3-methylbutyl]-L-leucinamide); MYODUR; BN 82270 (Ipsen); BN 2204 (Ipsen); AHLi-11 (Quark Pharmaceuticals), an mdm2 protein, pifithrin-α (1-(4-Methylphenyl)-2-(4,5,6,7-tetrahydro-2-imino-3(2H)-benzothiazolyl)ethanone); trans-stilbene; cis-stilbene; resveratrol; piceatannol; rhapontin; deoxyrhapontin; butein; chalcon; isoliquirtigen; butein; 4,2',4'-trihydroxychalcone; 3,4,2',4',6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole-4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.H2O); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol.2HCl); β-1'-5-methyl-nicotinamide-2'-deoxyribose; β-D-1'-5-methyl-nicotinamide-2'-deoxyribofuranoside; β-1'-4,5-dimethyl-nicotinamide-2'-deoxyribose; β-D-1'-4,5-dimethyl-nicotinamide-2'-deoxyribofuranoside; 1-Naphthyl PP1 (1-(1,1-Dimethylethyl)-3-(1-naphthalenyl)-1H-pyrazolo[3,4-d]pyrimidin-4-amine); Lavendustin A (5-[[(2,5-Dihydroxyphenyl)methyl][(2-hydroxyphenyl)methyl]amino]-2-hydroxybenzoic acid); MNS (3,4-Methylenedioxy-b-nitrostyrene); PP1 (1-(1,1-Dimethylethyl)-1-(4-methylphenyl)-1H-pyrazolo[3,4-d]pyrimidin-4-amine); PP2 (3-(4-chlorophenyl) 1-(1,1-dimethylethyl)-1H-pyrazolo[3,4-d]pyrimidin-4-amine); KX1-004 (Kinex); KX1-005 (Kinex); KX1-136 (Kinex); KX1-174 (Kinex); KX1-141 (Kinex); KX2-328 (Kinex); KX1-306 (Kinex); KX1-329 (Kinex); KX2-391 (Kinex); KX2-377 (Kinex); ZD4190 (Astra Zeneca; N-(4-bromo-2-fluorophenyl)-6-methoxy-7-(2-(1H-1,2,3-triazol-1-yl)ethoxy)quinazolin-4-amine); AP22408 (Ariad Pharmaceuticals); AP23236 (Ariad Pharmaceuticals); AP23451 (Ariad Pharmaceuticals); AP23464 (Ariad Pharmaceuticals); AZD0530 (Astra Zeneca); AZM475271 (M475271; Astra Zeneca); Dasatinib (N-(2-chloro-6-methylphenyl)-2-(6-(4-(2-hydroxyethyl)-piperazin-1-yl)-2-methylpyrimidin-4-ylamino)thiazole-5-carboxamide); GN963 (trans-4-(6,7-dimethoxyquinoxalin-2ylamino)cyclohexanol sulfate); Bosutinib (4-((2,4-dichloro-5-methoxyphenyl)amino)-6-methoxy-7-(3-(4-methyl-1-piperazinyl)propoxy)-3-quinolinecarbonitrile); or combinations thereof.

In some embodiments, the drug is an agent that reduces undesired neuron or nerve impulses. In some embodiments, the drug reduces one or more symptoms of dyskinesia or synkinesia. In some embodiments, the drug is carbamazepine, oxcarbazepine, phenylein, valproic acid, sodium valproate, cinnarizine, flunarizine, or nimodipine, or combinations thereof.

In some embodiments, the drug is an agent that promotes regeneration of neuron or nerve tissue. In some embodiments, the drug is a growth factor. In some embodiments, the drug is selected from: brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); or a combination thereof.

Pharmaceutical Compositions

Disclosed herein, in certain embodiments, are pharmaceutical compositions comprising a targeting molecule disclosed herein. The term "pharmaceutical compositions" encompasses both compositions for therapeutic use and compositions for non-therapeutic use (e.g., for diagnostic uses). Pharmaceutical compositions herein are formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

In certain embodiments, a pharmaceutical composition disclosed herein further comprises a pharmaceutically acceptable diluent(s), excipient(s), or carrier(s). In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

In certain embodiments, a pharmaceutical composition disclosed herein is administered to a subject by any suitable administration route, including but not limited to, parenteral (intravenous, subcutaneous, intraperitoneal, intramuscular, intravascular, intrathecal, intravitreal, infusion, or local) administration.

Formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent is optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

In some embodiments, the pharmaceutical composition described herein is in unit dosage forms suitable for single administration of precise dosages. In unit dosage form, the formulation is divided into unit doses containing appropriate quantities of an active agent disclosed herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

EXAMPLES

Peptide syntheses were carried out under standard Fmoc solid phase peptide synthesis conditions. Unless otherwise stated, side chain protecting groups for the amino acids are: t-butyl for Asp, Glu, Ser, Thr, Tyr; trityl for Asn, Cys, Gln, His and Boc for Lys.

Protected amino acids were generally coupled using 4 equivalents of the amino acid, 4 equivalents of HBTU, 5 equivalents of HOBt and 10 equivalents of DIEA in DMF. Fmoc protecting groups were removed using 20% piperidine/DMF. Kaiser tests were used to monitor the progress of couplings and deprotections. Peptides were cleaved off from the resin using TFA/m-cresol/thioanisol/H2O/TIS (91/3/3/1.5/1.5, v/v). After the solvents were removed by evaporation, crude peptides were precipitated by adding cold diethyl ether.

All materials were purified by reverse-phase HPLC. The mobile phase consisted of a water (0.05 TFA) (solvent A)/acetonitrile (0.05% TFA) (solvent B) gradient with a 4 mL/min flow rate. The desired RP-HPLC fractions were combined and lyophilized. An LC-MS with an analytical column was used to identify and assess purity of the final products.

Example 1

Preparation of 6-Carboxylfluorescein (6-FAM) Labeled Peptides

Fmoc-Lys(Mtt)-OH was first coupled to the resin. The Mtt protecting group was then removed by a solution of TIS/TFA/DCM (3:3:94, v/v) in 30 min. 6-Carboxylfluorescein was coupled to lysine's ε-amine at standard solid phase peptide synthesis conditions. The resin was treated with TrtCl (20 equivalents) and DIEA (23 equivalents) in dichloromethane for 20 h to protect the phenolic hydroxyl group (2).

The remaining sequences were synthesized using solid phase peptide synthesis employing Fmoc chemistry.

Example 2

Preparation of Cy5 Labeled Peptides

The mixture of Cy5 Mono Maleimide and the peptide with a free cysteine residue (1.2 equivalents) in PBS-EDTA buffer (137 mM NaCl, 7 mM Na2HPO4, 3 mM KCl, 1.4 mM K3PO4, 4 mM EDTA, pH 7.4) was incubated at room temperature for 1 h.

The fluorescently labeled product was purified by HPLC.

Example 3

Mass Spectra of Fluorescently Labeled Peptides

Ac-Ser-His-Ser-Asn-Thr-Gln-Thr-Leu-Ala-Lys-Ala-Pro-Glu-His-Thr-Gly-Lys(6FAM)-NH2 A Calculated: [M+2H]2+ (C98H136N26O33) m/z=1104. Found ESI: [M+2H]2+ (C98H136N26O33) m/z=1104.

Ac-Ser-His-Ser-Asn-Thr-Gln-Thr-Leu-Ala-Lys-Ala-Pro-Glu-His-Thr-Gly-Cys(Cy5)-NH2 B Calculated: [M+2H]2+ (C113H163N29O36S3) m/z=1301. Found ESI: [M+2H]2+ (C113H163N29O36S3) m/z=1301.

H2N-Lys(6FAM)-NH2 1 Calculated: [M+H]+ (C27H25N3O7) m/z=505. Found ESI: [M+H]+ (C27H25N3O7) m/z=505.

Ac-Gly-Lys(6FAM)-NH2 2 Calculated: [M+H]+ (C31H30N4O9) m/z=603. Found ESI: [M+H]+ (C31H30N4O9) m/z=603.

Ac-Glu-His-Thr-Gly-Lys(6FAM)-NH2 3 Calculated: [M+H]+ (C46H51N9O15) m/z=970. Found ESI: [M+H]+ (C46H51N9O15) m/z=970.

Ac-Lys-Ala-Pro-Glu-His-Thr-Gly-Lys(6FAM)-NH2 4 Calculated: [M+H]+ (C60H75N13O18) m/z=1266. Found ESI: [M+H]+ (C60H75N13O18) m/z=1266.

Ac-Leu-Ala-Lys-Ala-Pro-Glu-His-Thr-Gly-Lys(6FAM)-NH2 5 Calculated: [M+H]+ (C69H91N15O20) m/z=1450. Found ESI: [M+H]+ (C69H91N15O20) m/z=1450.

Ac-Gln-Thr-Leu-Ala-Lys-Ala-Pro-Glu-His-Thr-Gly-Lys(6FAM)-NH2 6 Calculated: [M+2H]2+ (C78H106N18O24) m/z=841. Found ESI: [M+2H]2+ (C78H106N18O24) m/z=841.

Ac-Thr-Gln-Thr-Leu-Ala-Lys-Ala-Pro-Glu-His-Thr-Gly-Lys(6FAM)-NH2 7 Calculated: [M+H]+ (C82H113N19O26) m/z=1781. Found ESI: [M+H]+ (C82H113N19O26) m/z=1781.

AC-ASN-THR-GLN-THR-LEU-ALA-LYS-ALA-PRO-GLU-HIS-THR-GLY-LYS(6FAM)-NH2 8 Calculated: $[M+2H]^{2+}$ $(C_{86}H_{119}N_{21}O_{28})$ M/Z=948; FOUND ESI: $[M+2H]^{2+}$ $(C_{86}H_{119}N_{21}O_{28})$ M/Z=948.

Ac-Asn-Thr-Gln-Thr-Leu-Ala-Lys-Ala-Pro-Glu-His-Ala-Gly-Lys(6FAM)-NH2 9 Calculated: [M+2H]2+ (C85H117N21O27) m/z=933. Found ESI: [M+2H]2+ (C85H117N21O27) m/z=933.

Ac-Asn-Thr-Gln-Thr-Leu-Ala-Lys-Ala-Pro-Glu-Ala-Thr-Gly-Lys(6FAM)-NH2 10 Calculated: [M+2H]2+ (C83H117N19O28) m/z=915. Found ESI: [[M+2H]2+ (C83H117N19O28) m/z=915.

Ac-Asn-Thr-Gln-Thr-Leu-Ala-Lys-Ala-Pro-His-Glu-Thr-Gly-Lys(6FAM)-NH2 11 Calculated: [M+2H]2+ (C86H119N21O28) m/z=948. Found ESI: [M+2H]2+ (C86H119N21O28) m/z=948.

Ac-Asn-Thr-Gln-Thr-Leu-Ala-Lys-Ala-Pro-Ala-His-Thr-Gly-Lys(6FAM)-NH2 12 Calculated: [M+2H]2+ (C84H117N21O26) m/z=920. Found ESI: [M+2H]2+ (C84H117N21O26) m/z=920.

Ac-Asn-Thr-Gln-Thr-Leu-Ala-Lys-Ala-Pro-Lys-His-Thr-Gly-Lys(6FAM)-NH2 13 Calculated: [M+2H]2+ (C87H124N22O26) m/z=948. Found ESI: [M+2H]2+ (C87H124N22O26) m/z=948.

Ac-Asn-Thr-Gln-Thr-Leu-Ala-Lys-Ala-Ala-Glu-His-Thr-Gly-Lys(6FAM)-NH2 14 Calculated: [M+2H]2+ (C84H117N21O28) m/z=935. Found ESI: [M+2H]2+ (C84H117N21O28) m/z=935.

Ac-Asn-Thr-Gln-Thr-Leu-Ala-Lys-Ala-D-pro-Glu-His-Thr-Gly-Lys(6FAM)-NH2 15 Calculated: [M+2H]2+ (C86H119N21O28) m/z=948. Found ESI: [M+2H]2+ (C86H119N21O28) m/z=948.

Ac-Asn-Thr-Gln-Thr-Leu-Ala-Lys-Pro-Pro-Glu-His-Thr-Gly-Lys(6FAM)-NH2 16 Calculated: [M+2H]2+ (C88H121N21O28) m/z=963. Found ESI: [M+2H]2+ (C88H121N21O28) m/z=963.

Ac-Asn-Thr-Gln-Thr-Leu-Ala-Lys-Phe-Pro-Glu-His-Thr-Gly-Lys(6FAM)-NH2 17 Calculated: [M+2H]2+ (C92H123N21O28) m/z=986. Found ESI: [M+2H]2+ (C92H123N21O28) m/z=986.

Ac-Asn-Thr-Gln-Thr-Leu-Ala-Glu-Ala-Pro-Glu-His-Thr-Gly-Lys(6FAM)-NH2 18 Calculated: [M+2H]2+ (C85H114N20O30) m/z=948. Found ESI: [M+2H]2+ (C85H114N20O30) m/z=948.

Ac-Asn-Thr-Gln-Thr-Leu-His-Glu-Ala-Pro-Glu-His-Thr-Gly-Lys(6FAM)-NH2 19 Calculated: [M+2H]2+ (C88H116N22O30) m/z=982. Found ESI: [M+2H]2+ (C88H116N22O30) m/z=982.

Ac-Asn-Thr-Gln-Thr-Leu-Phe-Lys-Ala-Pro-Glu-His-Thr-Gly-Lys(6FAM)-NH2 20 Calculated: [M+2H]2+ (C92H123N21O28) m/z=986. Found ESI: [M+2H]2+ (C92H123N21O28) m/z=986.

Ac-Asn-Thr-Gln-Thr-Leu-Ala-Lys-Ala-Lys-Ala-Pro-Glu-His-Thr-Gly-Lys(6FAM)-NH2 21 Calculated: [M+2H]2+ (C86H120N22O28) m/z=955. Found ESI: [M+2H]2+ (C86H120N22O28) m/z=955.

Ac-Asn-Thr-Gln-Ala-Leu-Ala-Lys-Ala-Pro-Glu-His-Thr-Gly-Lys(6FAM)-NH2 22 Calculated: [M+2H]2+ (C85H117N21O27) m/z=933. Found ESI: [M+2H]2+ (C85H117N21O27) m/z=933.

Ac-Asn-Thr-Glu-Thr-Leu-Ala-Lys-Ala-Pro-Glu-His-Thr-Gly-Lys(6FAM)-NH2 23 Calculated: [M+2H]2+ (C86H118N20O29) m/z=948. Found ESI: [M+2H]2+ (C86H118N20O29) m/z=948.

Ac-Asn-Thr-Lys-Thr-Leu-Ala-Lys-Ala-Pro-Glu-His-Thr-Gly-Lys(6FAM)-NH2 24 Calculated: [M+2H]2+ (C87H123N21O27) m/z=948. Found ESI: [M+2H]2+ (C87H123N21O27) m/z=948.

Ac-Asn-Ala-Gln-Thr-Leu-Ala-Lys-Ala-Pro-Glu-His-Thr-Gly-Lys(6FAM)-NH2 25 Calculated: [M+2H]2+ (C85H117N21O27) m/z=933. Found ESI: [M+2H]2+ (C85H117N21O27) m/z=933.

Ac-Ala-Thr-Gln-Thr-Leu-Ala-Lys-Ala-Pro-Glu-His-Thr-Gly-Lys(6FAM)-NH2 26 Calculated: [M+2H]2+ (C85H118N20O27) m/z=927. Found ESI: [M+2H]2+ (C85H118N20O27) m/z=927.

Ac-Pro-Glu-His-Thr-Leu-Ala-Lys-Ala-Pro-Glu-His-Thr-Gly-Lys(6FAM)-NH2 27 Calculated: [M+2H]2+ (C88H119N21O27) m/z=958. Found ESI: [M+2H]2+ (C88H119N21O27) m/z=958.

Ac-Glu-His-Thr-Gly-Cys(Cy5)-NH2 28 Calculated: [M+H]+ (C61H79N12O18S3) m/z=1367. Found ESI: [M+H]+ (C61H79N12O18S3) m/z=1367.

Ac-Glu-His-Thr-Gly-Gly-Gly-Cys(Cy5)-NH2 29 Calculated: [M+H]+ (C65H85N14O20S3) m/z=1479. Found ESI: [M+H]+ (C65H85N14O20S3) m/z=1479.

Ac-Thr-Thr-Thr-Gly-Gly-Gly-Cys(Cy5)-NH2 30 Calculated: [M+H]+ (C62H86N11O21S3) m/z=1416. Found ESI: [M+H]+ (C62H86N11O21S3) m/z=1416.

Ac-Glu-Glu-Thr-Gly-Gly-Gly-Cys(Cy5)-NH2 31 Calculated: [M+H]+ (C64H86N11O23S3) m/z=1472. Found ESI: [M+H]+ (C64H86N11O23S3) m/z=1472.

Ac-Lys-His-Thr-Gly-Gly-Gly-Cys(Cy5)-NH2 32 Calculated: [M+H]+ (C66H91N14O19S3) m/z=1479. Found ESI: [M+H]+ (C66H91N14O19S3) m/z=1479.

Ac-Glu-Lys-Thr-Gly-Gly-Gly-Cys(Cy5)-NH2 33 Calculated: [M+H]+ (C65H91N12O21S3) m/z=1471. Found ESI: [M+H]+ (C65H91N12O21S3) m/z=1471.

Example 4

In Vivo Demonstration of Nerve Visualization

Peptides in Table 1 were prepared and evaluated for their ability to show fluorescence contrast enhancement of nerve compared to proximal muscle tissue and skin. Peptides A and B are control peptides.

TABLE 1

| Peptide | Peptide Sequence |
|---|---|
| A | Ac-Ser-His-Ser-Asn-Thr-Gln-Thr-Leu-Ala-Lys-Ala-Pro-Glu-His-Thr-Gly-Lys(6FAM)-NH2 |
| B | Ac-Ser-His-Ser-Asn-Thr-Gln-Thr-Leu-Ala-Lys-Ala-Pro-Glu-His-Thr-Gly-Cys(Cy5)-NH2 |

TABLE 1-continued

| Peptide | Peptide Sequence |
|---|---|
| 1 | H2N-Lys(6FAM)-NH2 |
| 2 | Ac-Gly-Lys(6FAM)-NH2 |
| 3 | Ac-Glu-His-Thr-Gly-Lys(6FAM)-NH2 |
| 4 | Ac-Lys-Ala-Pro-Glu-His-Thr-Gly-Lys(6FAM)-NH2 |
| 5 | Ac-Leu-Ala-Lys-Ala-Pro-Glu-His-Thr-Gly-Lys(6FAM)-NH2 |
| 6 | Ac-Gln-Thr-Leu-Ala-Lys-Ala-Pro-Glu-His-Thr-Gly-Lys(6FAM)-NH2 |
| 7 | Ac-Thr-Gln-Thr-Leu-Ala-Lys-Ala-Pro-Glu-His-Thr-Gly-Lys(6FAM)-NH2 |
| 8 | Ac-Asn-Thr-Gln-Thr-Leu-Ala-Lys-Ala-Pro-Glu-His-Thr-Gly-Lys(6FAM)-NH2 |
| 9 | Ac-Asn-Thr-Gln-Thr-Leu-Ala-Lys-Ala-Pro-Glu-His-Ala-Gly-Lys(6FAM)-NH2 |
| 10 | Ac-Asn-Thr-Gln-Thr-Leu-Ala-Lys-Ala-Pro-Glu-Ala-Thr-Gly-Lys(6FAM)-NH2 |
| 11 | Ac-Asn-Thr-Gln-Thr-Leu-Ala-Lys-Ala-Pro-His-Glu-Thr-Gly-Lys(6FAM)-NH2 |
| 12 | Ac-Asn-Thr-Gln-Thr-Leu-Ala-Lys-Ala-Pro-Ala-His-Thr-Gly-Lys(6FAM)-NH2 |
| 13 | Ac-Asn-Thr-Gln-Thr-Leu-Ala-Lys-Ala-Pro-Lys-His-Thr-Gly-Lys(6FAM)-NH2 |
| 14 | Ac-Asn-Thr-Gln-Thr-Leu-Ala-Lys-Ala-Ala-Glu-His-Thr-Gly-Lys(6FAM)-NH2 |
| 15 | Ac-Asn-Thr-Gln-Thr-Leu-Ala-Lys-Ala-D-pro-Glu-His-Thr-Gly-Lys(6FAM)-NH2 |
| 16 | Ac-Asn-Thr-Gln-Thr-Leu-Ala-Lys-Pro-Pro-Glu-His-Thr-Gly-Lys(6FAM)-NH2 |
| 17 | Ac-Asn-Thr-Gln-Thr-Leu-Ala-Lys-Phe-Pro-Glu-His-Thr-Gly-Lys(6FAM)-NH2 |
| 18 | Ac-Asn-Thr-Gln-Thr-Leu-Ala-Glu-Ala-Pro-Glu-His-Thr-Gly-Lys(6FAM)-NH2 |
| 19 | Ac-Asn-Thr-Gln-Thr-Leu-His-Glu-Ala-Pro-Glu-His-Thr-Gly-Lys(6FAM)-NH2 |
| 20 | Ac-Asn-Thr-Gln-Thr-Leu-Phe-Lys-Ala-Pro-Glu-His-Thr-Gly-Lys(6FAM)-NH2 |
| 21 | Ac-Asn-Thr-Gln-Thr-Lys-Ala-Lys-Ala-Pro-Glu-His-Thr-Gly-Lys(6FAM)-NH2 |
| 22 | Ac-Asn-Thr-Gln-Ala-Leu-Ala-Lys-Ala-Pro-Glu-His-Thr-Gly-Lys(6FAM)-NH2 |
| 23 | Ac-Asn-Thr-Glu-Thr-Leu-Ala-Lys-Ala-Pro-Glu-His-Thr-Gly-Lys(6FAM)-NH2 |
| 24 | Ac-Asn-Thr-Lys-Thr-Leu-Ala-Lys-Ala-Pro-Glu-His-Thr-Gly-Lys(6FAM)-NH2 |
| 25 | Ac-Asn-Ala-Gln-Thr-Leu-Ala-Lys-Ala-Pro-Glu-His-Thr-Gly-Lys(6FAM)-NH2 |
| 26 | Ac-Ala-Thr-Gln-Thr-Leu-Ala-Lys-Ala-Pro-Glu-His-Thr-Gly-Lys(6FAM)-NH2 |
| 27 | Ac-Pro-Glu-His-Thr-Leu-Ala-Lys-Ala-Pro-Glu-His-Thr-Gly-Lys(6FAM)-NH2 |
| 28 | Ac-Glu-His-Thr-Gly-Cys(Cy5)-NH2 |
| 29 | Ac-Glu-His-Thr-Gly-Gly-Gly-Cys(Cy5)-NH2 |
| 30 | Ac-Thr-Thr-Thr-Gly-Gly-Gly-Cys(Cy5)-NH2 |
| 31 | Ac-Glu-Glu-Thr-Gly-Gly-Gly-Cys(Cy5)-NH2 |
| 32 | Ac-Lys-His-Thr-Gly-Gly-Gly-Cys(Cy5)-NH2 |
| 33 | Ac-Glu-Lys-Thr-Gly-Gly-Gly-Cys(Cy5)-NH2 |

Figure 6:
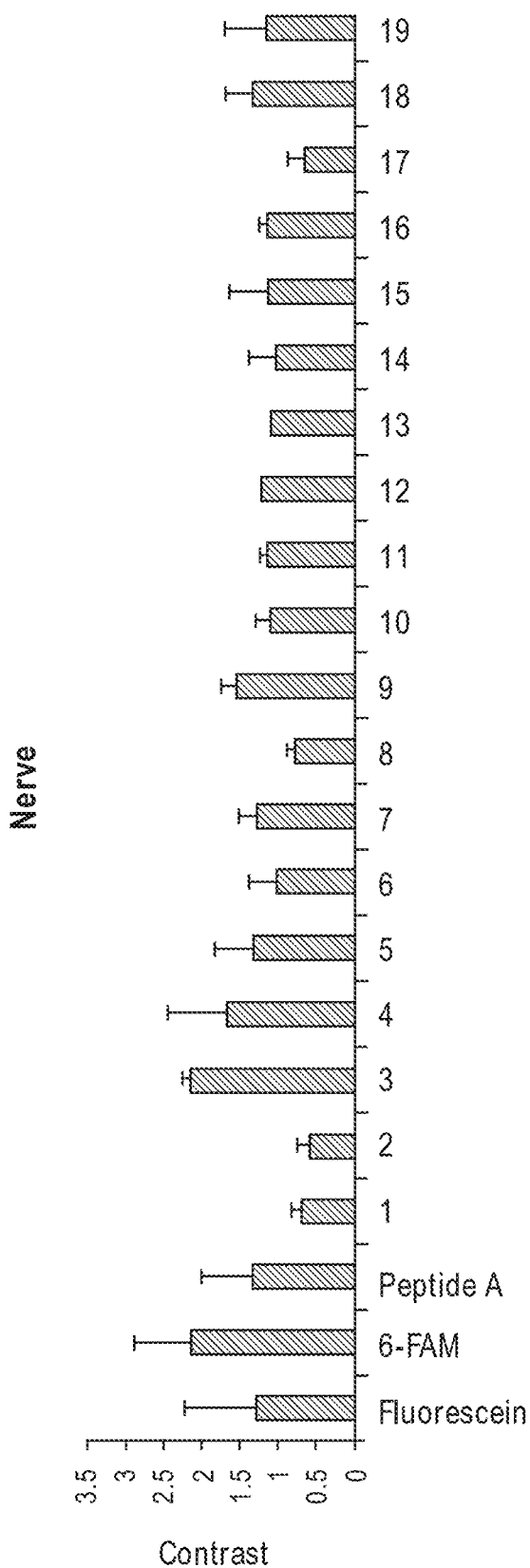
FIG. 6 illustrates sciatic nerve fluorescence contrast activity for visualization agents 2 hours after administration.
Figure 7:
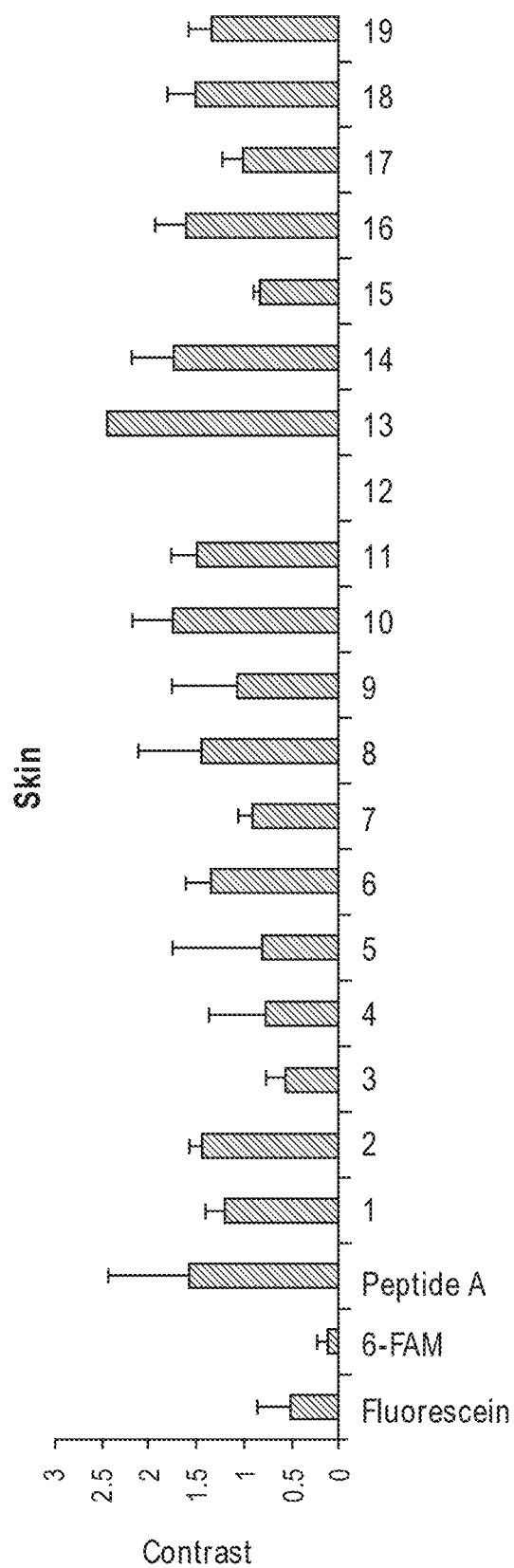
FIG. 7 illustrates skin fluorescence contrast activity for visualization agents 2 hours after administration.

The identified molecules show fluorescence contrast of the mouse sciatic nerve at 2 hours after IV administration, FIG. 6. The mouse skin fluorescence is shown in FIG. 7.

Fluorescence contrast activity of was assessed using male euthymic and immunocompetent hairless SKH1-E mice (25-35 grams). On the day of study, each involved mouse was weighed and restrained using the rotating tail injector for intravenous (tail vein) injection in conscious animal.

Test agents were injected intravenously into the tail vein (30-150 nmol in 0.1 mL/mouse). The animals were returned to assigned cage and kept under controlled environmental conditions before being examined for sciatic nerve fluorescence labeling 2 hours later.

Two hours after the intravenous injection, the mice were anesthetized with a mixture of ketamine HCl/Xylazine HCl solution administered intraperitoneally. The deeply anesthetized mice were transferred on the piece of cork for blunt dissection of sciatic nerve.

Full body imaging of deeply anesthetized mouse with open surgical wound/exposed sciatic nerve was then performed using a computerized imaging system with appropriate excitation/emission filters. The full body imaging was used to calculate the skin staining activity of the visualization agents.

After the full body imaging, the deeply anesthetized mice were transferred on the computerized fluorescent stereomicroscope equipped with appropriate excitation/emission filters to examine and record the fluorescence specific to sciatic nerve and compare it to that documented on the surrounding tissues such as muscle. All captured images were examined and analyzed using Image J to generate quantitative data.

For each experimental group, fluorescence intensities from each mouse sciatic nerve were averaged to generate the Mean±SEM value. The background was defined as the average fluorescence intensities of the muscle tissue surrounding the sciatic nerve. The fluorescence contrast (C) is defined and calculated as $C=(I_N-I_B)/I_B$, where $I_N$ is the average nerve fluorescence intensity and $I_B$ is the average proximal background intensity. Constrast>0.4 is considered good.

Example 5

In Vivo Fluorescence Imaging

In vivo fluorescence nerve imaging of synthesized candidate fluorescent nerve visualization agents, identified molecules that provide good fluorescent contrast of the mouse sciatic nerve.

Figure 8:
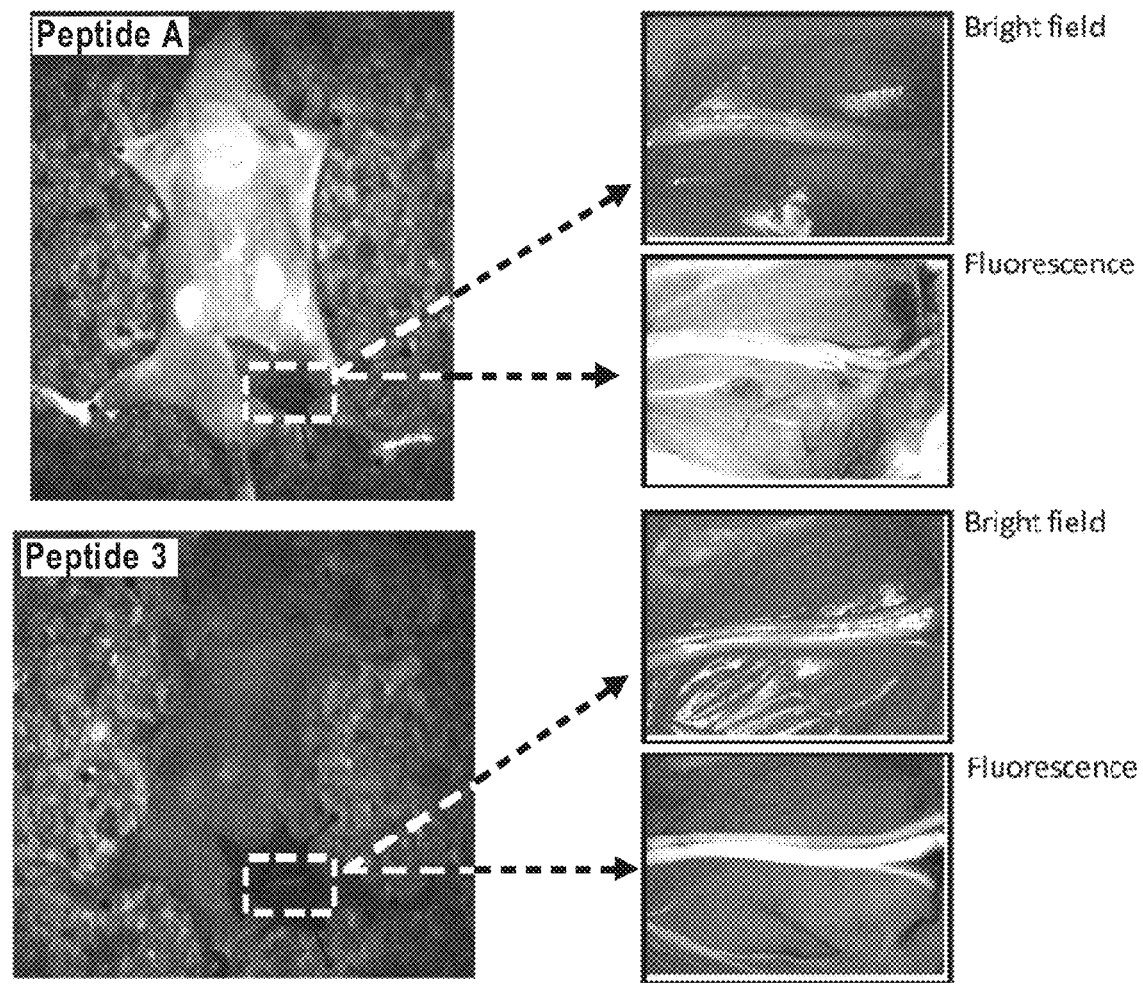
FIG. 8 illustrates the fluorescence nerve contrast of Peptide 3. Peptide 3 shows high fluorescence nerve contrast and significantly less skin fluorescence compared to peptide A. 150 nmol of both peptides were administered via tail vein injection and imaging was done at 2 h.

An example with excellent fluorescence enhancement is peptide 3. The data are shown in FIG. 8.

The contrast is very high and is greater that peptide A. Skin fluorescence is much less than for Peptide A.

Example 6

Indocarbocyanine Fluorophores

Figure 4:
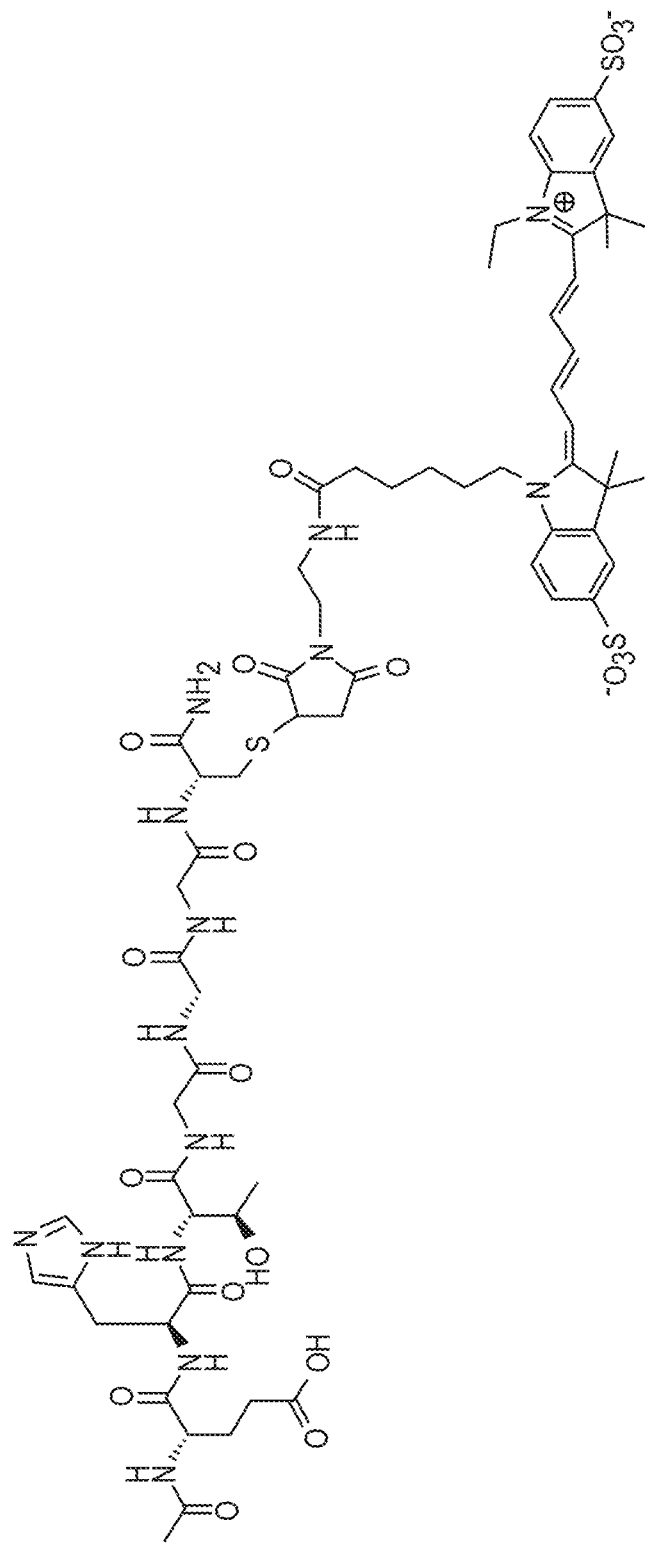
FIG. 4 illustrates the chemical structure of Peptide 29.
Figure 5A:
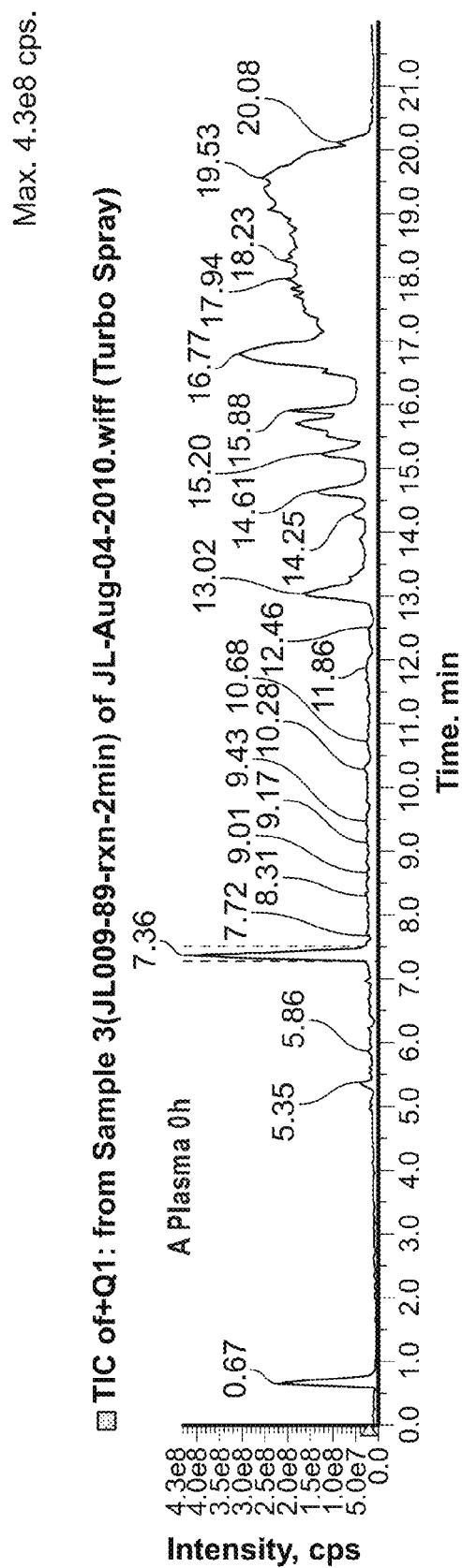
FIG. 5 illustrates the results of digesting Peptide A in Plasma at 37° C.
Figure 5B:
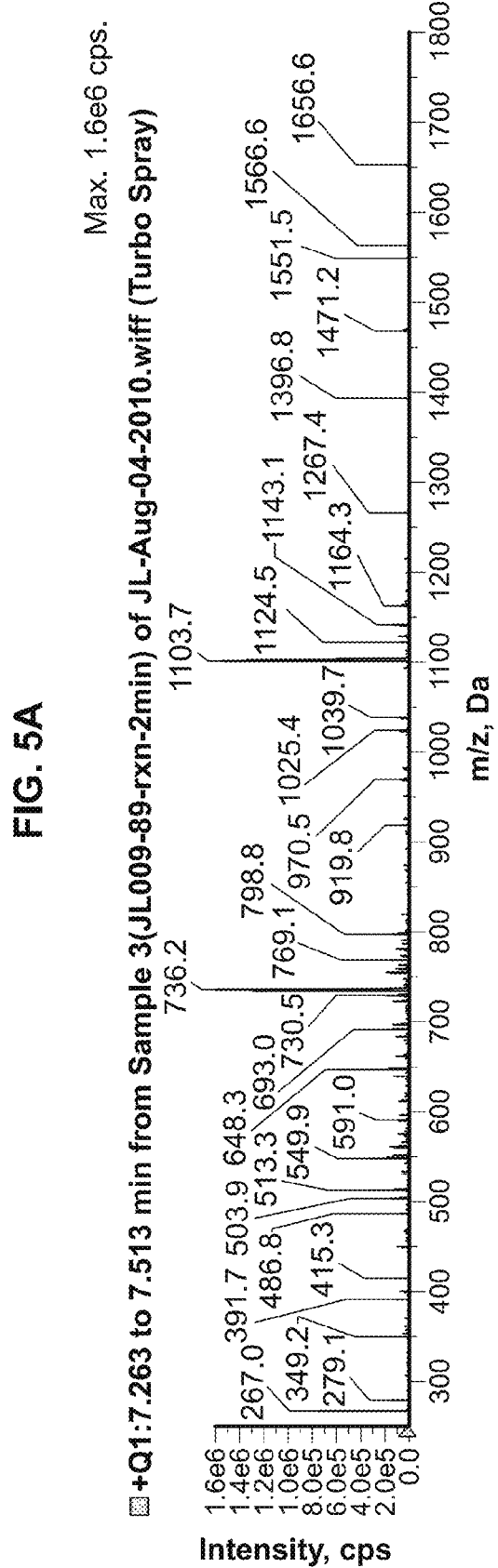
Figure 5C:
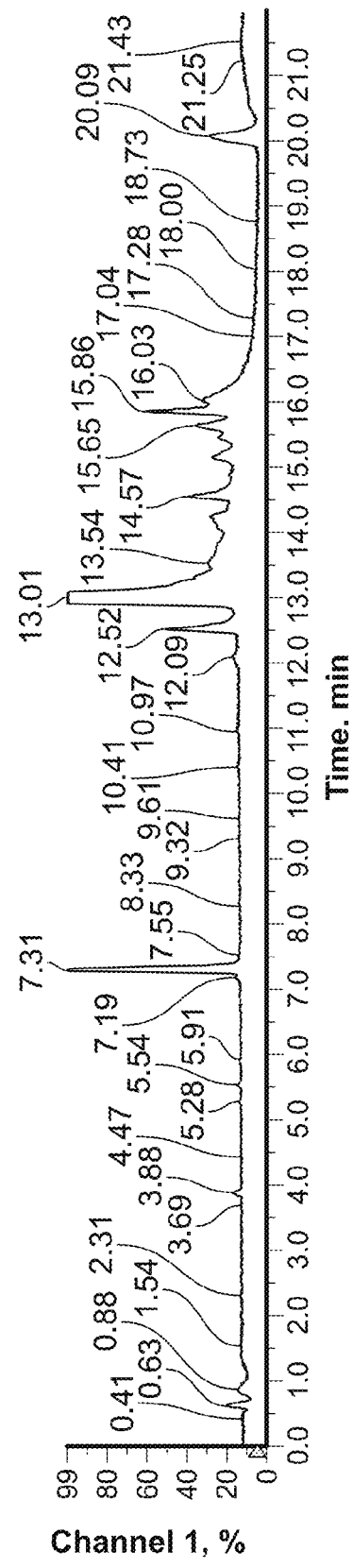
Figure 5D:
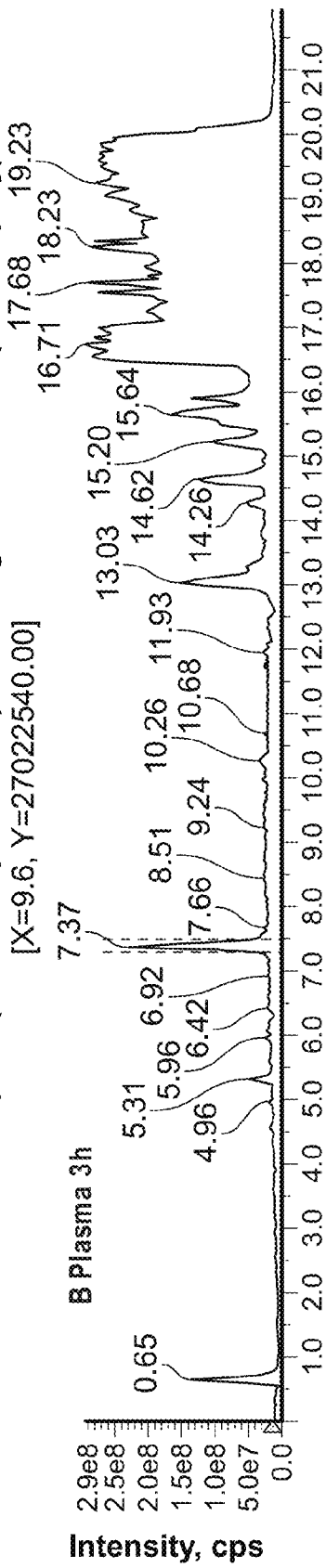
Figure 5E:
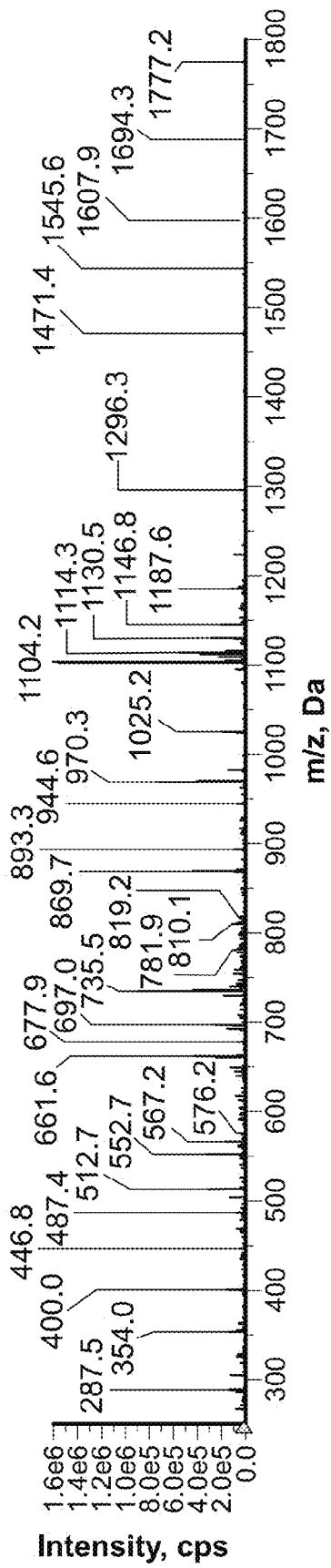
Figure 5F:
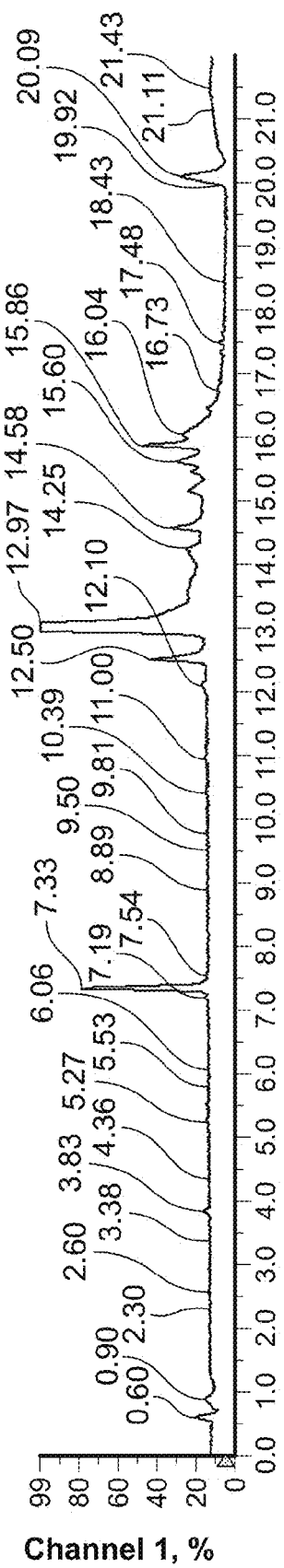
Figure 5G:
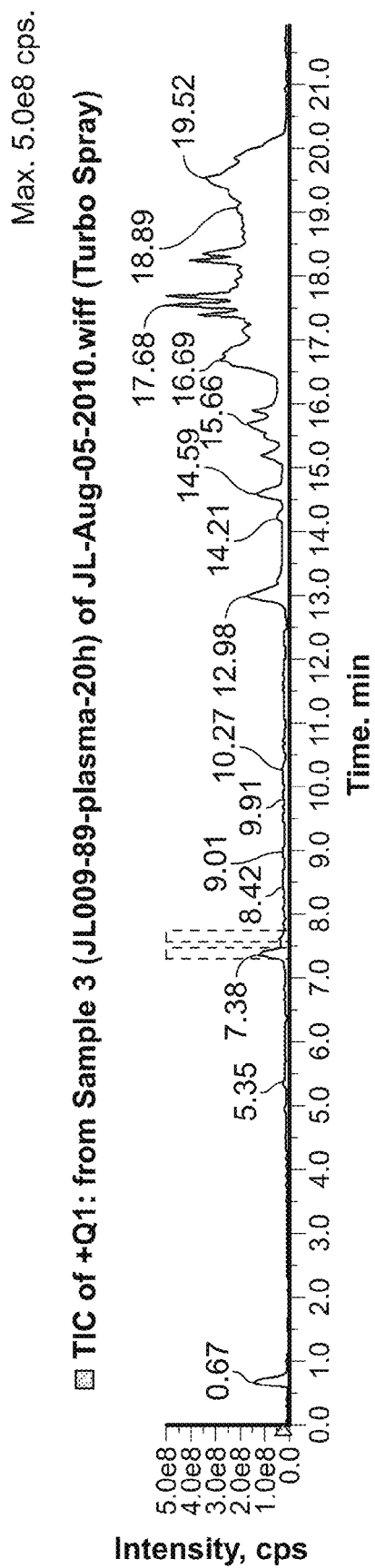
Figure 5H:
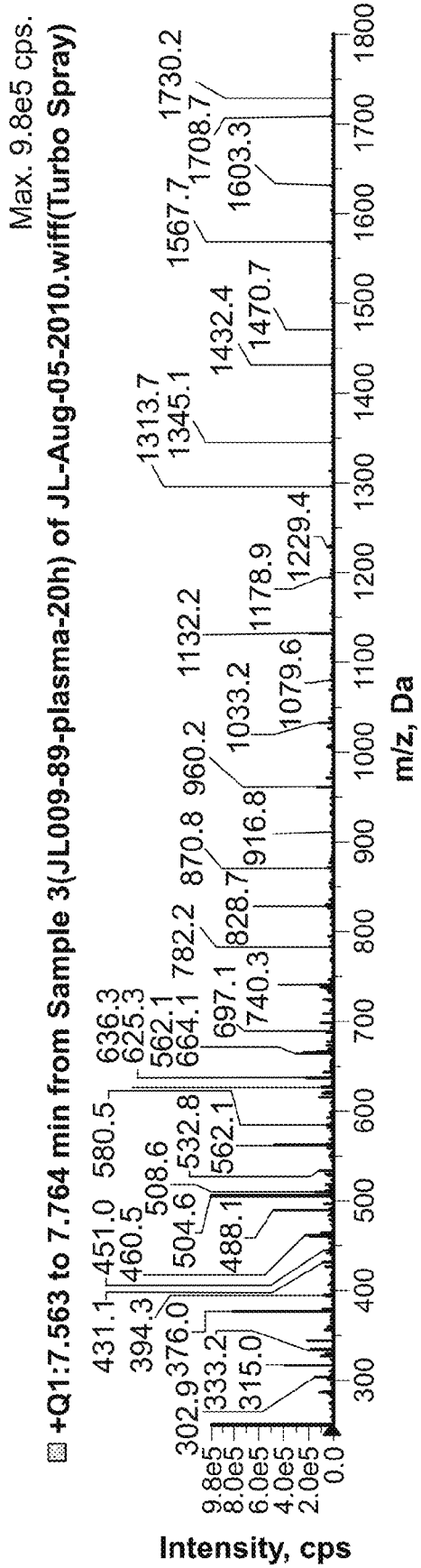
Figure 5I:
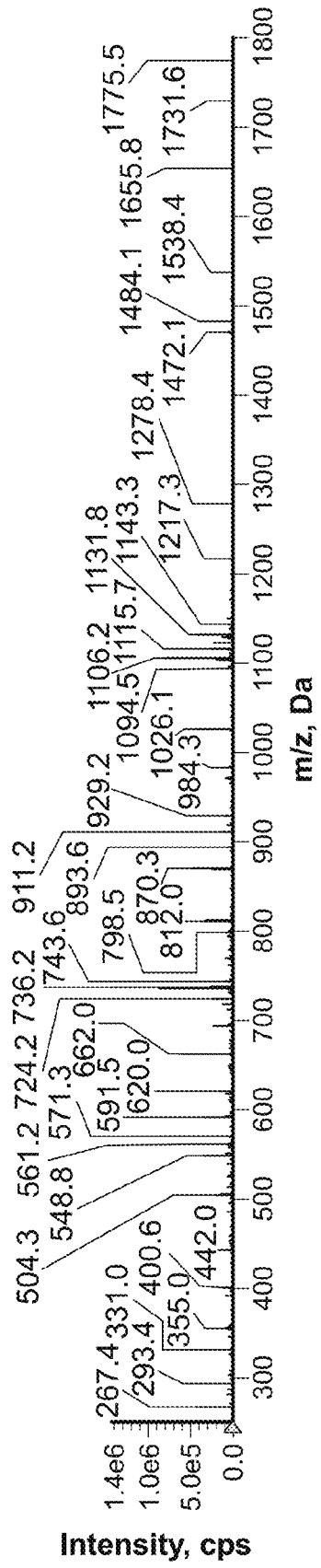
Figure 5J:
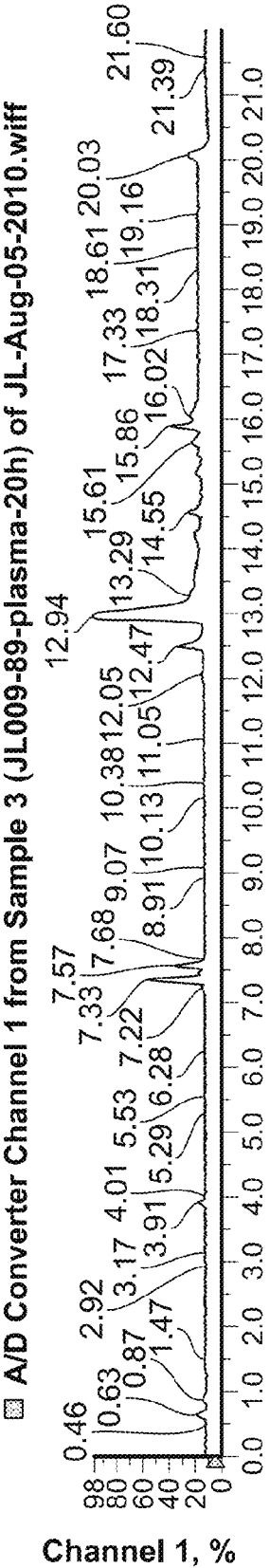
Figure 5K:
Figure 5L:
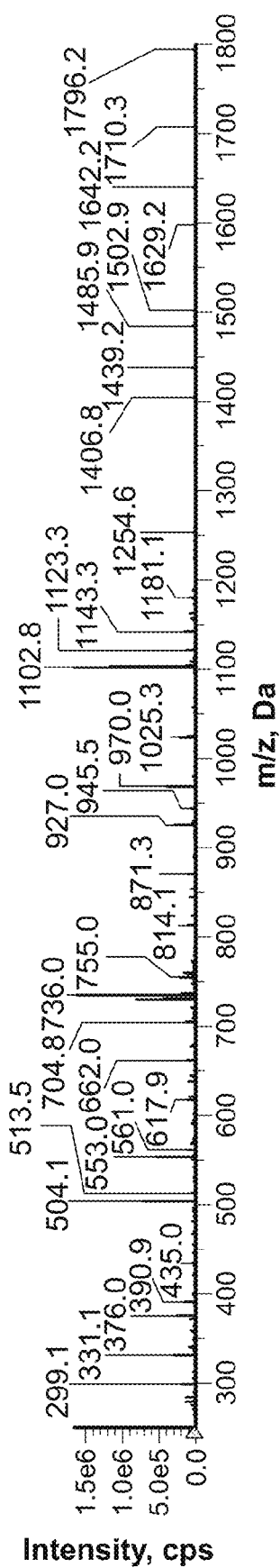
Figure 5M:
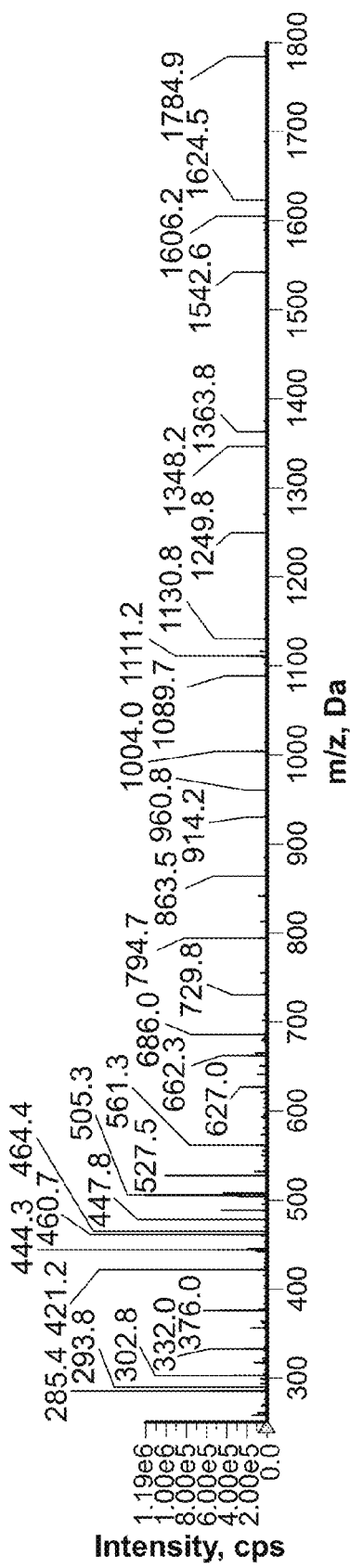
Figure 5N:
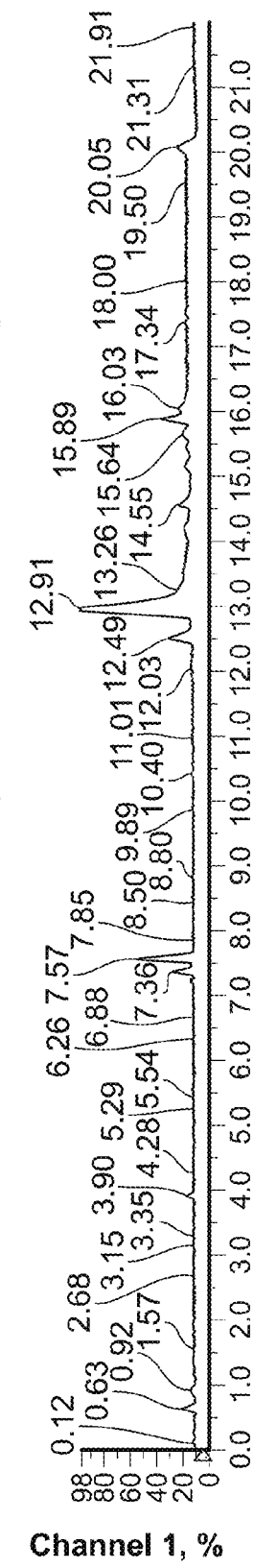
Figure 5O:
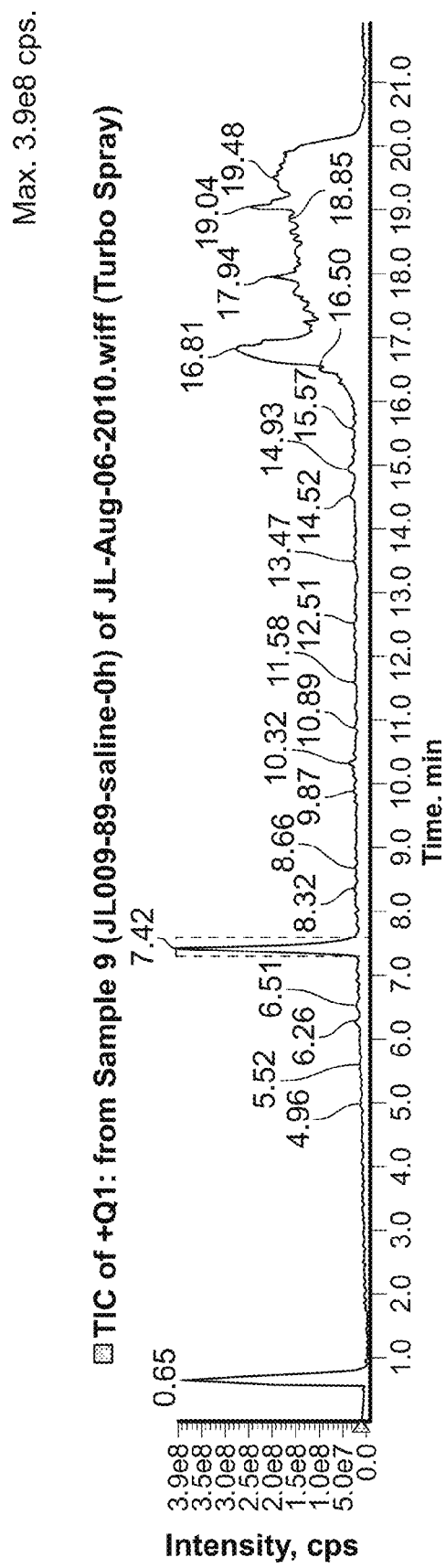
Figure 5P:
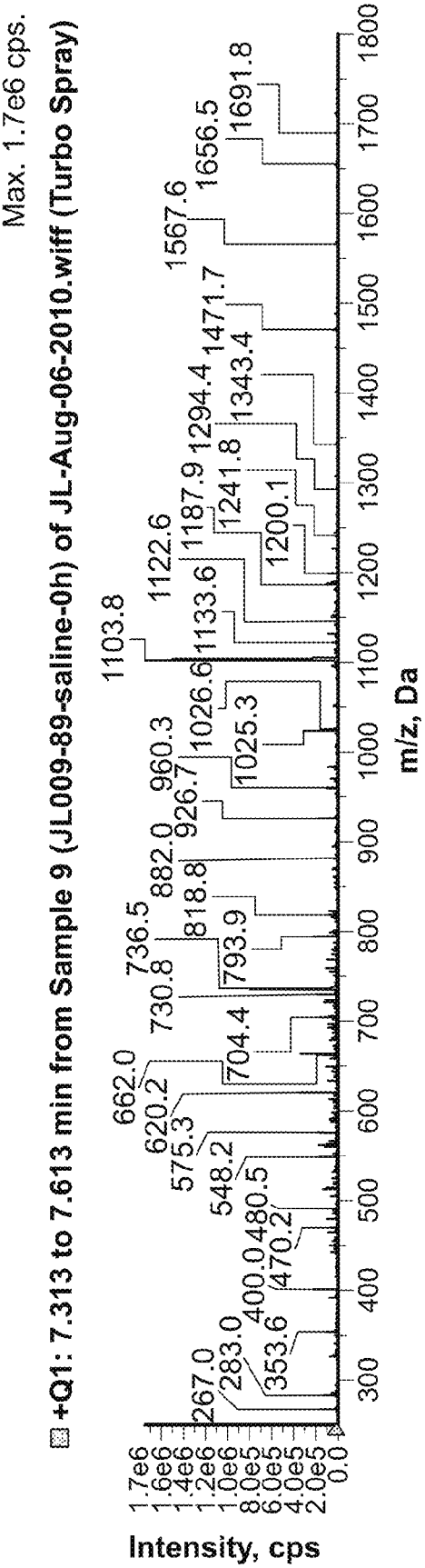
Figure 5Q:
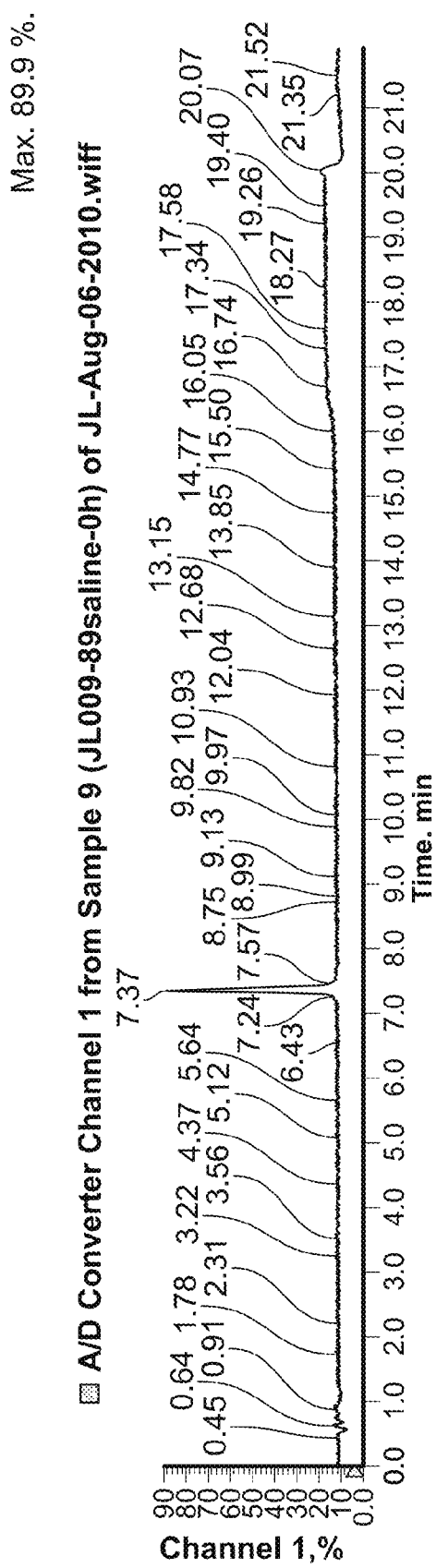
Figure 5R:
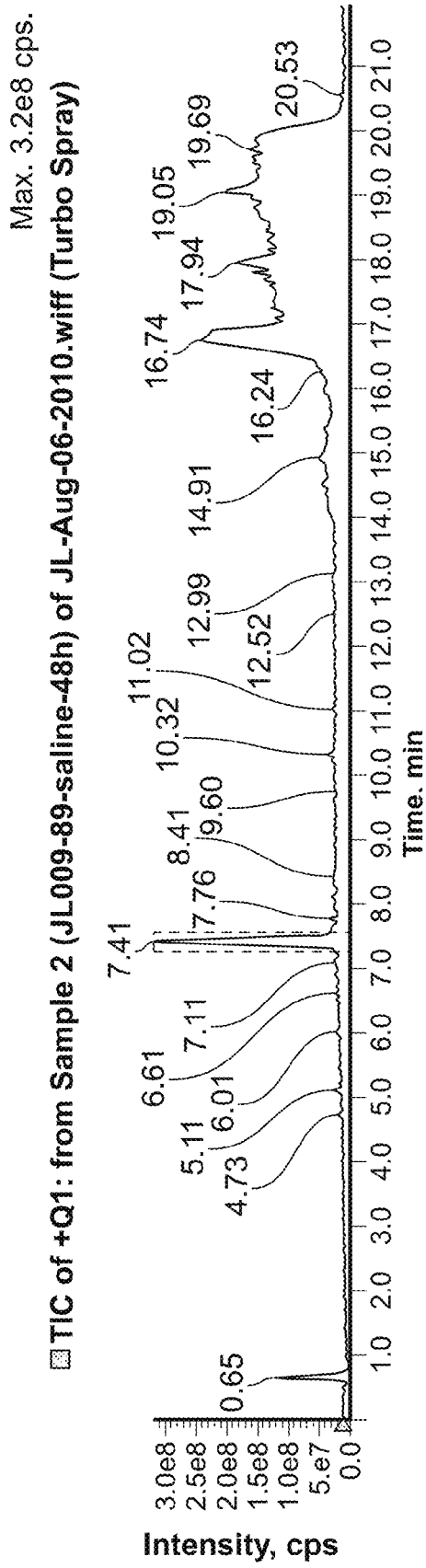
Figure 5S:
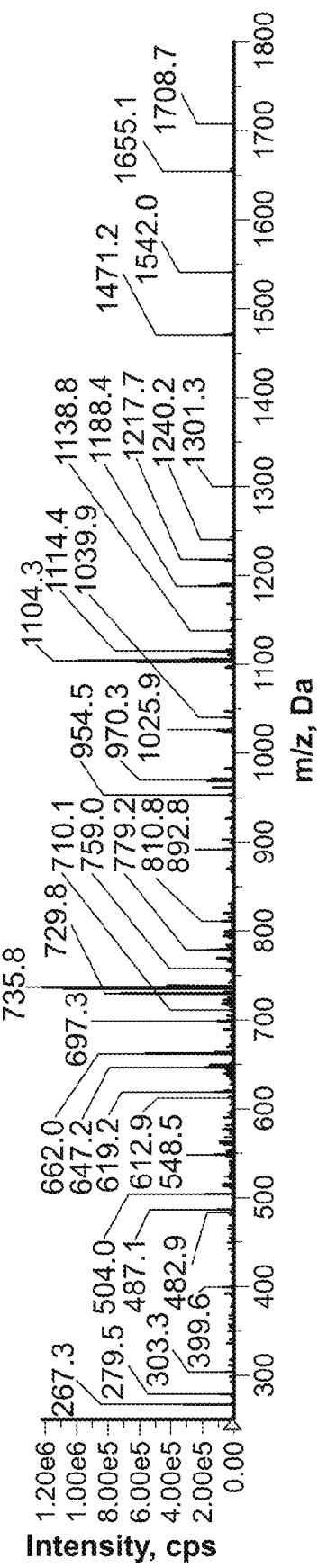
Figure 5T:
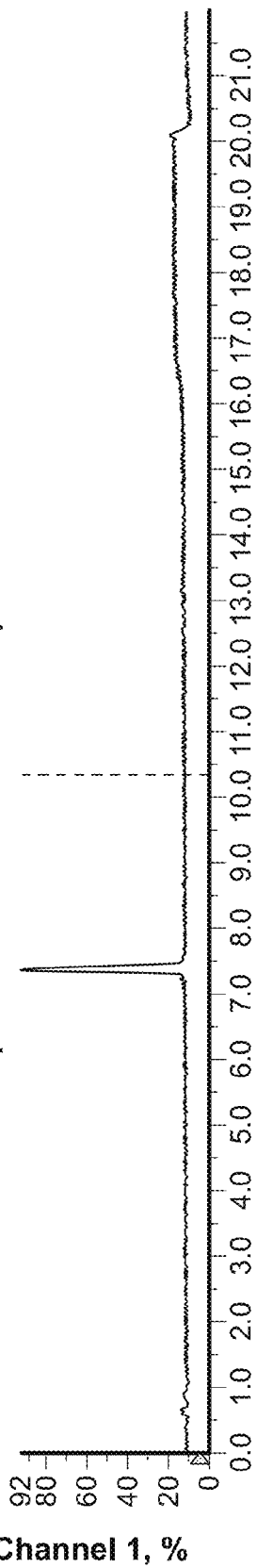

Based on the results of 6-FAM labeled peptides (2-27), Cy5 labeled peptides 28-33 were prepared. As an example, the structure of peptide 29 is shown in FIG. 4. The C-terminus lysine residue was replaced with a cysteine for the attachment of Cy5 dye via maleimide coupling.

Example 7

In Vivo Assay of Peptide 29

Figure 9A:
FIG. 9 provides fluorescence images of mouse sciatic nerve stained with (A) peptide B and (B) peptide 29. 150 nmol of both peptides were administered via tail vein injection and imaging was done at 2 h.
Figure 9B:
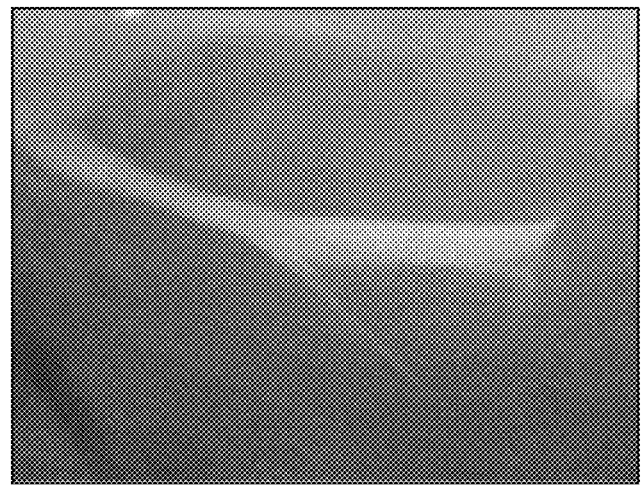
Figure 10A:
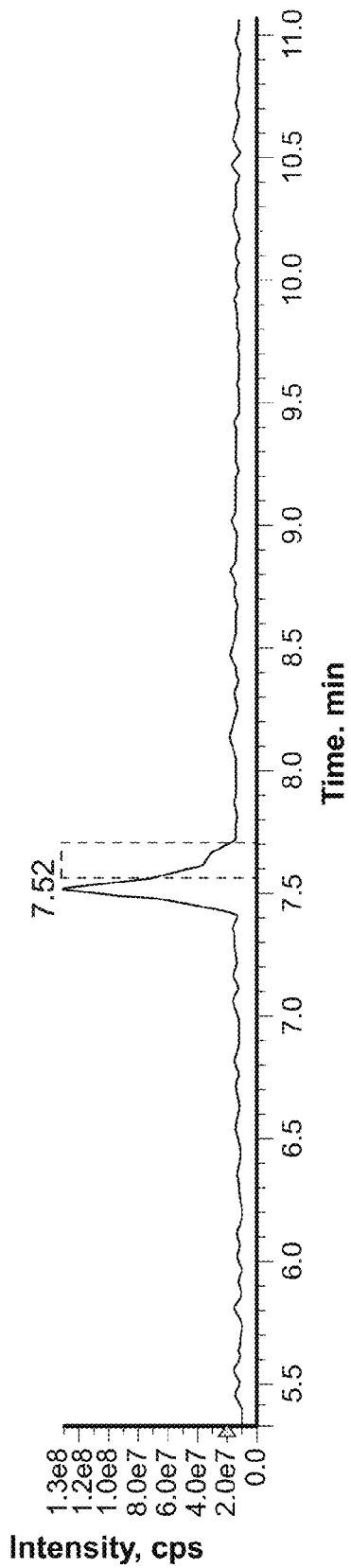
FIG. 10 provides the chemical structures of fluorescent metabolites of peptide A from room temperature digestion.
Figure 10B:
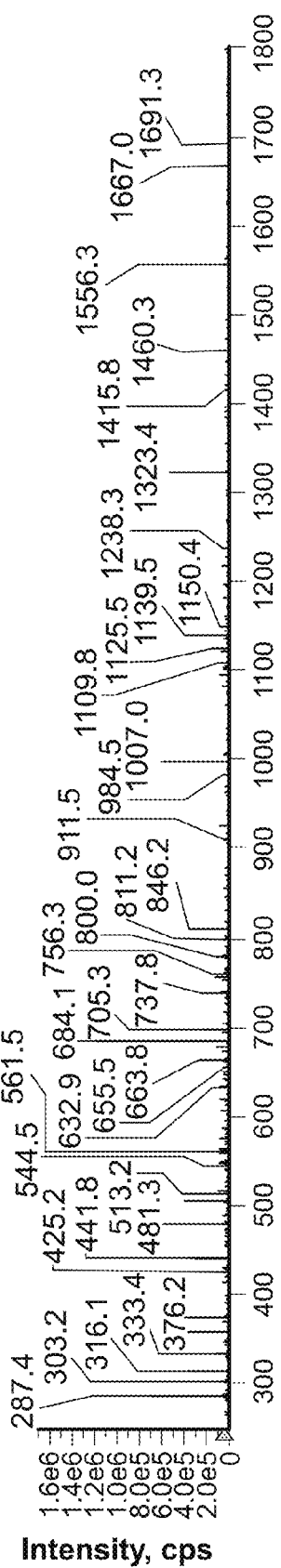
Figure 10E:
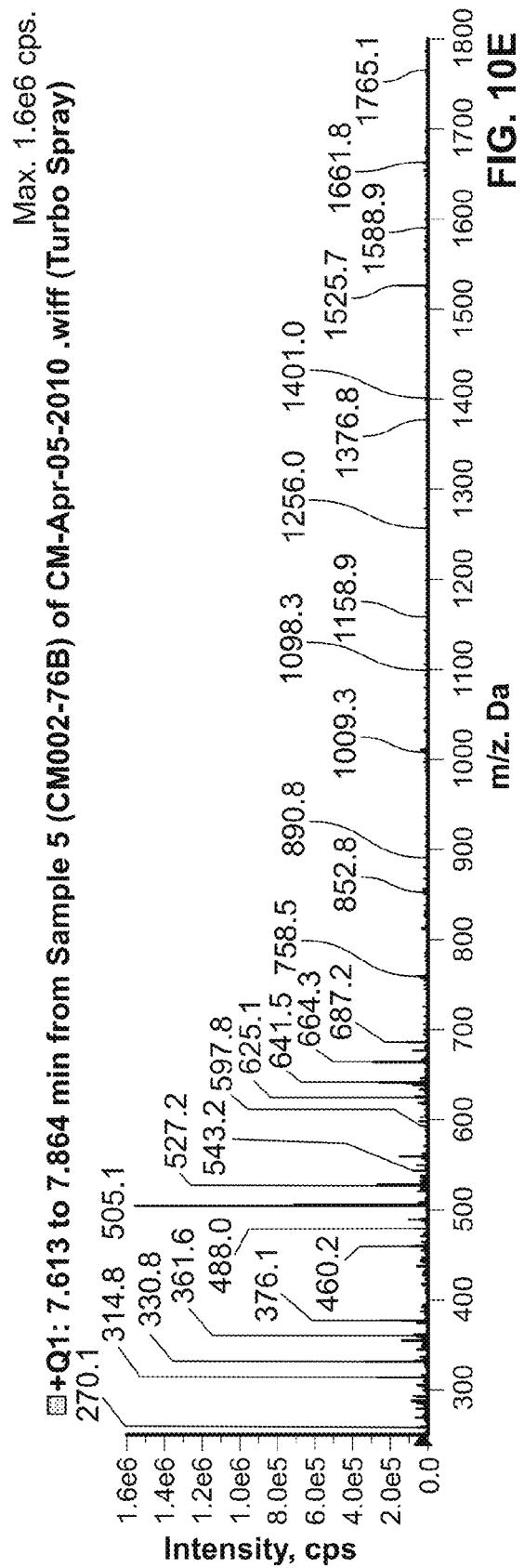
Figure 10F:
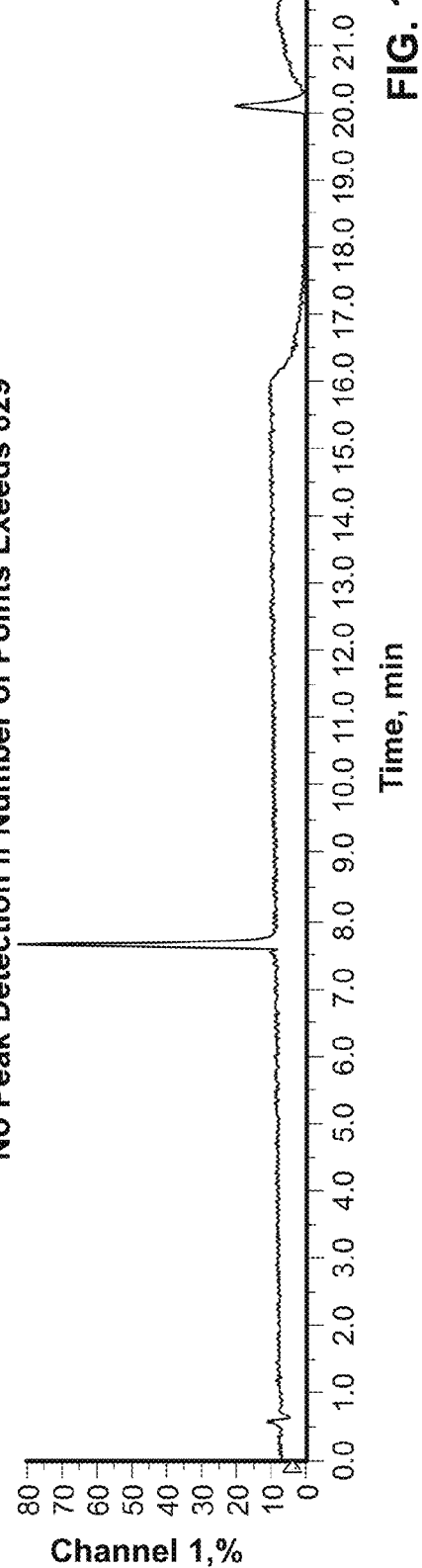
Figure 10G:
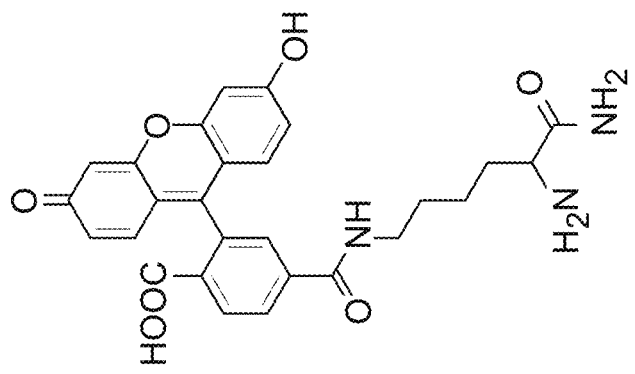
Figure 10G:
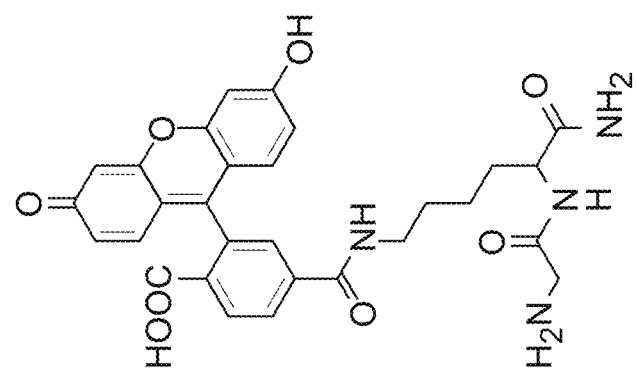
Figure 10G:
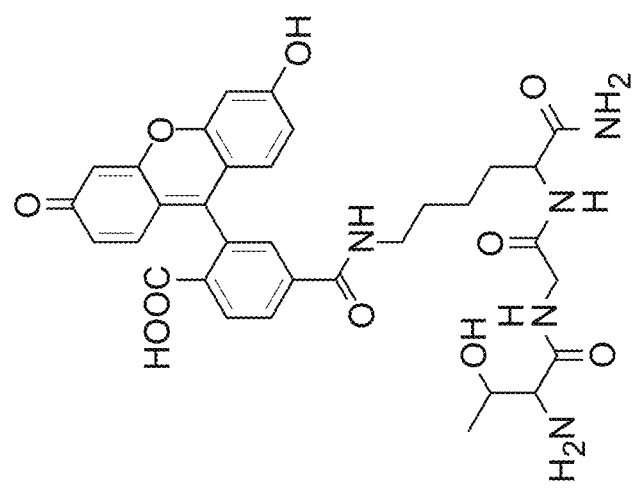

Fluorescence image of mouse sciatic nerve stained with (A) peptide B and (B) peptide 29 are shown in FIG. 9. 150 nmol of both peptides were administered via tail vein injection and imaging was done at 2 h

Example 8

Fluorescent Nerve Visualization Agents Identified from Plasma Digestion of Peptide A 6-Carboxylfluorescein (6-FAM) labeled peptide A (1 mg) was added to freshly prepared mouse plasma (0.5 mL). The resulting solution was gently mixed and incubated at 37° C. The reaction was followed by an LC-MS at different time points. An analogous procedure was done at room temperature with 1-5 mg of Peptide A.

No detectable digested products in plasma were detected in 3 h (Chart A&B, FIG. 5). However, a new peak appeared in HPLC chromatogram (220 nm absorbance) after peptide A was incubated in plasma for 20 h and 48 h (Charts C&D, FIG. 5). The peak was isolated by preparative RP-HPLC. The major truncated component is C-terminus lysine labeled with 6-FAM (Peptide 1, Table 1). As a control, peptide A is stable in saline after 48 h (Chart E&F, FIG. 5). Room temperature digestion was done and identified other fluorescent metabolites which are shown in FIG. 10.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A targeting molecule that labels a neuron or nerve, consisting essentially of:
   (a) an isolated peptide sequence consisting of Formula (XI)

X10-X11-X12-Gly-X13     (Formula (XI)) (SEQ ID NO: 44);

wherein X10 is selected from: Glu, His, Ala, Thr, or Lys;
   wherein X11 is selected from: His, Ala, Thr, Lys, or Glu;
   wherein X12 is selected from: Ala or Thr; and
   wherein X13 is selected from: Lys, Cys, or Gly; and
   (b) a fluorescent moiety;
   wherein the targeting molecule labels the neuron or nerve.

2. The targeting molecule of claim 1, wherein the isolated peptide sequence is selected from: Glu-His-Thr-Gly-Lys (SEQ ID NO. 1); and Glu-His-Thr-Gly-Cys (SEQ ID NO. 26).

3. The targeting molecule of claim 1, wherein the fluorescent moiety is: 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalamal, ECFP, Cerulean, CyPet, YFP, Citrine, Venus, YPet, or a combination thereof.

4. A method of imaging a neuron or nerve, comprising imaging a target contacted with the targeting molecule of claim 1.

5. The method of claim 4, wherein the neuron or nerve, is part of a neuromuscular junction, a sinoartial node, an atriventricular node, or a combination thereof.

6. The method of claim 4, wherein the fluorescent moiety is: 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalamal, ECFP, Cerulean, CyPet, YFP, Citrine, Venus, YPet, or a combination thereof.

7. A method of guided surgery, comprising performing surgery on an individual following visualization of a targeting molecule of claim 1 administered to the individual.

8. The method of claim 7, wherein the fluorescent moiety is: 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalamal, ECFP, Cerulean, CyPet, YFP, Citrine, Venus, YPet, or a combination thereof.

9. A pharmaceutical composition comprising: (a) a targeting molecule of claim 1; and (b) a pharmaceutically acceptable excipient.

10. The pharmaceutical composition of claim 9, wherein the peptide sequence is selected from Glu-His-Thr-Gly-Lys (SEQ ID NO. 1) and Glu-His-Thr-Gly-Cys (SEQ ID NO. 26).

11. The pharmaceutical composition of claim 9, wherein the fluorescent moiety is: 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalamal, ECFP, Cerulean, CyPet, YFP, Citrine, Venus, YPet, or a combination thereof.

12. The method of claim 4, wherein the isolated peptide sequence is selected from Glu-His-Thr-Gly-Lys (SEQ ID NO. 1) and Glu-His-Thr-Gly-Cys (SEQ ID NO. 26).

13. The method of claim 7, wherein the isolated peptide sequence is selected from Glu-His-Thr-Gly-Lys (SEQ ID NO. 1) and Glu-His-Thr-Gly-Cys (SEQ ID NO. 26).

14. The targeting molecule of claim 1, wherein X10 is acetylated.

15. The targeting molecule of claim 1, wherein the fluorescent moiety is covalently attached to the targeting molecule.

16. The targeting molecule of claim 1, wherein the fluorescent moiety is covalently attached to X13.

17. The targeting molecule of claim 1, that is Ac-Glu-His-Thr-Gly-Cys(Cy5).

* * * * *

SEQUENCE LISTING

```
<160> NUMBER OF SEQ ID NOS: 96

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu His Thr Gly Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Lys Ala Pro Glu His Thr Gly Lys
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Ala Lys Ala Pro Glu His Thr Gly Lys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Thr Leu Ala Lys Ala Pro Glu His Thr Gly Lys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Gln Thr Leu Ala Lys Ala Pro Glu His Thr Gly Lys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Thr Gln Thr Leu Ala Lys Ala Pro Glu His Thr Gly Lys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Thr Gln Thr Leu Ala Lys Ala Pro Glu His Ala Gly Lys
1               5                   10
```

```
<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Thr Gln Thr Leu Ala Lys Ala Pro Glu Ala Thr Gly Lys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Thr Gln Thr Leu Ala Lys Ala Pro His Glu Thr Gly Lys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Thr Gln Thr Leu Ala Lys Ala Pro Ala His Thr Gly Lys
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Thr Gln Thr Leu Ala Lys Ala Pro Lys His Thr Gly Lys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Thr Gln Thr Leu Ala Lys Ala Ala Glu His Thr Gly Lys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
-continued

<220> FEATURE:
<221> NAME/KEY: MOD_RES
<222> LOCATION: (9)..(9)
<223> OTHER INFORMATION: D-Pro

<400> SEQUENCE: 13

Asn Thr Gln Thr Leu Ala Lys Ala Pro Glu His Thr Gly Lys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Thr Gln Thr Leu Ala Lys Pro Pro Glu His Thr Gly Lys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Thr Gln Thr Leu Ala Lys Phe Pro Glu His Thr Gly Lys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Thr Gln Thr Leu Ala Glu Ala Pro Glu His Thr Gly Lys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Thr Gln Thr Leu His Glu Ala Pro Glu His Thr Gly Lys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Thr Gln Thr Leu Phe Lys Ala Pro Glu His Thr Gly Lys
1               5                   10
```

```
<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Thr Gln Thr Lys Ala Lys Ala Pro Glu His Thr Gly Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Thr Gln Ala Leu Ala Lys Ala Pro Glu His Thr Gly Lys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Thr Glu Thr Leu Ala Lys Ala Pro Glu His Thr Gly Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asn Thr Lys Thr Leu Ala Lys Ala Pro Glu His Thr Gly Lys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn Ala Gln Thr Leu Ala Lys Ala Pro Glu His Thr Gly Lys
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 24

Ala Thr Gln Thr Leu Ala Lys Ala Pro Glu His Thr Gly Lys
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Glu His Thr Leu Ala Lys Ala Pro Glu His Thr Gly Lys
1               5                   10

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu His Thr Gly Cys
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu His Thr Gly Gly Gly Cys
1               5

<210> SEQ ID NO 28
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys
1

<210> SEQ ID NO 29
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Lys
1

<210> SEQ ID NO 30
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 30

Thr Thr Thr Gly Gly Gly Cys
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Glu Thr Gly Gly Gly Cys
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys His Thr Gly Gly Gly Cys
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Lys Thr Gly Gly Gly Cys
1               5

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Thr, Ser, Ala or Glu
<220> FEATURE:
<221> NAME/KEY: MOD_RES
<222> LOCATION: (4)..(4)
<223> OTHER INFORMATION: Thr, Ser or Ala
<220> FEATURE:
<221> NAME/KEY: MOD_RES
<222> LOCATION: (6)..(6)
<223> OTHER INFORMATION: Thr, Ser, Ala, His or Phe
<220> FEATURE:
<221> NAME/KEY: MOD_RES
<222> LOCATION: (9)..(9)
<223> OTHER INFORMATION: Pro or Ala

<400> SEQUENCE: 34
```

```
Asn Xaa Gln Xaa Leu Xaa Lys Ala Xaa Glu His Thr Gly Lys
1               5                   10
```

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Ala or Pro
<220> FEATURE:
<221> NAME/KEY: MOD_RES
<222> LOCATION: (2)..(2)
<223> OTHER INFORMATION: Thr, Ala or Glu
<220> FEATURE:
<221> NAME/KEY: MOD_RES
<222> LOCATION: (3)..(3)
<223> OTHER INFORMATION: Gln, Glu, Lys or His
<220> FEATURE:
<221> NAME/KEY: MOD_RES
<222> LOCATION: (4)..(4)
<223> OTHER INFORMATION: Thr or Ala
<220> FEATURE:
<221> NAME/KEY: MOD_RES
<222> LOCATION: (5)..(5)
<223> OTHER INFORMATION: Leu or Lys
<220> FEATURE:
<221> NAME/KEY: MOD_RES
<222> LOCATION: (6)..(6)
<223> OTHER INFORMATION: Ala, His or Phe
<220> FEATURE:
<221> NAME/KEY: MOD_RES
<222> LOCATION: (7)..(7)
<223> OTHER INFORMATION: Lys or Glu
<220> FEATURE:
<221> NAME/KEY: MOD_RES
<222> LOCATION: (8)..(8)
<223> OTHER INFORMATION: Ala, Pro, D-Pro or Phe
<220> FEATURE:
<221> NAME/KEY: MOD_RES
<222> LOCATION: (9)..(9)
<223> OTHER INFORMATION: Pro or Ala
<220> FEATURE:
<221> NAME/KEY: MOD_RES
<222> LOCATION: (10)..(10)
<223> OTHER INFORMATION: Glu, His, Ala, Thr or Lys
<220> FEATURE:
<221> NAME/KEY: MOD_RES
<222> LOCATION: (11)..(11)
<223> OTHER INFORMATION: His, Ala, Thr, Lys or Glu
<220> FEATURE:
<221> NAME/KEY: MOD_RES
<222> LOCATION: (12)..(12)
<223> OTHER INFORMATION: Ala or Thr
<220> FEATURE:
<221> NAME/KEY: MOD_RES
<222> LOCATION: (14)..(14)
<223> OTHER INFORMATION: Lys, Cys or Gly

<400> SEQUENCE: 35

```
Xaa Xaa Xaa Xaa Xaa Xaa Xaa Xaa Xaa Xaa Xaa Xaa Gly Xaa
1               5                   10
```

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(1)
<223> OTHER INFORMATION: Thr, Ala or Glu
<220> FEATURE:
<221> NAME/KEY: MOD_RES
<222> LOCATION: (2)..(2)
<223> OTHER INFORMATION: Gln, Glu, Lys or His
<220> FEATURE:
<221> NAME/KEY: MOD_RES
<222> LOCATION: (3)..(3)
<223> OTHER INFORMATION: Thr or Ala
<220> FEATURE:
<221> NAME/KEY: MOD_RES
<222> LOCATION: (4)..(4)
<223> OTHER INFORMATION: Leu or Lys
<220> FEATURE:
<221> NAME/KEY: MOD_RES
<222> LOCATION: (5)..(5)
<223> OTHER INFORMATION: Ala, His or Phe
<220> FEATURE:
<221> NAME/KEY: MOD_RES
<222> LOCATION: (6)..(6)
<223> OTHER INFORMATION: Lys or Glu
<220> FEATURE:
<221> NAME/KEY: MOD_RES
<222> LOCATION: (7)..(7)
<223> OTHER INFORMATION: Ala, Pro, D-Pro or Phe
<220> FEATURE:
<221> NAME/KEY: MOD_RES
<222> LOCATION: (8)..(8)
<223> OTHER INFORMATION: Pro or Ala
<220> FEATURE:
<221> NAME/KEY: MOD_RES
<222> LOCATION: (9)..(9)
<223> OTHER INFORMATION: Glu, His, Ala, Thr or Lys
<220> FEATURE:
<221> NAME/KEY: MOD_RES
<222> LOCATION: (10)..(10)
<223> OTHER INFORMATION: His, Ala, Thr, Lys or Glu
<220> FEATURE:
<221> NAME/KEY: MOD_RES
<222> LOCATION: (11)..(11)
<223> OTHER INFORMATION: Ala or Thr
<220> FEATURE:
<221> NAME/KEY: MOD_RES
<222> LOCATION: (13)..(13)
<223> OTHER INFORMATION: Lys, Cys or Gly

<400> SEQUENCE: 36

Xaa Xaa Xaa Xaa Xaa Xaa Xaa Xaa Xaa Xaa Xaa Gly Xaa
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Glu, Lys or His
<220> FEATURE:
<221> NAME/KEY: MOD_RES
<222> LOCATION: (2)..(2)
<223> OTHER INFORMATION: Thr or Ala
<220> FEATURE:
<221> NAME/KEY: MOD_RES
<222> LOCATION: (3)..(3)
<223> OTHER INFORMATION: Leu or Lys
<220> FEATURE:
<221> NAME/KEY: MOD_RES
<222> LOCATION: (4)..(4)
<223> OTHER INFORMATION: Ala, His or Phe
<220> FEATURE:
<221> NAME/KEY: MOD_RES
<222> LOCATION: (5)..(5)
```

```
<223> OTHER INFORMATION: Lys or Glu
<220> FEATURE:
<221> NAME/KEY: MOD_RES
<222> LOCATION: (6)..(6)
<223> OTHER INFORMATION: Ala, Pro, D-Pro or Phe
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Glu, His, Ala, Thr or Lys
<220> FEATURE:
<221> NAME/KEY: MOD_RES
<222> LOCATION: (9)..(9)
<223> OTHER INFORMATION: His, Ala, Thr, Lys or Glu
<220> FEATURE:
<221> NAME/KEY: MOD_RES
<222> LOCATION: (10)..(10)
<223> OTHER INFORMATION: Ala or Thr
<220> FEATURE:
<221> NAME/KEY: MOD_RES
<222> LOCATION: (12)..(12)
<223> OTHER INFORMATION: Lys, Cys or Gly

<400> SEQUENCE: 37

Xaa Xaa Xaa Xaa Xaa Xaa Xaa Xaa Xaa Xaa Gly Xaa
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr or Ala
<220> FEATURE:
<221> NAME/KEY: MOD_RES
<222> LOCATION: (2)..(2)
<223> OTHER INFORMATION: Leu or Lys
<220> FEATURE:
<221> NAME/KEY: MOD_RES
<222> LOCATION: (3)..(3)
<223> OTHER INFORMATION: Ala, His or Phe
<220> FEATURE:
<221> NAME/KEY: MOD_RES
<222> LOCATION: (4)..(4)
<223> OTHER INFORMATION: Lys or Glu
<220> FEATURE:
<221> NAME/KEY: MOD_RES
<222> LOCATION: (5)..(5)
<223> OTHER INFORMATION: Ala, Pro, D-Pro or Phe
<220> FEATURE:
<221> NAME/KEY: MOD_RES
<222> LOCATION: (6)..(6)
<223> OTHER INFORMATION: Pro or Ala
<220> FEATURE:
<221> NAME/KEY: MOD_RES
<222> LOCATION: (7)..(7)
<223> OTHER INFORMATION: Glu, His, Ala, Thr or Lys
<220> FEATURE:
<221> NAME/KEY: MOD_RES
<222> LOCATION: (8)..(8)
<223> OTHER INFORMATION: His, Ala, Thr, Lys or Glu
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (11)..(11)
<223> OTHER INFORMATION: Lys, Cys or Gly
```

```
<400> SEQUENCE: 38

Xaa Xaa Xaa Xaa Xaa Xaa Xaa Xaa Xaa Gly Xaa
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Lys
<220> FEATURE:
<221> NAME/KEY: MOD_RES
<222> LOCATION: (2)..(2)
<223> OTHER INFORMATION: Ala, His or Phe
<220> FEATURE:
<221> NAME/KEY: MOD_RES
<222> LOCATION: (3)..(3)
<223> OTHER INFORMATION: Lys or Glu
<220> FEATURE:
<221> NAME/KEY: MOD_RES
<222> LOCATION: (4)..(4)
<223> OTHER INFORMATION: Ala, Pro, D-Pro or Phe
<220> FEATURE:
<221> NAME/KEY: MOD_RES
<222> LOCATION: (5)..(5)
<223> OTHER INFORMATION: Pro or Ala
<220> FEATURE:
<221> NAME/KEY: MOD_RES
<222> LOCATION: (6)..(6)
<223> OTHER INFORMATION: Glu, His, Ala, Thr or Lys
<220> FEATURE:
<221> NAME/KEY: MOD_RES
<222> LOCATION: (7)..(7)
<223> OTHER INFORMATION: His, Ala, Thr, Lys or Glu
<220> FEATURE:
<221> NAME/KEY: MOD_RES
<222> LOCATION: (8)..(8)
<223> OTHER INFORMATION: Ala or Thr
<220> FEATURE:
<221> NAME/KEY: MOD_RES
<222> LOCATION: (10)..(10)
<223> OTHER INFORMATION: Lys, Cys or Gly

<400> SEQUENCE: 39

Xaa Xaa Xaa Xaa Xaa Xaa Xaa Xaa Gly Xaa
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, His or Phe
<220> FEATURE:
<221> NAME/KEY: MOD_RES
<222> LOCATION: (2)..(2)
<223> OTHER INFORMATION: Lys or Glu
<220> FEATURE:
<221> NAME/KEY: MOD_RES
<222> LOCATION: (3)..(3)
<223> OTHER INFORMATION: Ala, Pro, D-Pro or Phe
<220> FEATURE:
<221> NAME/KEY: MOD_RES
<222> LOCATION: (4)..(4)
```

```
<223> OTHER INFORMATION: Pro or Ala
<220> FEATURE:
<221> NAME/KEY: MOD_RES
<222> LOCATION: (5)..(5)
<223> OTHER INFORMATION: Glu, His, Ala, Thr or Lys
<220> FEATURE:
<221> NAME/KEY: MOD_RES
<222> LOCATION: (6)..(6)
<223> OTHER INFORMATION: His, Ala, Thr, Lys or Glu
<220> FEATURE:
<221> NAME/KEY: MOD_RES
<222> LOCATION: (7)..(7)
<223> OTHER INFORMATION: Ala or Thr
<220> FEATURE:
<221> NAME/KEY: MOD_RES
<222> LOCATION: (9)..(9)
<223> OTHER INFORMATION: Lys, Cys or Gly

<400> SEQUENCE: 40

Xaa Xaa Xaa Xaa Xaa Xaa Xaa Gly Xaa
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Glu
<220> FEATURE:
<221> NAME/KEY: MOD_RES
<222> LOCATION: (2)..(2)
<223> OTHER INFORMATION: Ala, Pro, D-Pro or Phe
<220> FEATURE:
<221> NAME/KEY: MOD_RES
<222> LOCATION: (3)..(3)
<223> OTHER INFORMATION: Pro or Ala
<220> FEATURE:
<221> NAME/KEY: MOD_RES
<222> LOCATION: (4)..(4)
<223> OTHER INFORMATION: Glu, His, Ala, Thr or Lys
<220> FEATURE:
<221> NAME/KEY: MOD_RES
<222> LOCATION: (5)..(5)
<223> OTHER INFORMATION: His, Ala, Thr, Lys or Glu
<220> FEATURE:
<221> NAME/KEY: MOD_RES
<222> LOCATION: (6)..(6)
<223> OTHER INFORMATION: Ala or Thr
<220> FEATURE:
<221> NAME/KEY: MOD_RES
<222> LOCATION: (8)..(8)
<223> OTHER INFORMATION: Lys, Cys or Gly

<400> SEQUENCE: 41

Xaa Xaa Xaa Xaa Xaa Xaa Gly Xaa
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Pro, D-Pro or Phe
<220> FEATURE:
<221> NAME/KEY: MOD_RES
```

<222> LOCATION: (2)..(2)
<223> OTHER INFORMATION: Pro or Ala
<220> FEATURE:
<221> NAME/KEY: MOD_RES
<222> LOCATION: (3)..(3)
<223> OTHER INFORMATION: Glu, His, Ala, Thr or Lys
<220> FEATURE:
<221> NAME/KEY: MOD_RES
<222> LOCATION: (4)..(4)
<223> OTHER INFORMATION: His, Ala, Thr, Lys or Glu
<220> FEATURE:
<221> NAME/KEY: MOD_RES
<222> LOCATION: (5)..(5)
<223> OTHER INFORMATION: Ala or Thr
<220> FEATURE:
<221> NAME/KEY: MOD_RES
<222> LOCATION: (7)..(7)
<223> OTHER INFORMATION: Lys, Cys or Gly

<400> SEQUENCE: 42

Xaa Xaa Xaa Xaa Xaa Gly Xaa
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pro or Ala
<220> FEATURE:
<221> NAME/KEY: MOD_RES
<222> LOCATION: (2)..(2)
<223> OTHER INFORMATION: Glu, His, Ala, Thr or Lys
<220> FEATURE:
<221> NAME/KEY: MOD_RES
<222> LOCATION: (3)..(3)
<223> OTHER INFORMATION: His, Ala, Thr, Lys or Glu
<220> FEATURE:
<221> NAME/KEY: MOD_RES
<222> LOCATION: (4)..(4)
<223> OTHER INFORMATION: Ala or Thr
<220> FEATURE:
<221> NAME/KEY: MOD_RES
<222> LOCATION: (6)..(6)
<223> OTHER INFORMATION: Lys, Cys or Gly

<400> SEQUENCE: 43

Xaa Xaa Xaa Xaa Gly Xaa
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, His, Ala, Thr or Lys
<220> FEATURE:
<221> NAME/KEY: MOD_RES
<222> LOCATION: (2)..(2)
<223> OTHER INFORMATION: His, Ala, Thr, Lys or Glu
<220> FEATURE:
<221> NAME/KEY: MOD_RES
<222> LOCATION: (3)..(3)
<223> OTHER INFORMATION: Ala or Thr
<220> FEATURE:

```
<221> NAME/KEY: MOD_RES
<222> LOCATION: (5)..(5)
<223> OTHER INFORMATION: Lys, Cys or Gly

<400> SEQUENCE: 44

Xaa Xaa Xaa Gly Xaa
1               5

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: His, Ala, Thr, Lys or Glu
<220> FEATURE:
<221> NAME/KEY: MOD_RES
<222> LOCATION: (2)..(2)
<223> OTHER INFORMATION: Ala or Thr
<220> FEATURE:
<221> NAME/KEY: MOD_RES
<222> LOCATION: (4)..(4)
<223> OTHER INFORMATION: Lys, Cys or Gly

<400> SEQUENCE: 45

Xaa Xaa Gly Xaa
1

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala or Thr
<220> FEATURE:
<221> NAME/KEY: MOD_RES
<222> LOCATION: (3)..(3)
<223> OTHER INFORMATION: Lys, Cys or Gly

<400> SEQUENCE: 46

Xaa Gly Xaa
1

<210> SEQ ID NO 47
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys, Cys or Gly

<400> SEQUENCE: 47

Gly Xaa
1

<210> SEQ ID NO 48
<211> LENGTH: 1
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Cys or Gly

<400> SEQUENCE: 48

Xaa
1

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, His, Ala, Thr or Lys
<220> FEATURE:
<221> NAME/KEY: MOD_RES
<222> LOCATION: (2)..(2)
<223> OTHER INFORMATION: His, Ala, Thr, Lys or Glu
<220> FEATURE:
<221> NAME/KEY: MOD_RES
<222> LOCATION: (3)..(3)
<223> OTHER INFORMATION: Ala or Thr
<220> FEATURE:
<221> NAME/KEY: MOD_RES
<222> LOCATION: (5)..(5)
<223> OTHER INFORMATION: Lys, Cys or Gly

<400> SEQUENCE: 49

Xaa Xaa Xaa Gly Xaa Gly
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, His, Ala, Thr or Lys
<220> FEATURE:
<221> NAME/KEY: MOD_RES
<222> LOCATION: (2)..(2)
<223> OTHER INFORMATION: His, Ala, Thr, Lys or Glu
<220> FEATURE:
<221> NAME/KEY: MOD_RES
<222> LOCATION: (3)..(3)
<223> OTHER INFORMATION: Ala or Thr
<220> FEATURE:
<221> NAME/KEY: MOD_RES
<222> LOCATION: (5)..(5)
<223> OTHER INFORMATION: Lys, Cys or Gly

<400> SEQUENCE: 50

Xaa Xaa Xaa Gly Xaa Gly Cys
1               5

<210> SEQ ID NO 51
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<223> OTHER INFORMATION: C-term NH2

<400> SEQUENCE: 51

Arg Pro Lys Arg Pro Thr Thr Leu Asn Leu Phe
1               5                   10

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Lys His Thr Asp Asp Gly Tyr Met Pro Met Ser Pro Gly Val Ala
1               5                   10                  15

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Arg Gln Ile Lys Ile Trp Phe Gln Asn Arg Arg Met Lys Trp Lys
1               5                   10                  15

Lys Thr Ala Leu Asp Trp Ser Trp Leu Gln Thr Glu
            20                  25

<210> SEQ ID NO 54
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 55
<211> LENGTH: 29
<212> TYPE: PRT
<213> ORGANISM: Unknown
<220> FEATURE:
<223> OTHER INFORMATION: Description of Unknown: TIRAP
      inhibitor peptide

<400> SEQUENCE: 55

Arg Gln Ile Lys Ile Trp Phe Asn Arg Arg Met Lys Trp Lys Lys Leu
1               5                   10                  15

Gln Leu Arg Asp Ala Ala Pro Gly Gly Ala Ile Val Ser
            20                  25
```

```
<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<221> NAME/KEY: MOD_RES
<222> LOCATION: (2)..(2)
<223> OTHER INFORMATION: Glu(OMe)
<220> FEATURE:
<221> NAME/KEY: MOD_RES
<222> LOCATION: (4)..(4)
<223> OTHER INFORMATION: Asp(OMe)
<220> FEATURE:
<223> OTHER INFORMATION: C-term fluoromethylketone

<400> SEQUENCE: 56

Leu Glu His Asp
1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term N-Acetyl
<220> FEATURE:
<223> OTHER INFORMATION: C-term CHO

<400> SEQUENCE: 57

Leu Glu His Asp
1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term N-Acetyl
<220> FEATURE:
<223> OTHER INFORMATION: C-term CHO

<400> SEQUENCE: 58

Ile Glu Thr Asp
1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term benzyloxycarbonyl
<220> FEATURE:
<221> NAME/KEY: MOD_RES
<222> LOCATION: (2)..(2)
<223> OTHER INFORMATION: Glu(OMe)
<220> FEATURE:
<221> NAME/KEY: MOD_RES
<222> LOCATION: (4)..(4)
<223> OTHER INFORMATION: Asp(OMe)
```

```
<220> FEATURE:
<223> OTHER INFORMATION: C-term fluoromethylketone

<400> SEQUENCE: 59

Ile Glu Thr Asp
1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term FAM
<220> FEATURE:
<223> OTHER INFORMATION: C-term fluoromethylketone

<400> SEQUENCE: 60

Leu Glu His Asp
1

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term FAM
<220> FEATURE:
<223> OTHER INFORMATION: C-term fluoromethylketone

<400> SEQUENCE: 61

Leu Glu Thr Asp
1

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (17)..(17)
<223> OTHER INFORMATION: Lys(6FAM)
<220> FEATURE:
<223> OTHER INFORMATION: C-term NH2

<400> SEQUENCE: 62

Ser His Ser Asn Thr Gln Thr Leu Ala Lys Ala Pro Glu His Thr Gly
1               5                   10                  15

Lys

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: MOD_RES
<222> LOCATION: (17)..(17)
<223> OTHER INFORMATION: Cys(Cy5)
<220> FEATURE:
<223> OTHER INFORMATION: C-term NH2

<400> SEQUENCE: 63

Ser His Ser Asn Thr Gln Thr Leu Ala Lys Ala Pro Glu His Thr Gly
1               5                   10                  15
Cys

<210> SEQ ID NO 64
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (1)..(1)
<223> OTHER INFORMATION: Lys(6FAM)
<220> FEATURE:
<223> OTHER INFORMATION: C-term NH2

<400> SEQUENCE: 64

Lys
1

<210> SEQ ID NO 65
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Lys(6FAM)
<220> FEATURE:
<223> OTHER INFORMATION: C-term NH2

<400> SEQUENCE: 65

Gly Lys
1

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Lys(6FAM)
<220> FEATURE:
<223> OTHER INFORMATION: C-term NH2

<400> SEQUENCE: 66

Glu His Thr Gly Lys
1               5
```

```
<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Lys(6FAM)
<220> FEATURE:
<223> OTHER INFORMATION: C-term NH2

<400> SEQUENCE: 67

Lys Ala Pro Glu His Thr Gly Lys
1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (10)..(10)
<223> OTHER INFORMATION: Lys(6FAM)
<220> FEATURE:
<223> OTHER INFORMATION: C-term NH2

<400> SEQUENCE: 68

Leu Ala Lys Ala Pro Glu His Thr Gly Lys
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (12)..(12)
<223> OTHER INFORMATION: Lys(6FAM)
<220> FEATURE:
<223> OTHER INFORMATION: C-term NH2

<400> SEQUENCE: 69

Gln Thr Leu Ala Lys Ala Pro Glu His Thr Gly Lys
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (13)..(13)
```

<223> OTHER INFORMATION: Lys(6FAM)
<220> FEATURE:
<223> OTHER INFORMATION: C-term NH2

<400> SEQUENCE: 70

Thr Gln Thr Leu Ala Lys Ala Pro Glu His Thr Gly Lys
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 71

Asn Thr Gln Thr Leu Ala Lys Ala Pro Glu His Thr Gly Lys
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 72

Asn Thr Gln Thr Leu Ala Lys Ala Pro Glu His Ala Gly Lys
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 73

Asn Thr Gln Thr Leu Ala Lys Ala Pro Glu Ala Thr Gly Lys
1               5                   10

<210> SEQ ID NO 74
<211> LENGTH: 14
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 74

Asn Thr Gln Thr Leu Ala Lys Ala Pro His Glu Thr Gly Lys
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 75

Asn Thr Gln Thr Leu Ala Lys Ala Pro Ala His Thr Gly Lys
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 76

Asn Thr Gln Thr Leu Ala Lys Ala Pro Lys His Thr Gly Lys
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

```
<400> SEQUENCE: 77

Asn Thr Gln Thr Leu Ala Lys Ala Ala Glu His Thr Gly Lys
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: D-Pro
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 78

Asn Thr Gln Thr Leu Ala Lys Ala Pro Glu His Thr Gly Lys
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 79

Asn Thr Gln Thr Leu Ala Lys Pro Pro Glu His Thr Gly Lys
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 80

Asn Thr Gln Thr Leu Ala Lys Phe Pro Glu His Thr Gly Lys
1               5                   10

<210> SEQ ID NO 81
<211> LENGTH: 14
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 81

Asn Thr Gln Thr Leu Ala Glu Ala Pro Glu His Thr Gly Lys
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 82

Asn Thr Gln Thr Leu His Glu Ala Pro Glu His Thr Gly Lys
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 83

Asn Thr Gln Thr Leu Phe Lys Ala Pro Glu His Thr Gly Lys
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

```
<400> SEQUENCE: 84

Asn Thr Gln Thr Lys Ala Lys Ala Pro Glu His Thr Gly Lys
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 85

Asn Thr Gln Ala Leu Ala Lys Ala Pro Glu His Thr Gly Lys
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 86

Asn Thr Glu Thr Leu Ala Lys Ala Pro Glu His Thr Gly Lys
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 87

Asn Thr Lys Thr Leu Ala Lys Ala Pro Glu His Thr Gly Lys
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 88

Asn Ala Gln Thr Leu Ala Lys Ala Pro Glu His Thr Gly Lys
 1               5                  10

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 89

Ala Thr Gln Thr Leu Ala Lys Ala Pro Glu His Thr Gly Lys
 1               5                  10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Lys(6FAM)
<220> FEATURE:
<223> OTHER INFORMATION: C-term NH2

<400> SEQUENCE: 90

Pro Glu His Thr Leu Ala Lys Ala Pro Glu His Thr Gly Lys
 1               5                  10

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: Cys(Cy5)
<220> FEATURE:
<223> OTHER INFORMATION: C-term NH2

<400> SEQUENCE: 91

Glu His Thr Gly Cys
 1               5
```

```
<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Cys(Cy5)
<220> FEATURE:
<223> OTHER INFORMATION: C-term NH2

<400> SEQUENCE: 92

Glu His Thr Gly Gly Gly Cys
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Cys(Cy5)
<220> FEATURE:
<223> OTHER INFORMATION: C-term NH2

<400> SEQUENCE: 93

Thr Thr Thr Gly Gly Gly Cys
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Cys(Cy5)
<220> FEATURE:
<223> OTHER INFORMATION: C-term NH2

<400> SEQUENCE: 94

Glu Glu Thr Gly Gly Gly Cys
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Cys(Cy5)
```

```
<220> FEATURE:
<223> OTHER INFORMATION: C-term NH2

<400> SEQUENCE: 95

Lys His Thr Gly Gly Gly Cys
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Cys(Cy5)
<220> FEATURE:
<223> OTHER INFORMATION: C-term NH2

<400> SEQUENCE: 96

Glu Lys Thr Gly Gly Gly Cys
1               5
```